(12) United States Patent (10) Patent No.: US 8,748,432 B2
Lamberth et al. (45) Date of Patent: Jun. 10, 2014

(54) MICROBIOCIDAL PYRAZOLE DERIVATIVES

(75) Inventors: Clemens Lamberth, Stein (CH); Sarah Sulzer-Mosse, Stein (CH); Fredrik Cederbaum, Stein (CH); Guillaume Berthon, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 13/984,449

(22) PCT Filed: Feb. 8, 2012

(86) PCT No.: PCT/EP2012/052107
§ 371 (c)(1),
(2), (4) Date: Aug. 8, 2013

(87) PCT Pub. No.: WO2012/107475
PCT Pub. Date: Aug. 16, 2012

(65) Prior Publication Data
US 2013/0324553 A1 Dec. 5, 2013

(30) Foreign Application Priority Data
Feb. 10, 2011 (EP) .................................... 11153988

(51) Int. Cl.
*A61K 31/497* (2006.01)
*A61K 31/4523* (2006.01)
*C07D 403/14* (2006.01)
*C07D 401/14* (2006.01)

(52) U.S. Cl.
USPC ....... 514/254.05; 514/326; 544/371; 546/211

(58) Field of Classification Search
USPC ............... 514/254.05, 326; 544/371; 546/211
See application file for complete search history.

(56) References Cited

FOREIGN PATENT DOCUMENTS

| WO | 2008/091580 | 7/2008 |
| WO | 2008/091594 | 7/2008 |
| WO | 2009/055514 | 4/2009 |

OTHER PUBLICATIONS

International Search Report, International Application No. PCT/EP2012/052107, completion date: Mar. 5, 2012.

*Primary Examiner* — Samantha Shterengarts
(74) *Attorney, Agent, or Firm* — R. Kody Jones

(57) ABSTRACT

The present invention provides compounds of formula (I): wherein the substituents are as defined in claim 1, are useful as active ingredients, which have microbiocidal activity, in particular fungicidal activity.

(I)

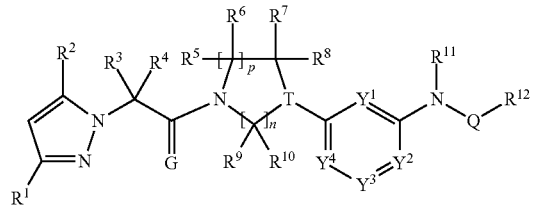

15 Claims, No Drawings

MICROBIOCIDAL PYRAZOLE DERIVATIVES

This application is a 371 of International Application No. PCT/EP2012/052107 filed Feb. 8, 2012, which claims priority to EP 11153988.8 filed Feb. 10, 2011, the contents of which are incorporated herein by reference.

The present invention relates to microbiocidal pyrazole derivatives, e.g. as active ingredients, which have microbiocidal activity, in particular fungicidal activity. The invention also relates to preparation of these pyrazole derivatives, to pyrazole derivatives used as intermediates in the preparation of these pyrazole derivatives, to preparation of these intermediates, to agrochemical compositions which comprise at least one of the pyrazole derivatives, to preparation of these compositions and to use of the pyrazole derivatives or compositions in agriculture or horticulture for controlling or preventing infestation of plants, harvested food crops, seeds or non-living materials by phytopathogenic microorganisms, preferably fungi.

Certain compounds for use as fungicides are described in WO 2007/014290, WO 2008/013622, WO 2008/013925, WO 2008/091580, WO 2008/091594 and WO 2009/055514.

The present invention provides compounds of formula I:

(I)

wherein

G is O or S;

T is $CR^{13}$ or N;

$Y^1$, $Y^2$, $Y^3$ and $Y^4$ are independently $CR^{14}$ or N;

Q is —C(=O)-z, —C(=S)-z, —C(=O)—O-z, —C(=O)—N($R^{15}$)-z or —C(=S)—N($R^{16}$)-z, in each case z indicates the bond that is connected to $R^{12}$;

n is 1 or 2;

p is 1 or 2, providing that when n is 2, p is 1;

$R^1$, $R^2$, $R^3$, $R^4$, $R^5$, $R^6$, $R^7$, $R^8$, $R^9$, $R^{10}$, $R^{13}$ and $R^{14}$ each independently are hydrogen, halogen, cyano, $C_1$-$C_4$alkyl or $C_1$-$C_4$haloalkyl;

$R^{11}$, $R^{15}$ and $R^{16}$ each independently are hydrogen, $C_1$-$C_4$alkyl, $C_3$-$C_5$cycloalkyl or $C_1$-$C_4$alkoxy;

$R^{12}$ is aryl, heteroaryl, arylalkyl, heteroarylalkyl, a group (A) or a group (B):

(A)

(B)

wherein the aryl, heteroaryl, arylalkyl and heteroarylalkyl are optionally substituted by one or more $R^{29}$;

A is $C(R^{18}R^{19})$, C(=O), C(=S), $NR^{24}$, O or S;

$X^1$ is $C(R^{20}R^{21})$, C(=O), C(=S), $NR^{24}$, O or S;

$X^2$ is $C(R^{22}R^{23})$, C(=O), C(=S), $NR^{24}$, O or S;

$R^{17}$ is hydroxyl, $O^-M^+$, OC(=O)$R^{28}$, amino or $NHR^{25}$;

$M^+$ is a metal cation or ammonium cation;

$R^{18}$, $R^{19}$, $R^{20}$, $R^{21}$, $R^{22}$ and $R^{23}$ each independently are hydrogen, halogen, hydroxyl, amino, cyano, $C_2$-$C_8$alkenyl, $C_2$-$C_8$alkynyl, $C_3$-$C_8$cycloalkyl, $C_1$-$C_8$alkoxy, $C_1$-$C_8$alkylthio, $C_1$-$C_8$alkylsulfonyl, $C_1$-$C_8$alkylsulfinyl, aryl, heteroaryl or $NHR^{25}$, wherein alkyl, alkenyl, alkynyl, cycloalkyl, alkoxy, aryl and heteroaryl are optionally substituted by one or more $R^{26}$; and wherein $R^{18}$ and $R^{19}$, $R^{20}$ and $R^{21}$, and/or $R^{22}$ and $R^{23}$ may together form a saturated three- to six-membered alicyclic or heterocyclic ring wherein the aliyclic and heterocyclic rings are optionally substituted by one or more $R^{27}$; and/or $R^{18}$ and $R^{20}$, and/or $R^{21}$ and $R^{22}$ may together form a saturated or partially unsaturated four- to seven-membered alicyclic or heterocyclic ring wherein the aliyclic and heterocyclic rings are optionally substituted by one or more $R^{27}$; and/or $R^{18}$ and $R^{22}$ may together form a saturated or partially unsaturated four- to seven-membered alicyclic or heterocyclic ring wherein the alicyclic and heterocyclic rings are optionally substituted by one or more $R^{27}$;

$R^{24}$ and $R^{25}$ each independently are hydrogen, $C_1$-$C_8$alkyl, $C_1$-$C_8$haloalkyl, $C_2$-$C_8$alkenyl, $C_1$-$C_8$haloalkenyl, $C_2$-$C_8$alkynyl, $C_2$-$C_8$haloalkynyl, $C_3$-$C_8$cycloalkyl, $C_3$-$C_8$halocycloalkyl, $C_1$-$C_8$alkoxy, $C_1$-$C_8$haloalkoxy, $C_1$-$C_8$alkylcarbonyl, $C_1$-$C_8$haloalkylcarbonyl, $C_1$-$C_8$alkylsulfonyl or $C_1$-$C_8$haloalkylsulfonyl, amino, NH($C_1$-$C_8$alkyl), N($C_1$-$C_8$alkyl)$_2$, aryl or heterocycyl, wherein aryl and heterocyclyl are optionally substituted by one or more $R^{27}$;

each $R^{26}$ independently is halogen, cyano, amino, nitro, hydroxyl, mercapto, $C_1$-$C_8$alkyl, $C_2$-$C_8$alkenyl, $C_2$-$C_8$alkynyl, $C_3$-$C_8$cycloalkyl, $C_3$-$C_8$cycloalkyl-$C_1$-$C_4$alkyl, $C_3$-$C_8$cycloalkyl-$C_1$-$C_4$alkyloxy, $C_3$-$C_8$cycloalkyl-$C_1$-$C_4$alkylthio, $C_1$-$C_8$alkoxy, $C_3$-$C_8$cycloalkyloxy, $C_1$-$C_8$alkenyloxy, $C_2$-$C_8$alkynyloxy, $C_1$-$C_8$alkylthio, $C_1$-$C_8$alkylsulfonyl, $C_1$-$C_8$alkylsulfinyl, $C_3$-$C_8$cycloalkylthio, $C_3$-$C_8$cycloalkylsulfonyl, $C_3$-$C_8$cycloalkylsulfinyl, aryl, aryloxy, arylthio, arylsulfonyl, arylsulfinyl, aryl-$C_1$-$C_4$alkyl, aryl-$C_1$-$C_4$alkyloxy, aryl-$C_1$-$C_4$alkylthio, heterocyclyl, heterocycyl-$C_1$-$C_4$alkyl, heterocyclyl-$C_1$-$C_4$alkyloxy, heterocyclyl-$C_1$-$C_4$alkylthio, NH($C_1$-$C_8$alkyl), N($C_1$-$C_8$alkyl)$_2$, $C_4$alkylcarbonyl, $C_3$-$C_8$cycloalkylcarbonyl, $C_2$-$C_8$alkenylcarbonyl, $C_2$-$C_8$alkynylcarbonyl, wherein alkyl, alkenyl, alkynyl, cycloalkyl, alkoxy, alkenyloxy, alkynyloxy and cycloalkoxy are optionally substituted by halogen, and wherein aryl and heterocyclyl are optionally substituted by one or more $R^{27}$;

each $R^{27}$ is independently is halogen, cyano, $C_1$-$C_4$alkyl, $C_1$-$C_4$haloalkyl, $C_1$-$C_4$alkoxy or $C_1$-$C_4$haloalkoxy;

$R^{28}$ is $C_1$-$C_6$alkyl or $C_1$-$C_6$alkoxy;

each $R^{29}$ independently is halogen, hydroxyl, cyano, mercapto, nitro, $C_1$-$C_4$alkyl, $C_1$-$C_4$haloalkyl, $C_1$-$C_4$alkoxy, $C_1$-$C_4$haloalkoxy, $C_1$-$C_4$alkylthio, $N(R^{30})_2$, phenyl or heteroaryl, wherein phenyl and heteroaryl are optionally substituted by one or more substituents independently selected from halogen, cyano, $C_1$-$C_4$ alkyl, $C_1$-$C_4$ haloalkyl, $C_1$-$C_4$ alkoxy and $C_1$-$C_4$ haloalkoxy;

each $R^{30}$ independently is hydrogen, cyano, $C_1$-$C_4$alkyl, $C_1$-$C_4$alkylcarbonyl, $C_1$-$C_4$haloalkylcarbonyl, $C_1$-$C_4$alkylsulfonyl or $C_1$-$C_4$haloalkylsulfonyl;

e is 1 or 2;

q is 1, 2, or 3; and m is 0 or 1, providing that when m is 1, $X^1$ and $X^2$ cannot both be oxygen;

or a salt or a N-oxide thereof.

Where substituents are indicated as being optionally substituted, this means that they may or may not carry one or more identical or different substituents, e.g. one to five substituents, e.g. one to three substituents. Normally not more than three such optional substituents are present at the same time. Where a group is indicated as being substituted, e.g. alkyl, unless stated otherwise this includes those groups that are part of other groups, e.g. alkyl in alkylthio.

The term "halogen" refers to fluorine, chlorine, bromine or iodine, preferably fluorine, chlorine or bromine.

Alkyl substituents may be straight-chained or branched. Alkyl on its own or as part of another substituent is, depending upon the number of carbon atoms mentioned, for example, methyl, ethyl, n-propyl, n-butyl, n-pentyl, n-hexyl and the isomers thereof, for example, iso-propyl, iso-butyl, sec-butyl, tert-butyl, iso-amyl or pivaloyl.

Alkenyl substituents can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$ and most preferably $C_2$-$C_3$ alkenyl groups.

Alkynyl substituents can be in the form of straight or branched chains. Examples are ethynyl and propargyl. The alkynyl groups are preferably $C_2$-$C_6$, more preferably $C_2$-$C_4$ and most preferably $C_2$-$C_3$ alkynyl groups.

Haloalkyl groups may contain one or more identical or different halogen atoms and, for example, may stand for $CH_2Cl$, $CHCl_2$, $CCl_3$, $CH_2F$, $CHF_2$, $CF_3$, $CF_3CH_2$, $CH_3CF_2$, $CF_3CF_2$ or $CCl_3CCl_2$.

Haloalkenyl groups are alkenyl groups, respectively, which are substituted with one or more of the same or different halogen atoms and are, for example, 2,2-difluorovinyl or 1,2-dichloro-2-fluoro-vinyl.

Haloalkynyl groups are alkynyl groups, respectively, which are substituted with one or more of the same or different halogen atoms and are, for example, 1-chloro-prop-2-ynyl.

Alkoxy means a radical —OR, where R is alkyl, e.g. as defined above. Alkoxy groups include, but are not limited to, methoxy, ethoxy, 1-methylethoxy, propoxy, butoxy, 1-methylpropoxy and 2-methylpropoxy.

Cyano means a —CN group.

Amino means an $NH_2$ group.

Hydroxyl or hydroxy stands for a —OH group.

Aryl means a ring system which may be mono-, bi- or tricyclic. Examples of such rings include phenyl, naphthalenyl, anthracenyl, indenyl or phenanthrenyl. A preferred aryl group is phenyl.

Arylalkyl means a group A-B-, wherein A is aryl as defined above and B is an alkyl group as defined above. An example is phenyl-$C_1$-$C_4$alkyl, benzyl being preferred.

Heteroaryl stands for aromatic ring systems comprising mono-, bi- or tricyclic systems wherein at least one oxygen, nitrogen or sulfur atom is present as a ring member. Monocyclic and bicyclic aromatic ring systems are preferred, monocyclic ring systems are more preferred. For example, monocyclic heteoraryl may be a 5- to 7-membered aromatic ring containing one to three heteroatoms selected from oxygen, nitrogen and sulfur, more preferably selected from nitrogen and sulfur. Bicyclic heteroaryl may be a 9- to 11-membered bicyclic ring containing one to five heteroatoms, preferably one to three heteroatoms, selected from oxygen, nitrogen and sulfur. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, imiazothiazoyl, quinolinyl, quinoxalinyl, isoquinolinyl, phthalazinyl, quinoxalinyl, quinazolinyl, cinnolinyl and naphthyridinyl, preferably pyridyl, pyrazinyl, pyridazinyl, pyrimidinyl, pyrrolyl, pyrazolyl, imidazolyl, triazolyl, furanyl, thienyl thiazolyl or thiadiazolyl. Heteroaryl rings do not contain adjacent oxygen ring atoms, adjacent sulfur ring atoms or adjacent oxygen and sulfur ring atoms. A link to a heteroaryl group can be via a carbon atom or via a nitrogen atom. The heteroaryl linked to Q can be linked by a carbon atom or by a nitrogen atom.

Heteroarylalkyl means a group C-D-, wherein C is a heteroaryl group as defined above and D is an alkyl group as defined above. An example is heteroaryl-$C_1$-$C_4$alkyl, e.g. heteroaryl-methyl. Pyridyl-methyl is a specific example.

Heterocyclyl is defined to include heteroaryl and in addition their unsaturated or partially unsaturated analogues.

When $R^{12}$ is group (A) the compound may occur in different tautomeric forms, for example, when $R^{17}$ is hydroxyl, in the formulas I.a, I.b and I.c. Each form is included within the compounds of formula I.

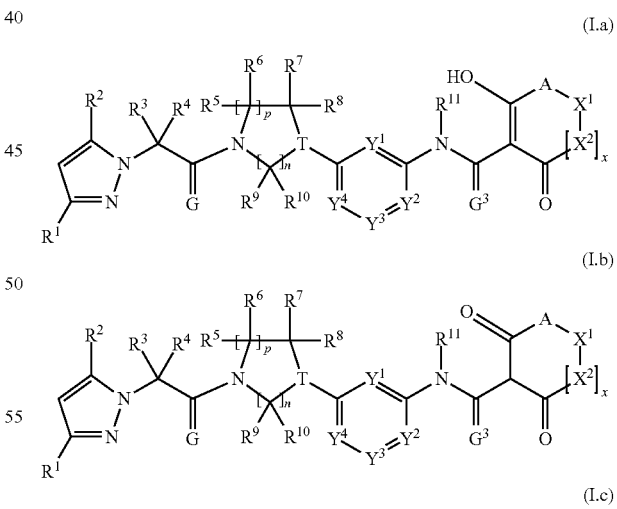

(I.a)

(I.b)

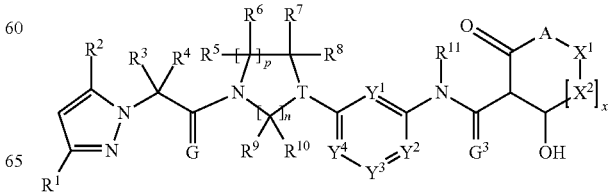

(I.c)

The presence of one or more possible asymmetric carbon atoms in a compound of formula I means that the compounds may occur in optically isomeric forms, i.e. enantiomeric or diastereomeric forms. Also atropisomers may occur as a result of restricted rotation about a single bond. Formula I is intended to include all those possible isomeric forms and mixtures thereof. The present invention includes all those possible isomeric forms and mixtures thereof for a compound of formula I. Likewise, formula I is intended to include all possible tautomers. The present invention includes all possible tautomeric forms for a compound of formula I.

In each case, the compounds of formula I according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

Suitable salts of the compounds of formula I include those resulting after addition of acid such as those with an inorganic mineral acid e.g. hydrochloric, hydrobromic, sulphuric, nitric or phosphoric acid, or an organic carboxylic acid e.g. oxalic, tartaric, lactic, butyric, toluic, hexanoic or phthalic acid, or a sulfonic acid e.g. methane, benzene or toluene sulfonic acid.

The following list provides definitions, including preferred definitions, for substituents G, T, $Y^1$, $Y^2$, $Y^3$, $Y^4$, Q, A, $X^1$, $X^2$, n, p, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$ $R^{26}$, $R^{27}$, $R^{28}$, $R^{29}$ and $R^{30}$ with reference to compounds of formula I and other compounds of the invention carrying the same substituents. For any one of these substituents, any of the definitions given below may be combined with any definition of any other substituent given below or elsewhere in this document.

G is O or S, preferably O.

T is $CR^{13}$ or N, preferably CH or N, more preferably CH.

$Y^1$, $Y^2$, $Y^3$, and $Y^4$ are independently $CR^{14}$ or N, e.g. $Y^1$, $Y^2$, $Y^3$, and $Y^4$ may be independently CH or N. Preferably, $Y^1$, $Y^2$, $Y^3$, and $Y^4$ are independently $CR^{14}$ or N providing that at least 2 of $Y^1$, $Y^2$, $Y^3$, and $Y^4$ are $CR^{14}$. Even more preferably, $Y^1$, $Y^2$, $Y^3$, and $Y^4$ are independently $CR^{14}$ or N providing that at least 2 of $Y^1$, $Y^2$, $Y^3$, and $Y^4$ are $CR^{14}$. Yet more preferably, $Y^1$, $Y^2$, $Y^3$, and $Y^4$ are independently CH or N providing that at least 2 of $Y^1$, $Y^2$, $Y^3$, and $Y^4$ are CH. Even more preferably at least three of $Y^1$, $Y^2$, $Y^3$, and $Y^4$ are CH and the other of $Y^1$, $Y^2$, $Y^3$, and $Y^4$ is N. Preferably $Y^2$ is N.

Q is —C(=O)-z, —C(=S)-z, —C(=O)—O-z, —C(=O)—N($R^{15}$)-z or —C(=S)—N($R^{16}$)-z, in each case z indicates the bond that is connected to $R^{12}$, preferably Q is —C(=O)-z, —C(=O)—O-z, —C(=O)—N($R^{15}$)-z or —C(=S)—N($R^{16}$)-z, more preferably Q is —C(=O)-z, —C(=O)—O-z, —C(=O)—N($R^{15}$)-z, even more preferably Q is —C(=O)-z.

n is 1 or 2. Preferably, n is 2.

p is 1 or 2, providing that when n is 2, p is 1. Preferably, p is 1.

$R^1$, $R^2$, $R^3$, $R^4$, $R^5$, $R^6$, $R^7$, $R^8$, $R^9$, $R^{10}$, $R^{13}$ and $R^{14}$ each independently are hydrogen, halogen, cyano, $C_1$-$C_4$alkyl or $C_1$-$C_4$haloalkyl, preferably hydrogen, halogen, $C_1$-$C_4$alkyl or $C_1$-$C_4$haloalkyl.

Preferably $R^1$ and $R^2$ are each independently halogen, methyl or halomethyl, more preferably methyl of halomethyl, even more preferably methyl or trifluoromethyl. Preferably $R^1$ is trifluoromethyl. Preferably $R^2$ is methyl.

Preferably $R^3$, $R^4$, $R^5$, $R^6$, $R^7$, $R^8$, $R^9$, $R^{10}$, $R^{13}$ and $R^{14}$ are each independently hydrogen, halogen, $C_1$-$C_4$alkyl or $C_1$-$C_4$haloalkyl, more preferably hydrogen, halogen, methyl or halomethyl, even more preferably hydrogen or methyl, most preferably hydrogen.

$R^{11}$, $R^{15}$ and $R^{16}$ each independently are hydrogen, $C_1$-$C_4$alkyl, $C_3$-$C_5$cycloalkyl or $C_1$-$C_4$alkoxy, more preferably hydrogen or methyl, even more preferably hydrogen.

$R^{12}$ is aryl, heteroaryl, arylalkyl, heteroarylalkyl, a group (A) or a group (B):

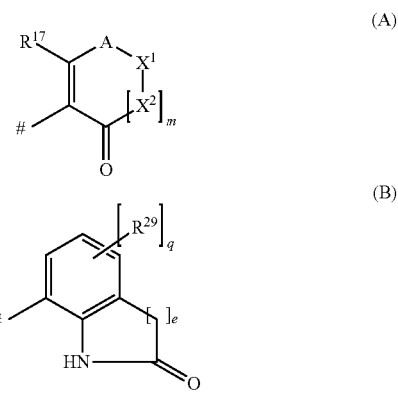

wherein the aryl, heteroaryl, arylalkyl and heteroarylalkyl are optionally substituted by one or more $R^{29}$. (In group (B) any carbon atom in either ring may be substituted by $R^{29}$).

Preferably $R^{12}$ is phenyl, heteroaryl, phenyl-$C_1$-$C_4$alkyl, heteroaryl-$C_1$-$C_4$alkyl, a group (A) or a group (B), wherein phenyl, phenyl-$C_1$-$C_4$alkyl, heteroaryl and heteroaryl-$C_1$-$C_4$alkyl are optionally substituted by one or more $R^{29}$; and wherein heteroaryl (including heteroaryl in heteroaryl-$C_1$-$C_4$alkyl) is selected from furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, imiazothiazoyl, quinolinyl, quinoxalinyl, isoquinolinyl, phthalazinyl, quinoxalinyl, quinazolinyl, cinnolinyl and naphthyridinyl. Preferably heteroaryl is selected from furyl, thienyl, thiazolyl, thiadiazolyl, pyridyl, pyrimidinyl, pyridazinyl, pyrazolyl, imidazothiazolyl, quinolinyl or quinoxalinyl, more preferably thienyl, thiadazolyl, pyridyl, pyrimidinyl, pyridazinyl, most preferably pyridyl.

A is $C(R^{18}R^{19}$, C(=O), C(=S), $NR^{24}$, O or S; $X^1$ is $C(R^{20}R^{21})$, C(=O), C(=S), $NR^{24}$, O or S; $X^2$ is $C(R^{22}R^{23})$, C(=O), C(=S), $NR^{24}$, O or S. Preferably there are no —O—O—, —S—S— or —O—S— in the ring formed by A, $X^1$ and $X^2$. Preferably there are no adjacent C=O groups in the ring formed by A, $X^1$ and $X^2$. Preferably no more than two of A, $X^1$ and $X^2$ are $NR^{24}$, O or S. In one group of compounds there are no adjacent heteroatoms in the ring formed by A, $X^1$ and $X^2$. In another group of compounds when m is 1 A is $C(R^{18}R^{19})$, $NR^{24}$, O or S; $X^1$ is $C(R^{20}R^{21})$, C(=O), C(=S), $NR^{24}$, O or S; and $X^2$ is $C(R^{22}R^{23})$, $NR^{24}$, O or S. In another group of compounds when m is 0, A is $C(R^{18}R^{19})$, C(=O), C(=S), $NR^{24}$, O or S; $X^1$ is $C(R^{20}R^{21})$, $NR^{24}$, O or S. Even more preferred options for A, $Q^1$ and $Q^2$ are depicted by A1 to A19 in formula I.d (see below).

$R^{17}$ is hydroxyl, $O^-M^+$, $OC(=O)R^{28}$, amino or $NHR^{25}$; preferably hydroxyl, $O^-M^+$, or $NHR^{25}$, more preferably hydroxyl or $O^-M^+$, even more preferably hydroxyl.

M⁺ is a metal cation or ammonium cation, preferably a metal cation, e.g. an alkali metal cation, such as potassium, sodium or lithium.

$R^{18}$, $R^{19}$ $R^{20}$, $R^{21}$, $R^{22}$ and $R^{23}$ each independently are hydrogen, halogen, hydroxyl, amino, cyano, $C_1$-$C_8$alkyl, $C_2$-$C_8$alkenyl, $C_2$-$C_8$alkynyl, $C_3$-$C_8$cycloalkyl, $C_1$-$C_8$alkoxy, $C_1$-$C_8$alkylthio, $C_1$-$C_8$alkylsulfonyl, $C_1$-$C_8$alkylsulfinyl, aryl, heteroaryl or $NHR^{24}$, wherein alkyl, alkenyl, alkynyl, cycloalkyl, alkoxy, aryl and heteroaryl are optionally substituted by one or more $R^{26}$.

Preferably $R^{18}$, $R^{19}$ $R^{20}$, $R^{21}$, $R^{22}$ and $R^{23}$ each independently are hydrogen, halogen, hydroxyl, cyano, $C_1$-$C_8$alkyl, $C_2$-$C_8$alkenyl, $C_2$-$C_8$alkynyl, $C_3$-$C_8$cycloalkyl, $C_1$-$C_8$alkoxy, $C_1$-$C_8$alkylthio, aryl, heteroaryl or $NHR^{24}$, wherein alkyl, alkenyl, alkynyl, cycloalkyl, alkoxy, aryl and heteroaryl are optionally substituted by one or more $R^{26}$.

Preferably $R^{18}$, $R^{19}$ $R^{20}$, $R^{21}$, $R^{22}$ and $R^{23}$ each independently are hydrogen, halogen, hydroxyl, cyano, $C_1$-$C_8$alkyl, $C_2$-$C_8$alkenyl, $C_2$-$C_8$alkynyl, $C_3$-$C_8$cycloalkyl, $C_1$-$C_8$alkoxy, $C_1$-$C_8$alkylthio, aryl, heteroaryl or $NHR^{24}$, wherein alkyl, alkenyl, alkynyl, cycloalkyl, alkoxy, aryl and heteroaryl are optionally substituted by one or more $R^{26}$ and wherein each heteroaryl is independently selected from pyridyl, pyrazinyl, pyridazinyl, pyrimidinyl, pyrrolyl, pyrazolyl, imidazolyl, triazolyl, furanyl, thienyl thiazolyl and thiadiazolyl.

Even more preferably $R^{18}$, $R^{19}$ $R^{20}$, $R^{21}$, $R^{22}$ and $R^{23}$ each independently are hydrogen, halogen, cyano, $C_1$-$C_4$alkyl, $C_3$-$C_6$cycloalkyl-$C_1$-$C_4$alkyl, $C_3$-$C_6$cycloalkyl-$C_1$-$C_4$alkyl wherein one ring atom is replaced by oxygen, $C_2$-$C_4$alkenyl, $C_2$-$C_4$alkynyl, $C_3$-$C_6$cycloalkyl, $C_4$alkylthio-$C_3$-$C_6$cycloalkyl, phenylthio-$C_3$-$C_6$cycloalkyl, benzylthio-$C_3$-$C_6$cycloalkyl, $C_3$-$C_6$cycloalkyl wherein one ring atom is replaced by oxygen, $C_1$-$C_4$alkoxy, $C_1$-$C_4$alkylthio, $C_4$alkylcarbonylamino, wherein alkyl, alkenyl, alkynyl, and cycloalkyl are optionally substituted by one to five halogen, and wherein phenyl and benzyl are optionally substituted by one to five groups selected from halogen, cyano, $C_1$-$C_4$alkyl, $C_1$-$C_4$haloalkyl, $C_1$-$C_4$alkoxy and $C_1$-$C_4$haloalkoxy.

$R^{18}$ and $R^{19}$, $R^{20}$ and $R^{21}$, and/or $R^{22}$ and $R^{23}$ may together form a saturated three- to six-membered alicyclic or heterocyclic ring wherein the aliyclic and heterocyclic rings are optionally substituted by one or more $R^{27}$; and/or $R^{18}$ and $R^{20}$, and/or $R^{21}$ and $R^{22}$ may together form a saturated or partially unsaturated four- to seven-membered alicyclic or heterocyclic ring wherein the aliyclic and heterocyclic rings are optionally substituted by one or more $R^{27}$; and/or $R^{18}$ and $R^{22}$ may together form a saturated or partially unsaturated four- to seven-membered alicyclic or heterocyclic ring wherein the aliyclic and heterocyclic rings are optionally substituted by one or more $R^{27}$.

A heterocyclic ring formed by any of $R^{18}$ and $R^{19}$, $R^{20}$ and $R^{21}$, $R^{22}$ and $R^{23}$, $R^{18}$ and $R^{20}$, $R^{21}$ and $R^{22}$, and $R^{18}$ and $R^{22}$ contains for example one to three heteroatoms selected from O, S, and $N(R^{27})$.

Preferably $R^{18}$ and $R^{19}$, $R^{20}$ and $R^{21}$, and/or $R^{22}$ and $R^{23}$ may together form a saturated three- to six-membered alicyclic or heterocyclic ring wherein the aliyclic and heterocyclic rings are optionally substituted by one or more $R^{27}$; and/or $R^{18}$ and $R^{20}$ may together form a saturated or partially unsaturated four- to seven-membered alicyclic or heterocyclic ring wherein the aliyclic and heterocyclic rings are optionally substituted by one or more $R^{27}$; and/or $R^{18}$ and $R^{22}$ may together form a saturated or partially unsaturated four- to seven-membered alicyclic or heterocyclic ring wherein the aliyclic and heterocyclic rings are optionally substituted by one or more $R^{27}$; and where said heterocyclic rings preferably contain one or two heteroatoms selected from O, S and $NR^{27}$.

More preferably one or two of the pairs $R^{18}$ and $R^{19}$, $R^{20}$ and $R^{21}$, and/or $R^{22}$ and $R^{23}$ may together form a saturated three- to six-membered alicyclic or heterocyclic ring wherein the aliyclic and heterocyclic rings are optionally substituted by one or more $R^{27}$; or $R^{18}$ and $R^{20}$ may together form a saturated or partially unsaturated four- to seven-membered alicyclic or heterocyclic ring wherein the aliyclic and heterocyclic rings are optionally substituted by one or more $R^{27}$; or $R^{18}$ and $R^{22}$ may together form a saturated or partially unsaturated four- to seven-membered alicyclic or heterocyclic ring wherein the aliyclic and heterocyclic rings are optionally substituted by one or more $R^{27}$; and where said heterocyclic rings preferably contain one heteroatom selected from O, S and $NR^{27}$.

Even more preferably one or two of the pairs $R^{18}$ and $R^{19}$, $R^{20}$ and $R^{21}$, and/or $R^{22}$ and $R^{23}$ may together form a saturated three- to six-membered alicyclic ring wherein one of the ring members is optionally replaced by O, S, $NH(C_1$-$C_4$alkyl), $NH(C_1$-$C_4$alkoxy), and wherein the alicyclic ring is optionally substituted by one to five groups selected from halogen, methyl and halomethyl; or $R^{18}$ and $R^{20}$ may together form a saturated four- to seven-membered alicyclic ring optionally substituted by one to five groups independently selected from halogen, methyl and halomethyl; or $R^{18}$ and $R^{22}$ may together form a saturated four- to seven-membered alicyclic ring optionally substituted by one to five groups independently selected from halogen, methyl and halomethyl.

Each $R^{24}$ and $R^{25}$ independently are hydrogen, $C_1$-$C_8$alkyl, $C_1$-$C_8$haloalkyl, $C_2$-$C_8$alkenyl, $C_1$-$C_8$haloalkenyl, $C_2$-$C_8$alkynyl, $C_2$-$C_8$haloalkynyl, $C_3$-$C_8$cycloalkyl, $C_3$-$C_8$halocycloalkyl, $C_1$-$C_8$alkoxy, $C_1$-$C_8$haloalkoxy, $C_1$-$C_8$alkylcarbonyl, $C_1$-$C_8$haloalkylcarbonyl, $C_1$-$C_8$alkylsulfonyl, $C_1$-$C_8$haloalkylsulfonyl, amino, $NH(C_1$-$C_8$alkyl), $N(C_1$-$C_8$alkyl)$_2$, aryl or heterocycyl, wherein aryl and heterocyclyl are optionally substituted by one or more $R^{27}$;

Preferably each $R^{24}$ and $R^{25}$ independently are hydrogen, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_8$cycloalkyl, $C_3$-$C_8$halocycloalkyl, $C_1$-$C_8$alkoxy, $C_1$-$C_8$haloalkoxy, $C_1$-$C_8$alkylcarbonyl, $C_1$-$C_8$haloalkylcarbonyl, $C_1$-$C_8$alkylsulfonyl or $C_1$-$C_8$haloalkylsulfonyl, amino, $NH(C_1$-$C_8$alkyl), $N(C_1$-$C_8$alkyl)$_2$, phenyl or heterocycyl, wherein phenyl and heterocyclyl are optionally substituted by one or more $R^{27}$ and wherein each heterocycle is independently selected from pyrrolidinyl, pryollyl, imidazolyl, triazolyl, piperazinyl, piperidinyl, morpholinyl, pyridyl, pyrazinyl, pyridazinyl and pyrimidinyl.

More preferably each $R^{24}$ and $R^{25}$ independently are hydrogen, $C_1$-$C_8$alkyl, $C_2$-$C_8$alkenyl, $C_2$-$C_8$alkynyl, $C_3$-$C_8$cycloalkyl, $C_1$-$C_8$alkoxy, $C_1$-$C_8$alkylcarbonyl, $NH(C_1$-$C_8$alkyl), $N(C_1$-$C_8$alkyl)$_2$, phenyl, or a group selected from B1-B4

B1

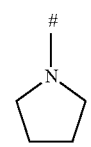

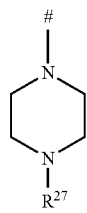

B2

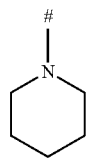

B3

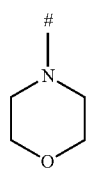

B4 wherein the phenyl and B1-B4 are optionally substituted by one or more $R^{27}$.

Even more preferably each $R^{24}$ and $R^{25}$ independently are hydrogen, $C_1$-$C_4$alkyl, $C_3$-$C_6$cycloalkyl, $C_1$-$C_4$alkoxy, $NH(C_1$-$C_4$alkyl), $N(C_1$-$C_4$alkyl)$_2$, phenyl, B1 or B3, wherein phenyl and groups B1 and B3 are optionally substituted by one to five groups independently selected from halogen, methyl and halomethyl.

Each $R^{26}$ is independently, halogen, cyano, amino, nitro, hydroxyl, mercapto, $C_1$-$C_8$ alkyl, $C_2$-$C_8$alkenyl, $C_2$-$C_8$alkynyl, $C_3$-$C_8$cycloalkyl, $C_3$-$C_8$cycloalkyl-$C_1$-$C_4$alkyl, $C_3$-$C_8$cycloalkyl-$C_1$-$C_4$alkyloxy, $C_3$-$C_8$cycloalkyl-$C_1$-$C_4$alkylthio, $C_1$-$C_8$alkoxy, $C_3$-$C_8$cycloalkyloxy, $C_2$-$C_8$alkenyloxy, $C_2$-$C_8$alkynyloxy, $C_1$-$C_8$alkylthio, $C_1$-$C_8$alkylsulfonyl, $C_1$-$C_8$alkylsulfinyl, $C_3$-$C_8$cycloalkylthio, $C_3$-$C_8$cycloalkylsulfonyl, $C_3$-$C_8$cycloalkylsulfinyl, aryl, aryloxy, arylthio, arylsulfonyl, arylsulfinyl, aryl-$C_1$-$C_4$alkyl, aryl-$C_1$-$C_4$alkyloxy, aryl-$C_1$-$C_4$alkylthio, heterocyclyl, heterocycyl-$C_1$-$C_4$alkyl, heterocyl-$C_1$-$C_4$alkyloxy, heterocycyl-$C_1$-$C_4$alkylthio, $NH(C_1$-$C_8$alkyl), $N(C_1$-$C_8$alkyl)$_2$, $C_1$-$C_4$alkylcarbonyl, $C_3$-$C_8$cycloalkylcarbonyl, $C_2$-$C_8$alkenylcarbonyl, $C_2$-$C_8$alkynylcarbonyl, wherein alkyl, alkenyl, alkynyl, cycloalkyl, alkoxy, alkenyloxy, alkynyloxy and cycloalkoxy are optionally substituted by halogen, and wherein the aryl and heterocyclyl are optionally substituted by one or more $R^{27}$.

Preferably each $R^{26}$ independently is halogen, cyano, amino, nitro, hydroxyl, mercapto, $C_1$-$C_8$ alkyl, $C_2$-$C_8$alkenyl, $C_2$-$C_8$alkynyl, $C_3$-$C_8$cycloalkyl, $C_3$-$C_8$cycloalkyl-$C_1$-$C_4$alkyl, $C_3$-$C_8$cycloalkyl-$C_1$-$C_4$alkylthio, $C_1$-$C_8$alkoxy, $C_3$-$C_8$cycloalkyloxy, $C_2$-$C_8$alkenyloxy, $C_2$-$C_8$alkynyloxy, $C_1$-$C_8$alkylthio, $C_1$-$C_8$alkylsulfonyl, $C_1$-$C_8$alkylsulfinyl, $C_3$-$C_8$cycloalkylthio, $C_3$-$C_8$cycloalkylsulfonyl, $C_3$-$C_8$cycloalkylsulfinyl, phenyl, phenyloxy, phenylthio, phenylsulfonyl, phenylsulfinyl, phenyl-$C_1$-$C_4$alkyl, phenyl-$C_1$-$C_4$alkyloxy, phenyl-$C_1$-$C_4$alkylthio, heterocyclyl, heterocycyl-$C_1$-$C_4$alkyl, heterocycyl-$C_1$-$C_4$alkyloxy, heterocycyl-$C_1$-$C_4$alkylthio, $NH(C_1$-$C_8$alkyl), $N(C_1$-$C_8$alkyl)$_2$, $C_1$-$C_4$alkylcarbonyl, $C_3$-$C_8$cycloalkylcarbonyl, $C_2$-$C_8$alkenylcarbonyl, $C_2$-$C_8$alkynylcarbonyl, wherein alkyl, alkenyl, alkynyl, cycloalkyl, alkoxy, alkenyloxy, alkynyloxy and cycloalkoxy are optionally substituted by halogen, and wherein aryl and heterocyclyl are optionally substituted by one or more $R^{27}$; and wherein heterocyclyl is independently selected from pyridyl, pyrazinyl, pyridazinyl, pyrimidinyl, pyrrolyl, pyrazolyl, imidazolyl, triazolyl, furanyl, thienyl, thiazolyl, thiadiazolyl, pyrrolidinyl, piperazinyl, piperidinyl, morpholinyl, and tetrahydropyranyl.

More preferably each $R^{26}$ independently is halogen, cyano, amino, mercapto, $C_1$-$C_8$alkyl, $C_3$-$C_8$cycloalkyl, $C_3$-$C_8$cycloalkyl-$C_1$-$C_4$alkyloxy, $C_3$-$C_8$cycloalkyl-$C_1$-$C_4$alkylthio, $C_1$-$C_8$alkoxy, $C_1$-$C_8$alkylthio, phenyl, phenyloxy, phenylthio, phenyl-$C_1$-$C_4$alkoxy, phenyl-$C_1$-$C_4$alkylthio, heterocyclyl, heterocyclyl-$C_1$-$C_4$alkoxy, heterocyclyl-$C_1$-$C_4$alkylthio, $NH(C_1$-$C_8$alkyl), $N(C_1$-$C_8$alkyl)$_2$, and wherein heterocyclyl is independently selected from pyridyl, pyrazinyl, pyridazinyl, pyrimidinyl, pyrrolyl, pyrazolyl, imidazolyl, triazolyl, furanyl, thienyl, thiazolyl, thiadiazolyl, pyrrolidinyl, piperazinyl, piperidinyl, morpholinyl, and tetrahydroyranyl, and wherein alkyl, cycloalkyl and alkoxy are optionally substituted by halogen, and wherein aryl and heterocyclyl moieties are optionally substituted by one or more $R^{27}$.

Even more preferably each $R^{26}$ independently is halogen, cyano, amino, mercapto, $C_4$alkyl, $C_3$-$C_6$cycloalkyl, $C_3$-$C_8$cycloalkyl-$C_1$-$C_4$alkylthio, $C_1$-$C_4$alkoxy, $C_1$-$C_4$alkylthio, phenyl and phenyloxy, and wherein alkyl, cycloalkyl and alkoxy are optionally substituted by halogen, and wherein phenyl is optionally substituted by one or more $R^{27}$.

Each $R^{27}$ is independently halogen, cyano, $C_1$-$C_4$alkyl, $C_1$-$C_4$haloalkyl, $C_1$-$C_4$alkoxy or $C_1$-$C_4$haloalkoxy, preferably halogen, cyano, methyl, halomethyl, methoxy or halomethoxy, more preferably halogen, methyl or halomethyl.

Each $R^{28}$ independently is $C_1$-$C_8$alkyl or $C_1$-$C_6$alkoxy, preferably methyl or methoxy.

Each $R^{29}$ independently is halogen, hydroxyl, cyano, mercapto, nitro, $C_1$-$C_4$alkyl, $C_1$-$C_4$haloalkyl, $C_1$-$C_4$alkoxy, $C_1$-$C_4$haloalkoxy, $C_1$-$C_4$alkylthio, $N(R^{30})_2$, phenyl or heteroaryl, wherein phenyl and heteroaryl are optionally substituted by one or more substituents independently selected from halogen, cyano, $C_1$-$C_4$ alkyl, $C_1$-$C_4$ haloalkyl, $C_1$-$C_4$ alkoxy and $C_1$-$C_4$ haloalkoxy. Preferably each $R^{29}$ independently is halogen, hydroxyl, cyano, nitro, $C_1$-$C_4$alkyl, $C_1$-$C_4$haloalkyl, $C_1$-$C_4$alkoxy, $C_1$-$C_4$haloalkoxy, $C_1$-$C_4$alkylthio, $N(R^{30})_2$, phenyl, pyridyl, pyrazinyl, pyridazinyl or pyrimidinyl, wherein the phenyl, pyridyl, pyrazinyl, pyridazinyl and pyrimidinyl are optionally substituted with one to three substituents independently selected from halogen, cyano, $C_1$-$C_4$ alkyl, $C_1$-$C_4$ haloalkyl, $C_1$-$C_4$ alkoxy and $C_1$-$C_4$ haloalkoxy. More preferably each $R^{29}$ independently is halogen, hydroxyl, cyano, nitro, $C_1$-$C_4$alkyl, $C_1$-$C_4$haloalkyl, $C_1$-$C_4$alkoxy, $C_1$-$C_4$haloalkoxy, $N(R^{30})_2$, phenyl or pyridyl, wherein phenyl and pyridyl are optionally substituted with 1 to 3 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy. Even more preferably each $R^{29}$ independently is halogen, hydroxyl, cyano, nitro, $C_1$-$C_4$alkyl, $C_1$-$C_4$haloalkyl, $C_1$-$C_4$alkoxy, $C_1$-$C_4$haloalkoxy, $N(R^{30})_2$, phenyl or pyridyl, wherein phenyl and pyridyl are optionally substituted with one to three substituents independently selected from halogen, cyano, methyl, halomethyl, methoxy and halomethoxy. Yet more preferably each $R^{29}$ independently is halogen, hydroxyl, cyano, $C_1$-$C_4$alkyl, $C_1$-$C_4$haloalkyl, $C_1$-$C_4$haloalkoxy or $N(R^{30})_2$. Yet more preferably each $R^{29}$ independently is halogen, hydroxyl, methyl, halomethyl, methoxy, halomethoxy, cyano, or $N(R^{30})_2$. Most preferably each $R^{29}$ independently is halogen, hydroxyl, cyano, or $N(R^{30})_2$.

Each $R^{30}$ independently is hydrogen, cyano, $C_1$-$C_4$alkyl, $C_1$-$C_4$alkylcarbonyl, $C_4$haloalkylcarbonyl, $C_1$-$C_4$alkylsulfonyl or $C_1$-$C_4$haloalkylsulfonyl, preferably hydrogen, $C_1$-$C_4$alkyl or $C_1$-$C_4$alkylcarbonyl, more preferably hydrogen or $C_1$-$C_4$alkyl.

e is 1 or 2, preferably 1.

q is 1, 2, or 3, preferably 1 or 2, preferably 1.

m is 0 or 1, providing that (in all compounds of the invention) when m is 1, $X^1$ and $X^2$ cannot both be oxygen. Preferably m is 1.

Preferably the group (A) is selected from A1 to A19

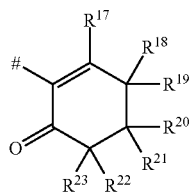
A1

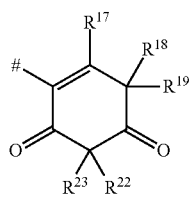
A2

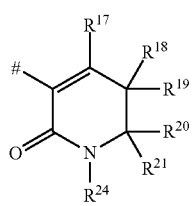
A3

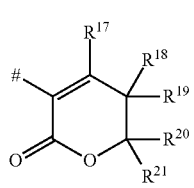
A4

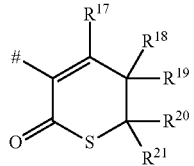
A5

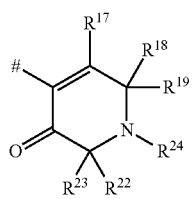
A6

-continued

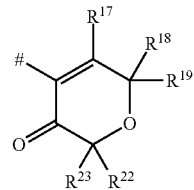
A7

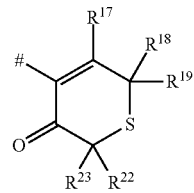
A8

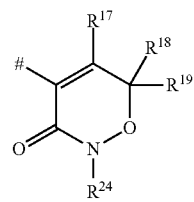
A9

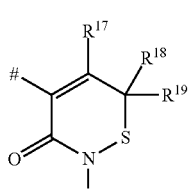
A10

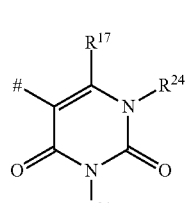
A11

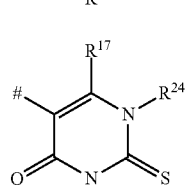
A12

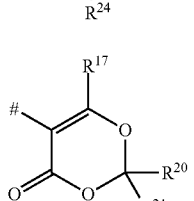
A13

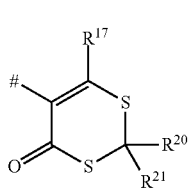
A14

-continued
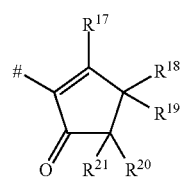 A15
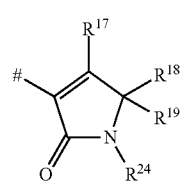 A16
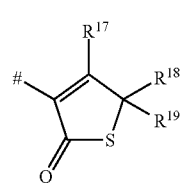 A17
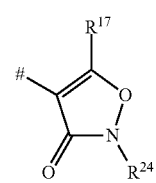 A18
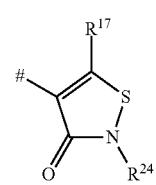 A19
$R^{18}$, $R^{19}$, $R^{20}$, $R^{21}$, $R^{22}$ and $R^{23}$ may form alicyclic and/or heterocyclic rings as described above. Examples of group (A) in such cases include, but are not limited to the following
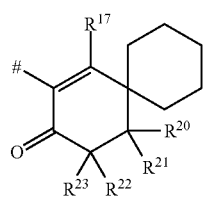 A1a
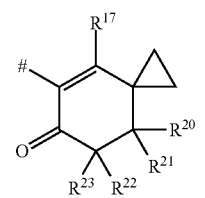 A1b
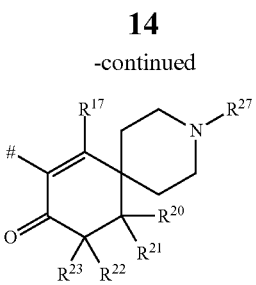 A1c
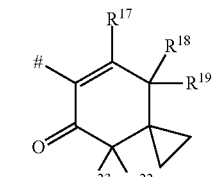 A1d
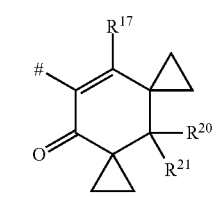 A1e
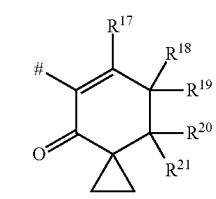 A1f
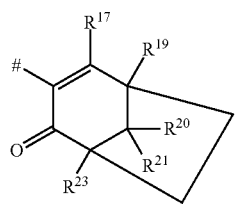 A1g
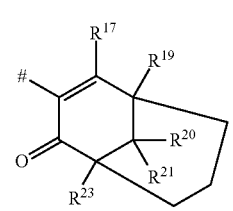 A1h
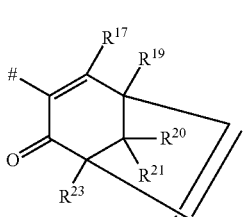 A1i
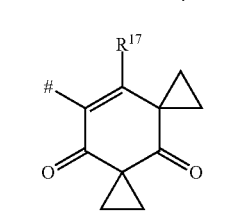 A2a

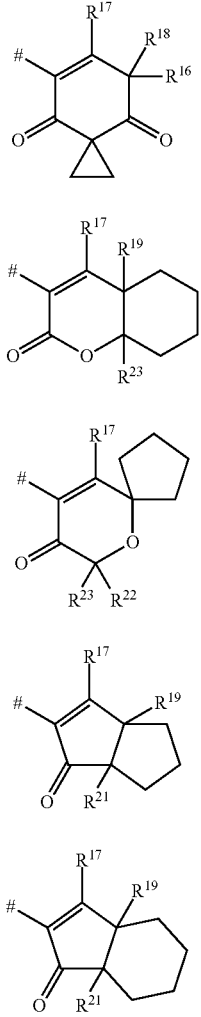

A2b

A4a

A7a

A15a

A15b

The compound of the invention may be a compound wherein group (A) is selected from A1 to A19, wherein A1 is selected from A1a-A1i, A2 is selected from A2a and A2b, A4 is A4a, A7 is A7a and A15 is selected from A15a and A15b, and wherein $R^{18}$, $R^{19}$, $R^{20}$, $R^{21}$, $R^{22}$ and $R^{23}$ each independently are hydrogen, halogen, hydroxyl, amino, cyano, $C_1$-$C_8$alkyl, $C_2$-$C_8$alkenyl, $C_2$-$C_8$alkynyl, $C_3$-$C_8$cycloalkyl, $C_1$-$C_8$alkoxy, $C_1$-$C_8$alkylthio, $C_1$-$C_8$alkylsulfonyl, $C_8$alkylsulfinyl, aryl, heteroaryl or $NHR^{25}$, wherein the alkyl, alkenyl, alkynyl, cycloalkyl, alkoxy, aryl and heteroaryl are optionally substituted by one or more $R^{26}$.

In one group of compounds of the invention:

G is O or S; T is $CR^{13}$ or N; $Y^1$, $Y^2$, $Y^3$ and $Y^4$ are independently $CR^{14}$ or N;

Q is —C(=O)-z, —C(=O)—O-z, —C(=O)—N($R^{15}$)-z or —C(=S)—N($R^{16}$)-z, in each case z indicates the bond that is connected to $R^{12}$; n is 1 or 2; p is 1; $R^1$, $R^2$, $R^3$, $R^4$, $R^5$, $R^6$, $R^7$, $R^8$, $R^9$, $R^{10}$, $R^{13}$ and $R^{14}$ each independently are hydrogen, halogen, cyano, $C_1$-$C_4$alkyl or $C_1$-$C_4$haloalkyl; $R^{11}$, $R^{15}$ and $R^{16}$ each independently are hydrogen, $C_1$-$C_4$alkyl, $C_3$-$C_5$cycloalkyl or $C_1$-$C_4$alkoxy; $R^{12}$ is aryl, heteroaryl, arylalkyl, a group (A) or a group (B):

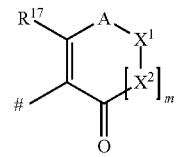

(A)

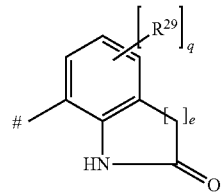

(B)

wherein the aryl or heteroaryl can be optionally substituted with 1 to 3 $R^{29}$; A is $C(R^{18}R^{19})$, C(=O), $NR^{24}$, O or S; $X^1$ is $C(R^{20}R^{21})$, C(=O), $NR^{24}$, O or S; $X^2$ is $C(R^{22}R^{23})$, C(=O), $NR^{24}$, O or S; each $R^{24}$ independently is hydrogen, cyano, $C_1$-$C_4$alkyl, $C_1$-$C_4$alkylcarbonyl, $C_1$-$C_4$alkylsulfonyl or $C_1$-$C_4$haloalkylsulfonyl; $R^{17}$ is hydroxyl, $O^-M^+$, amino or $NHR^{25}$; $M^+$ is a metal cation or ammonium cation, $R^{18}$, $R^{19}$, $R^{20}$, $R^{21}$, $R^{22}$ and $R^{23}$ each independently are hydrogen, halogen, hydroxyl, cyano, $C_1$-$C_4$alkyl, $C_3$-$C_5$cycloalkyl, $C_1$-$C_4$haloalkyl, $C_4$alkoxy, $C_1$-$C_4$haloalkoxy, $C_1$-$C_4$alkylthio, aryl, heteroaryl or $NHR^{25}$; and wherein $R^{18}$ and $R^{19}$, $R^{20}$ and $R^{21}$, and/or $R^{22}$ and $R^{23}$ may together form a saturated three- to six-membered alicyclic or heterocyclic ring; and/or $R^{18}$ and $R^{20}$ and/or $R^{21}$ and $R^{22}$ may together form a saturated four- to seven-membered alicyclic or heterocyclic ring; and/or $R^{18}$ and $R^{22}$ may together form a saturated four- to seven-membered alicyclic or heterocyclic ring;

each $R^{29}$ independently is halogen, hydroxyl, cyano, nitro, $C_1$-$C_4$alkyl, $C_1$-$C_4$haloalkyl, $C_1$-$C_4$alkoxy, $C_1$-$C_4$haloalkoxy, $C_1$-$C_4$alkylthio or $N(R^{30})_2$; each $R^{24}$, $R^{25}$ and $R^{30}$ independently are hydrogen, cyano, $C_1$-$C_4$alkyl, $C_1$-$C_4$alkylcarbonyl, $C_1$-$C_4$alkylsulfonyl or $C_1$-$C_4$haloalkylsulfonyl; m is 0 or 1; and e is 1 or 2.

In another group of compounds of the invention:

G is O; T is $CR^{13}$ or N; $Y^1$, $Y^2$, $Y^3$ and $Y^4$ are independently $CR^{14}$ or N; Q is —C(=O)-z, —C(=O)—O-z, —C(=O)—N($R^{15}$)-z or —C(=S)—N($R^{16}$)-z, in each case z indicates the bond that is connected to $R^{12}$; n is 1 or 2; p is 1; $R^1$, $R^2$, $R^3$, $R^4$, $R^5$, $R^6$, $R^7$, $R^8$, $R^9$, $R^{10}$, $R^{13}$ and $R^{14}$ each independently are hydrogen, halogen, $C_1$-$C_4$alkyl or $C_1$-$C_4$haloalkyl; $R^{11}$, $R^{15}$ and $R^{16}$ each independently are hydrogen, $C_1$-$C_4$alkyl; $R^{12}$ is aryl, heteroaryl, a group (A) or a group (B), wherein the aryl or heteroaryl can be optionally substituted with 1 to 3 $R^{29}$; each $R^{24}$ independently being hydrogen, $C_1$-$C_4$alkyl, $C_1$-$C_4$alkylcarbonyl, $C_1$-$C_4$alkylsulfonyl or $C_1$-$C_4$haloalkylsulfonyl; A is $C(R^{18}R^{19})$, C(=O), $NR^{24}$ or O; $X^1$ is $C(R^{20}R^{21})$, C(=O), $NR^{24}$ or O;

$X^2$ is $C(R^{22}R^{23})$, C(=O), $NR^{24}$ or O; $R^{17}$ is hydroxyl, $O^-M^+$, or $NHR^{25}$; $M^+$ is a metal cation or ammonium cation; $R^{18}$, $R^{19}$, $R^{20}$, $R^{21}$, $R^{22}$ and $R^{23}$ each independently are hydrogen, halogen, cyano, $C_1$-$C_4$alkyl, $C_3$-$C_5$cycloalkyl, $C_1$-$C_4$haloalkyl, $C_1$-$C_4$alkoxy, $C_1$-$C_4$alkylthio, aryl, heteroaryl or $NHR^{25}$; and wherein $R^{18}$ and $R^{19}$, $R^{20}$ and $R^{21}$, and/or $R^{22}$ and $R^{23}$ may together form a saturated three- to six-membered alicyclic or heterocyclic ring; each $R^{29}$ independently is halogen, hydroxyl, cyano, nitro, $C_1$-$C_4$alkyl, $C_1$-$C_4$haloalkyl, $C_1$-$C_4$alkoxy, $C_1$-$C_4$haloalkoxy or $N(R^{30})_2$; each $R^{24}$, $R^{25}$ and $R^{30}$ independently is hydrogen, $C_1$-$C_4$alkyl, $C_1$-$C_4$alkylcarbonyl, $C_1$-$C_4$alkylsulfonyl or $C_1$-$C_4$haloalkylsulfonyl; e is 1 or 2; and m is 0 or 1.

In another group of compounds of the invention:

G is O; T is CH or N; $Y^1$, $Y^2$, $Y^3$ and $Y^4$ are independently CH or N; Q is —C(=O)-z, —C(=O)—O-z, —C(=O)—N($R^{15}$)-z, in each case z indicates the bond that is connected to $R^{12}$; n is 1 or 2; p is 1; $R^1$, $R^2$, $R^3$, $R^4$, $R^5$, $R^6$, $R^7$, $R^8$, $R^9$, $R^{10}$, $R^{13}$ and $R^{14}$ each independently are hydrogen, chloro, methyl or trifluoromethyl; $R^{11}$, $R^{15}$ and $R^{16}$ each independently are hydrogen or methyl; $R^{12}$ is phenyl, thienyl, thiadiazolyl, pyridyl, pyrimidinyl or pyridazinyl, a group (A) or a group (B), wherein the phenyl or thienyl, thiadiazolyl, pyridyl, pyrimidinyl or pyridazinyl, can be optionally substituted with 1 to 3 $R^{29}$; A is $C(R^{18}R^{19})$, C(=O), NH, $NCH_3$ or O; $X^1$ is $C(R^{20}R^{21})$, C(=O), NH, $NCH_3$ or O; $X^2$ is $C(R^{22}R^{23})$, C(=O), NH, $NCH_3$ or O; $R^{17}$ is hydroxyl, $O^-M^+$; $M^+$ is a metal cation or ammonium cation; $R^{18}$, $R^{19}$, $R^{20}$, $R^{21}$, $R^{22}$ and $R^{23}$ each independently are hydrogen, fluoro, cyano, methyl, ethyl, cyclopropyl, cyclobutyl, trifluoromethyl, methoxy, methylthio, phenyl or pyridyl; and wherein $R^{18}$ and $R^{19}$, $R^{20}$ and $R^{21}$, and/or $R^{22}$ and $R^{23}$ may together form a cyclopropyl or a cyclobutyl ring; each $R^{29}$ independently is halogen, hydroxyl, cyano, nitro, $C_1$-$C_4$alkyl, $C_1$-$C_4$haloalkyl, $C_1$-$C_4$alkoxy, $C_1$-$C_4$haloalkoxy or $N(R^{30})_2$; each $R^{30}$ independently is hydrogen, $C_1$-$C_4$alkylsulfonyl or $C_1$-$C_4$haloalkylsulfonyl; e is 1 or 2; and m is 1.

In another group of compounds of the invention:

G is O; T is CH; $Y^1$, $Y^2$, $Y^3$ and $Y^4$ are independently CH or N; Q is —C(=O)-z, in each case z indicates the bond that is connected to $R^{12}$; n is 2; p is 1; $R^1$, $R^2$, $R^3$, $R^4$, $R^5$, $R^6$, $R^7$, $R^8$, $R^9$, $R^{10}$, $R^{13}$ and $R^{14}$ each independently are hydrogen, chloro, methyl or trifluoromethyl;

$R^{11}$, is hydrogen or methyl; $R^{12}$ is phenyl, thienyl, pyridyl, pyrimidinyl or pyridazinyl, a group (A), wherein the phenyl or thienyl, pyridyl, pyrimidinyl or pyridazinyl, can be optionally substituted with 1 to 3 $R^{29}$; A is $C(R^{18}R^{19})$, C(=O) or O; $X^1$ is $C(R^{20}R^{21})$, C(=O) or O; $X^2$ is $C(R^{22}R^{23})$, C(=O) or O; $R^{17}$ is hydroxyl or $O^-M^+$, where $M^+$ is a metal cation; $R^{18}$, $R^{19}$, $R^{20}$, $R^{21}$, $R^{22}$ and $R^{23}$ each independently are hydrogen, methyl, ethyl, cyclopropyl, trifluoromethyl, methoxy, methylthio or phenyl; and wherein $R^{18}$ and $R^{19}$, $R^{20}$ and $R^{21}$, and/or $R^{22}$ and $R^{23}$ may together form a cyclopropyl ring; each $R^{29}$ independently is halogen, hydroxyl, cyano, $C_1$-$C_4$alkyl, $C_1$-$C_4$haloalkyl, $C_1$-$C_4$haloalkoxy or $N(R^{30})_2$; each $R^{30}$ independently is hydrogen or $C_1$-$C_4$alkylsulfonyl; and m is 1.

In another group of compounds of the invention:

G is O; T is CH; $Y^1$, $Y^2$, $Y^3$ and $Y^4$ are independently CH or N; Q is —C(=O)-z, in each case z indicates the bond that is connected to $R^{12}$; n is 2; p is 1;

$R^1$ is trifluoromethyl; $R^2$ is methyl; $R^3$, $R^4$, $R^5$, $R^6$, $R^7$, $R^8$, $R^9$, $R^{10}$, $R^{13}$ and $R^{14}$ each independently are hydrogen; $R^{11}$ is hydrogen; $R^{12}$ is aryl, pyridyl, or group (A), wherein the phenyl or pyridyl, can be optionally substituted with 1 to 3 $R^{29}$; A is $C(R^{18}R^{19})$ or C(=O); $X^1$ is $C(R^{20}R^{21})$ or C(=O); $X^2$ is $C(R^{22}R^{23})$ or C(=O); $R^{17}$ is hydroxyl; $R^{18}$, $R^{19}$, $R^{20}$, $R^{21}$, $R^{22}$ and $R^{23}$ each independently are hydrogen, methyl, cyclopropyl or methylthio; and wherein $R^{18}$ and $R^{19}$, $R^{20}$ and $R^{21}$, and/or $R^{22}$ and $R^{23}$ may together form a cyclopropyl ring; each $R^{29}$ independently is halogen, hydroxyl, methyl, halomethyl, methoxy, halomethoxy, cyano, or $N(R^{30})_2$; each $R^{30}$ is independently hydrogen or $C_1$-$C_4$alkylsulfonyl; and m is 1.

In another group of compounds of the invention:

G is O; T is CH; $Y^1$, $Y^2$, $Y^3$ and $Y^4$ are independently CH or N; Q is —C(=O)-z, in each case z indicates the bond that is connected to $R^{12}$; n is 2; p is 1; $R^1$ is trifluoromethyl; $R^2$ is methyl;

$R^3$, $R^4$, $R^5$, $R^6$, $R^7$, $R^8$, $R^9$, $R^{10}$, $R^{13}$ and $R^{14}$ each independently are hydrogen; $R^{11}$ is hydrogen; $R^{12}$ is phenyl, benzyl, or group (A), wherein the phenyl and benzyl are optionally substituted by one or more $R^{29}$; and wherein group (A) is A1 or A2; $R^{17}$ is hydroxyl; $R^{18}$, $R^{19}$, $R^{20}$, $R^{21}$, $R^{22}$ and $R^{23}$ each independently are hydrogen, methyl, cyclopropyl or methylthio; and wherein $R^{18}$ and $R^{19}$, $R^{20}$ and $R^{21}$, and/or $R^{22}$ and $R^{23}$ may together form a cyclopropyl ring; each $R^{29}$ independently is halogen, hydroxyl, methyl, halomethyl, methoxy, halomethoxy, cyano, or $N(R^{30})_2$; each $R^{30}$ is independently hydrogen or $C_1$-$C_4$alkylsulfonyl;

and m is 1.

In one group of compounds of the invention $R^{12}$ is phenyl, benzyl, or group (A), wherein the phenyl and benzyl are optionally substituted by one or more $R^{29}$; and wherein group (A) is A1 or A2.

In one group of compounds $R^{12}$ is aryl, heteroaryl or group (A) and the aryl or heteroaryl is substituted by hydroxyl and optionally substituted by one or two further substituents. Preferably the hydroxyl is at the ortho position.

For the avoidance of doubt, when n is 1 and p is 1 compounds of formula I have the formula according to formula I-A:

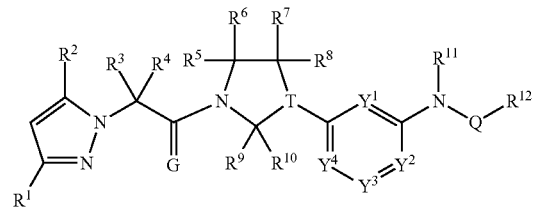

(I-A)

in which T, $Y^1$, $Y^2$, $Y^3$, $Y^4$, G, Q, $R^1$, $R^2$, $R^3$, $R^4$, $R^5$, $R^6$, $R^7$, $R^8$, $R^9$, $R^{10}$ $R^{11}$ and $R^{12}$ have the definitions as described for formula I.

When n is 2 and p is 1, compounds of formula I have the formula according to formula I-B:

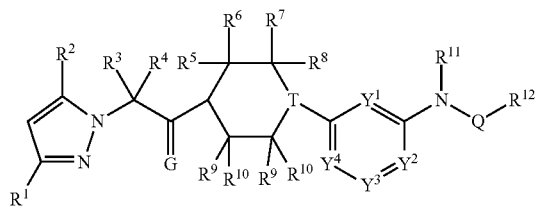

(I-B)

in which T, $Y^1$, $Y^2$, $Y^3$, $Y^4$, G, Q, $R^1$, $R^2$, $R^3$, $R^4$, $R^5$, $R^6$, $R^7$, $R^8$, $R^9$, $R^{10}$ $R^{11}$ and $R^{12}$ have the definitions as described for formula I.

When n is 1 and p is 2, compounds of formula I have the formula according to formula IC:

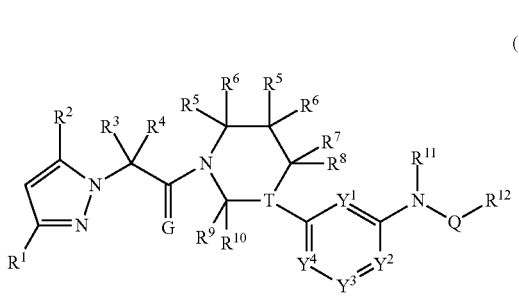

(I-C)

in which T, $Y^1$, $Y^2$, $Y^3$, $Y^4$, G, Q, $R^1$, $R^2$, $R^3$, $R^4$, $R^5$, $R^6$, $R^7$, $R^8$, $R^9$, $R^{10}$ $R^{11}$ and $R^{12}$ have the definitions as described for formula I.

The invention also relates to compounds of formula I-A, formula I-B, and formula I-C as shown above with preferred definitions of the substituents being the same as for compounds of formula I.

The invention also relates to compounds of formula I-D:

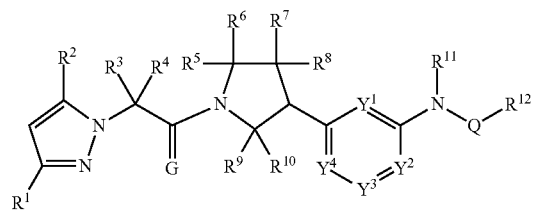

(I-D)

wherein $Y^1$, $Y^2$, $Y^3$, $Y^4$, G, Q, $R^1$, $R^2$, $R^3$, $R^4$, $R^5$, $R^6$, $R^7$, $R^8$, $R^9$, $R^{10}$ $R^{11}$ and $R^{12}$ have the definitions as described for formula I as defined above. Preferred definitions of $Y^1$, $Y^2$, $Y^3$, $Y^4$, G, Q, $R^1$, $R^2$, $R^3$, $R^4$, $R^5$, $R^6$, $R^7$, $R^8$, $R^9$, $R^{10}$ $R^{11}$ and $R^{12}$ are as defined above for compounds of formula I.

The invention also relates to compounds of formula I-E:

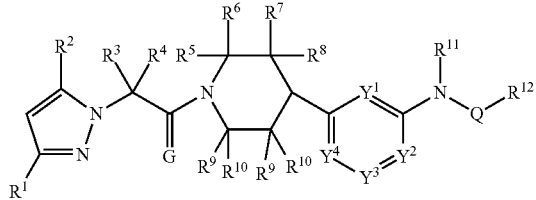

(I-E)

wherein $Y^1$, $Y^2$, $Y^3$, $Y^4$, A, Q, $R^1$, $R^2$, $R^3$, $R^4$, $R^5$, $R^6$, $R^7$, $R^8$, $R^9$, $R^{10}$ $R^{11}$ and $R^{12}$ have the definitions as described for formula I as defined above. Preferred definitions of $Y^1$, $Y^2$, $Y^3$, $Y^4$, A, Q, $R^1$, $R^2$, $R^3$, $R^4$, $R^5$, $R^6$, $R^7$, $R^8$, $R^9$, $R^{10}$ $R^{11}$ and $R^{12}$ are as defined above for compounds of formula I.

The invention also relates to a compound of formula I-F:

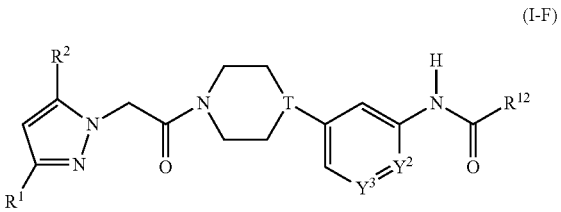

(I-F)

wherein T is N or CH;

$Y^2$ and $Y^3$ are both CH, or one of $Y^3$ and $Y^2$ is N and the other is CH; and $R^1$, $R^2$ and $R^{12}$ are as described for a compound of formula I as defined above. Preferred definitions of $R^1$, $R^2$ and $R^{12}$ are as defined for compounds of formula I.

The invention also relates to a compound of formula I-G:

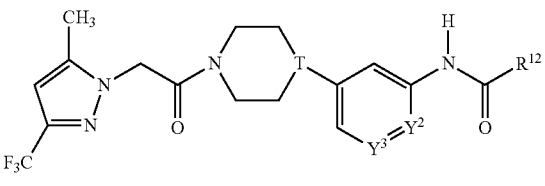

(I-G)

wherein T is N or CH;

$Y^2$ and $Y^3$ are both CH, or one of $Y^3$ and $Y^2$ is N and the other is CH; and $R^{12}$ is as described for a compound of formula I as defined above. Preferred definitions of $R^{12}$ are as defined for compounds of formula I.

The invention includes compounds of formula II.1:

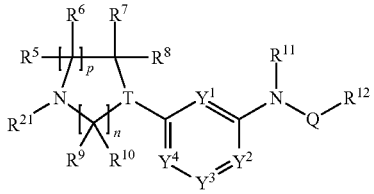

(II.1)

wherein $R^5$, $R^6$, $R^7$, $R^8$, $R^9$, $R^{10}$, $R^{11}$, $R^{12}$, Q, T, $Y^1$, $Y^2$, $Y^3$, $Y^4$, n and p are as defined for formula I and $R^{21}$ is hydrogen or a protecting group such as acetyl, benzyl or tert-butoxycarbonyl, or a salt or N-oxide thereof. These compounds, including salts and N-oxides thereof, are useful as intermediates in the synthesis of compounds of formula I. Preferred definitions of $R^5$, $R^6$, $R^7$, $R^8$, $R^9$, $R^{10}$, $R^{11}$, $R^{12}$, Q, T, $Y^1$, $Y^2$, $Y^3$, $Y^4$, n and p are as defined for compounds of formula I.

The invention also includes compound of formula III:

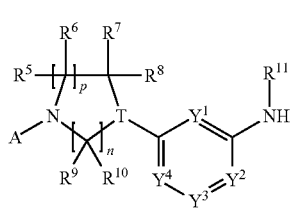
(III)

wherein A is hydrogen, a protecting group such as alkylcarbonyl, benzyl or alkoxycarbonyl, e.g. $C_1$-$C_4$ alkylcarbonyl, benzyl or $C_1$-$C_4$ alkoxycarbonyl, in particular acetyl, benzyl or tert-butoxycarbonyl; or group M

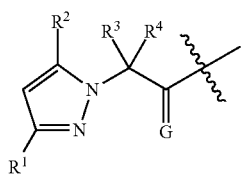
(M)

and $R^1$, $R^2$, $R^3$, $R^4$, $R^5$, $R^6$, $R^7$, $R^8$, $R^9$, $R^{10}$, $R^{11}$, G, T, $Y^1$, $Y^2$, $T^3$, $Y^4$, n and p are as defined for formula I, or a salt or N-oxide thereof. These compounds, including salts and N-oxides thereof, are useful as intermediates in the synthesis of compounds of formula I. Preferred definitions of $R^1$, $R^2$, $R^3$, $R^4$, $R^5$, $R^6$, $R^7$, $R^8$, $R^9$, $R^{10}$, $R^{11}$, $R^{12}$, G, T, $Y^1$, $Y^2$, $Y^3$, $Y^4$, n and p are as defined for formula I.

The invention also includes compounds of formula V:

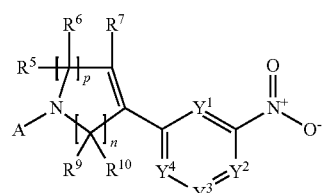
(V)

wherein A is hydrogen, a protecting group such as alkylcarbonyl, benzyl or alkoxycarbonyl, e.g. $C_1$-$C_4$ alkylcarbonyl, benzyl or $C_1$-$C_4$ alkoxycarbonyl, in particular acetyl, benzyl or tert-butoxycarbonyl; or group M

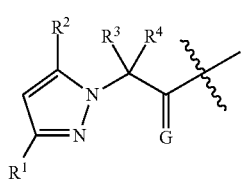
(M)

and $R^1$, $R^2$, $R^3$, $R^4$, $R^5$, $R^6$, $R^7$, $R^9$, $R^{10}$, G, $Y^1$, $Y^2$, $Y^3$, $Y^4$, or a salt or N-oxide thereof. These compounds, including salts and N-oxides thereof, are useful as intermediates in the synthesis of compounds of formula I. Preferred definitions of $R^1$, $R^2$, $R^3$, $R^4$, $R^5$, $R^6$, $R^7$, $R^9$, $R^{10}$, G, $Y^1$, $Y^2$, $Y^3$, $Y^4$, n and p are as defined for formula I.

The invention also includes compounds of formula VI:

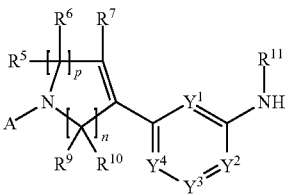
(VI)

wherein A is hydrogen, a protecting group such as alkylcarbonyl, benzyl or alkoxycarbonyl, e.g. $C_1$-$C_4$ alkylcarbonyl, benzyl or $C_1$-$C_4$ alkoxycarbonyl, in particular acetyl, benzyl or tert-butoxycarbonyl; or group M

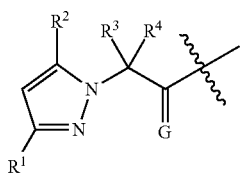
(M)

and $R^1$, $R^2$, $R^3$, $R^4$, $R^5$, $R^6$, $R^7$, $R^9$, $R^{10}$, $R^{11}$, $R^{12}$, G, $Y^1$, $Y^2$, $Y^3$, $Y^4$, n and p are as defined for formula I, or a salt or N-oxide thereof. These compounds, including salts and N-oxides thereof, are useful as intermediates in the synthesis of compounds of formula I. Preferred definitions of $R^1$, $R^2$, $R^3$, $R^4$, $R^5$, $R^6$, $R^7$, $R^9$, $R^{10}$, $R^{11}$, $R^{12}$, G, $Y^1$, $Y^2$, $Y^3$, $Y^4$, n and p are as defined for formula I.

The invention also includes compounds of formula IX:

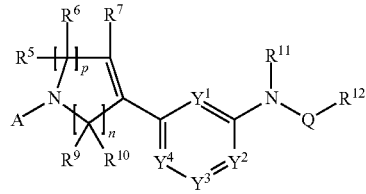
(IX)

wherein A is hydrogen, a protecting group such as alkylcarbonyl, benzyl or alkoxycarbonyl, e.g. $C_1$-$C_4$ alkylcarbonyl, benzyl or $C_1$-$C_4$ alkoxycarbonyl, in particular acetyl, benzyl or tert-butoxycarbonyl; or group M

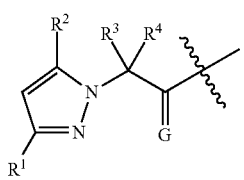
(M)

and $R^1$, $R^2$, $R^3$, $R^4$, $R^5$, $R^6$, $R^7$, $R^9$, $R^{10}$, $R^{11}$, $R^{12}$, G, Q, $Y^1$, $Y^2$, $Y^3$, $Y^4$, n and p are as defined for formula I. These compounds, including salts and N-oxides thereof, are useful as intermediates in the synthesis of compounds of formula I.

Preferred definitions of $R^1$, $R^2$, $R^3$, $R^4$, $R^5$, $R^6$, $R^7$, $R^9$, $R^{10}$, $R^{11}$, $R^{12}$, G, Q, $Y^1$, $Y^2$, $Y^3$, $Y^4$, n and p are as defined for formula I.

The invention also includes compounds of formula XIII:

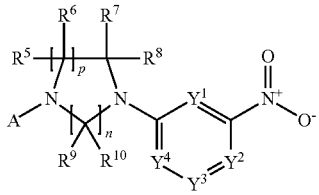

(XIII)

wherein A is hydrogen, a protecting group such as alkylcarbonyl, benzyl or alkoxycarbonyl, e.g. $C_1$-$C_4$ alkylcarbonyl, benzyl or $C_1$-$C_4$ alkoxycarbonyl, in particular acetyl, benzyl or tert-butoxycarbonyl; or group M

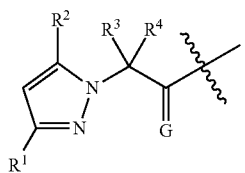

(M)

and $R^1$, $R^2$, $R^3$, $R^4$, $R^5$, $R^6$, $R^7$, $R^9$, $R^{10}$, G, $Y^1$, $Y^2$, $Y^3$, $Y^4$, n and p are as defined for formula I. These compounds, including salts and N-oxides thereof, are useful as intermediates in the synthesis of compounds of formula I. Preferred definitions of $R^1$, $R^2$, $R^3$, $R^4$, $R^5$, $R^6$, $R^7$, $R^8$, $R^9$, $R^{10}$, G, $Y^1$, $Y^2$, $Y^3$, $Y^4$, n and p are as defined for formula I.

Compounds of the present invention can be made as shown in the following schemes. Throughout this description, the group M, wherein $R^1$, $R^2$, $R^3$, $R^4$ and G are as defined for formula I, stands for:

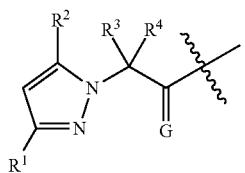

(M)

Compounds of formula (I) can be made as shown in the following schemes.

The compounds of formula II, wherein $R^5$, $R^6$, $R^7$, $R^8$, $R^9$, $R^{10}$, $R^{11}$, T, $Y^1$, $Y^2$, $Y^3$, $Y^4$, n, p, Q are as defined for formula I and A is hydrogen, a protecting group such as acetyl, benzyl or tert-butoxycarbonyl or a group M, can be obtained by transformation of a compound of formula III, wherein $R^5$, $R^6$, $R^7$, $R^8$, $R^9$, $R^{10}$, $R^{11}$, T, $Y^1$, $Y^2$, $Y^3$, $Y^4$, n, p are as defined for formula I and A is hydrogen, a protecting group such as acetyl, benzyl or tert-butoxycarbonyl or a group M, with a compound of formula IV, wherein $R^{12}$ and Q are as defined for formula I and X is a hydroxy, halogen, preferably fluoro, chloro or bromo or alkoxy, such as methoxy, ethoxy. This is shown in Scheme 1.

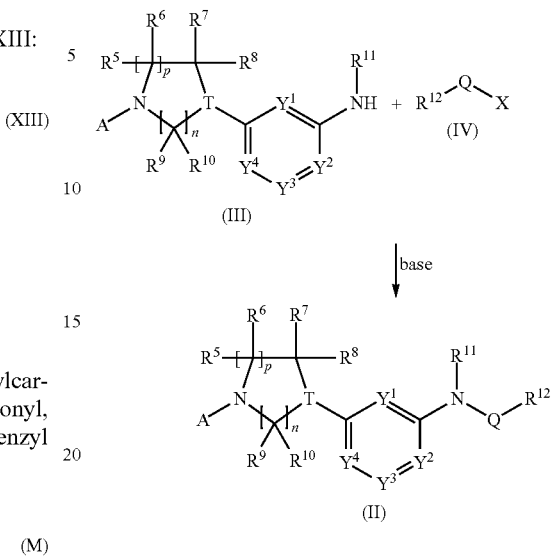

The compounds of formula III.1, wherein $R^5$, $R^6$, $R^7$, $R^8$, $R^9$, $R^{10}$, T, $Y^1$, $Y^2$, $Y^3$, $Y^4$, n, p are as defined for formula I and A is hydrogen, a protecting group such as acetyl, benzyl or tert-butoxycarbonyl or a group M can be obtained by reduction of a compound of formula V, wherein $R^5$, $R^6$, $R^7$, $R^9$, $R^{10}$, $Y^1$, $Y^2$, $Y^3$, $Y^4$, n, p are as defined for formula I and A is hydrogen, a protecting group such as acetyl, benzyl or tert-butoxycarbonyl or a group M, using hydrogen with a catalyst, such as palladium on charcoal, raney-nickel, etc. This is shown in Scheme 2.

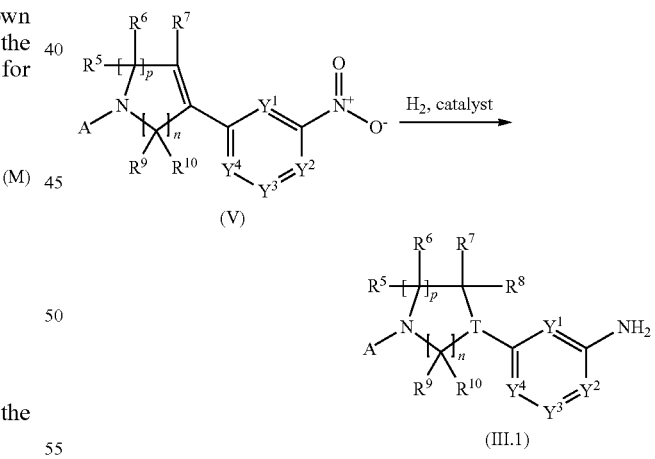

Alternatively, the compounds of formula III.1, wherein $R^5$, $R^6$, $R^7$, $R^8$, $R^9$, $R^{10}$, T, $Y^1$, $Y^2$, $Y^3$, $Y^4$, n, p are as defined for formula I and A is hydrogen, a protecting group such as acetyl, benzyl or tert-butoxycarbonyl or a group M can be obtained by reduction of a compound of formula VI.1, wherein $R^5$, $R^6$, $R^7$, $R^9$, $R^{10}$, $Y^1$, $Y^2$, $Y^4$, n, p are as defined for formula I and A is hydrogen, a protecting group such as acetyl, benzyl or tert-butoxycarbonyl or a group M, using hydrogen with a catalyst, such as palladium on charcoal, raney-nickel, etc. This is shown in Scheme 3.

Scheme 3

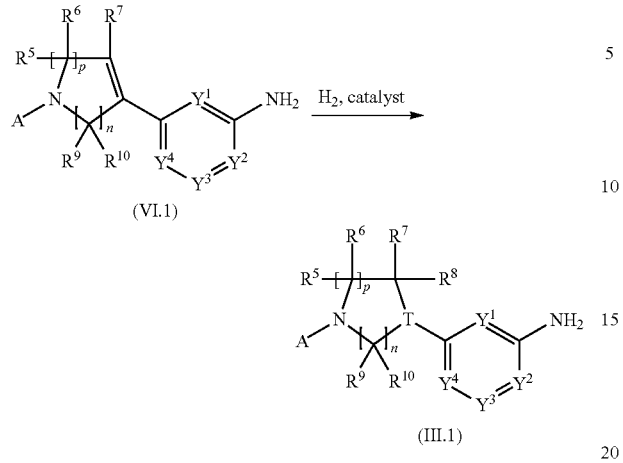

Scheme 5

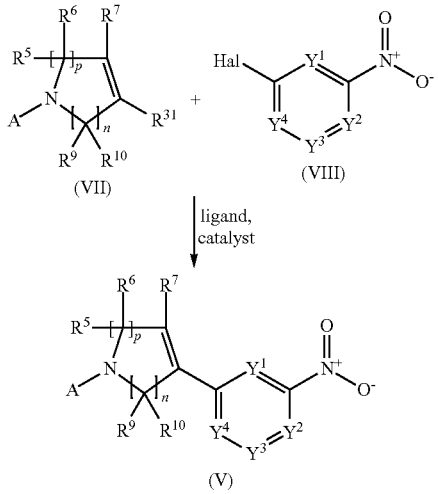

The compounds of formula VI.1, wherein $R^5$, $R^6$, $R^7$, $R^8$, $R^9$, $R^{10}$, T, $Y^1$, $Y^2$, $Y^3$, $Y^4$, n, p are as defined for formula I and A is hydrogen, a protecting group such as acetyl, benzyl or tert-butoxycarbonyl or a group M can be obtained by reduction of a compound of formula V, wherein $R^5$, $R^6$, $R^7$, $R^9$, $R^{10}$, $Y^1$, $Y^2$, $Y^3$, $Y^4$, n, p are as defined for formula I and A is hydrogen, a protecting group such as acetyl, benzyl or tert-butoxycarbonyl or a group M, using stannyl dichloride or zinc metal in acidic media or iron metal in acidic media. This is shown in Scheme 4.

Alternatively, the compounds of formula II, wherein $R^5$, $R^6$, $R^7$, $R^8$, $R^9$, $R^{10}$, $R^{11}$, T, $Y^1$, $Y^2$, $Y^3$, $Y^4$, n, p, Q are as defined for formula I and A is hydrogen, a protecting group such as acetyl, benzyl or tert-butoxycarbonyl or a group M, can be obtained by reduction of a compound of formula IX, wherein $R^5$, $R^6$, $R^7$, $R^9$, $R^{10}$, $R^{11}$, Q, $Y^1$, $Y^2$, $Y^3$, $Y^4$, n, p are as defined for formula I and A is hydrogen, a protecting group such as acetyl, benzyl or tert-butoxycarbonyl or a group M, using hydrogen with a catalyst, such as palladium on charcoal, raney-nickel, etc. This is shown in Scheme 6.

Scheme 4

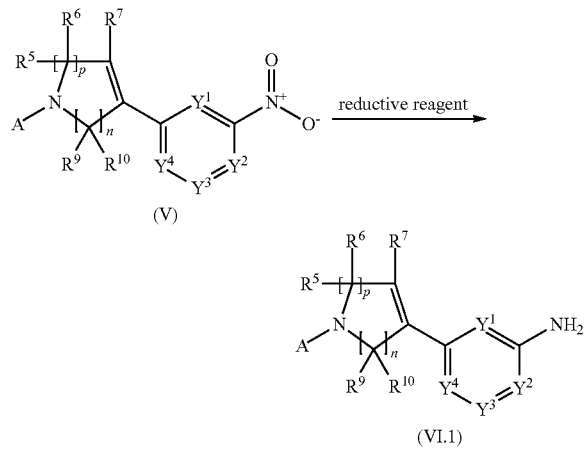

Scheme 6

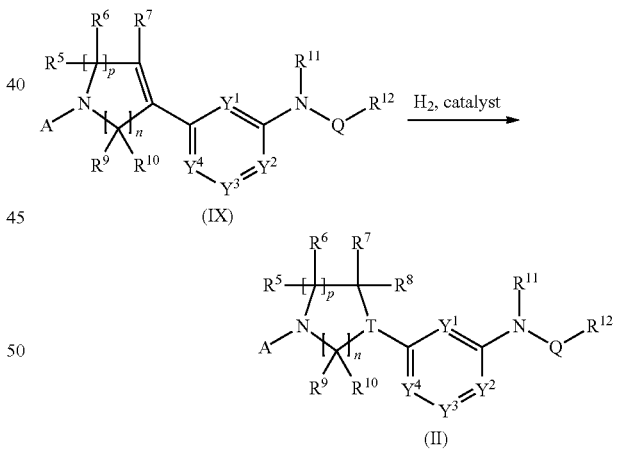

The compounds of formula V, wherein $R^5$, $R^6$, $R^7$, $R^9$, $R^{10}$, T, $Y^1$, $Y^2$, $Y^3$, $Y^4$, n, p are as defined for formula I and A is hydrogen, a protecting group such as acetyl, benzyl or tert-butoxycarbonyl or a group M, can be obtained by cross coupling of a compound of formula VII, wherein $R^5$, $R^6$, $R^7$, $R^9$, $R^{10}$, n, p are as defined for formula I and A is hydrogen, a protecting group such as acetyl, benzyl or tert-butoxycarbonyl or a group M, and $R^{31}$ is $B(OH)_2$ or $B(OR^{32})_2$, wherein $R^{32}$ is alkyl or cycloalkyl, with a compound of formula VIII, wherein $Y^1$, $Y^2$, $Y^3$, $Y^4$, are defined as in formula I, and Hal is halogen preferably chlorine, bromine or iodine, and a transition metal, such as bis-(triphenylphosphine)palladium(II) chloride. This is shown in Scheme 5.

The compounds of formula IX, wherein $R^5$, $R^6$, $R^7$, $R^9$, $R^{10}$, $R^{11}$, Q, $Y^1$, $Y^2$, $Y^3$, $Y^4$, n, p are as defined for formula I and A is hydrogen, a protecting group such as acetyl, benzyl or tert-butoxycarbonyl or a group M, can be obtained by transformation of a compound of formula VI, wherein $R^5$, $R^6$, $R^7$, $R^9$, $R^{10}$, $R^{11}$, $Y^1$, $Y^2$, $Y^3$, $Y^4$, n, p are as defined for formula I and A is hydrogen, a protecting group such as acetyl, benzyl or tert-butoxycarbonyl or a group M, with a compound of formula IV, wherein $R^{12}$ and Q are as defined for formula I and $R^{33}$ is hydroxy, halogen, preferably fluoro, chloro or bromo or alkoxy, such as methoxy, ethoxy. This is shown in Scheme 7.

Scheme 7

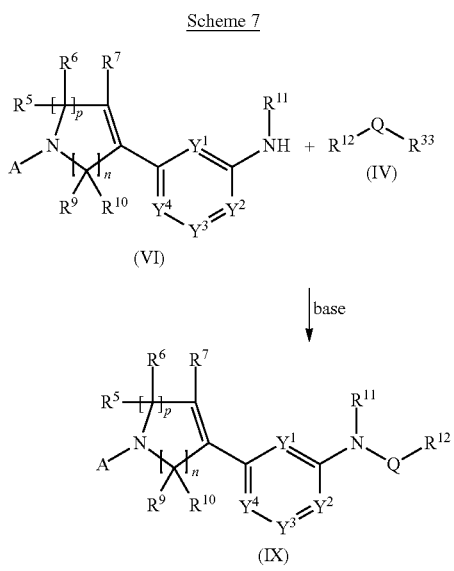

Alternatively, the compounds of formula VI.1, wherein $R^5$, $R^6$, $R^7$, $R^9$, $R^{10}$, $Y^1$, $Y^2$, $Y^3$, $Y^4$, n, p are as defined for formula I and A is hydrogen, a protecting group such as acetyl, benzyl or tert-butoxycarbonyl or a group M, can be obtained by cross coupling of a compound of formula VII, wherein $R^5$, $R^6$, $R^7$, $R^9$, $R^{10}$, n, p are as defined for formula I and A is hydrogen, a protecting group such as acetyl, benzyl or tert-butoxycarbonyl or a group M, and $R^{31}$ is B(OH)$_2$ or B(OR$^{32}$)$_2$, wherein $R^{32}$ is alkyl or cycloalkyl, with a compound of formula X, wherein $Y^1$, $Y^2$, $Y^3$, $Y^4$, are as defined for formula I, and Hal is halogen preferably chlorine, bromine or iodine. This is shown in Scheme 8.

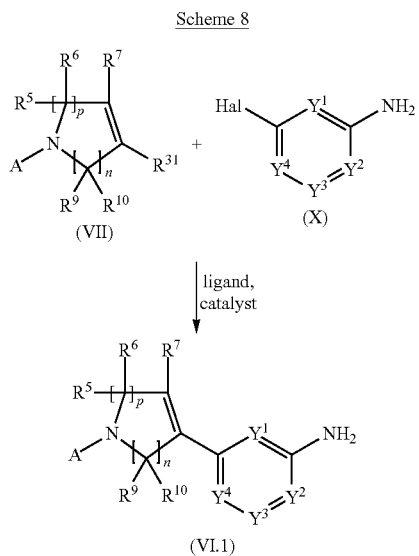

The compounds of formula XIII, wherein $R^5$, $R^6$, $R^7$, $R^8$, $R^{10}$, $Y^1$, $Y^2$, $Y^3$, $Y^4$, n, p are as defined for formula I and A is hydrogen, a protecting group such as acetyl, benzyl or tert-butoxycarbonyl or a group M, can be obtained by transformation of a compound of formula XII, wherein $R^5$, $R^6$, $R^7$, $R^8$, $R^9$, $R^{10}$, n, p are as defined for formula I and A is hydrogen, a protecting group such as acetyl, benzyl or tert-butoxycarbonyl or a group M, with a compound of formula XI, wherein $Y^1$, $Y^2$, $Y^3$, $Y^4$ are as defined for formula I, and Hal is halogen, preferably iodo, bromo, chloro or fluoro. This is shown in Scheme 9.

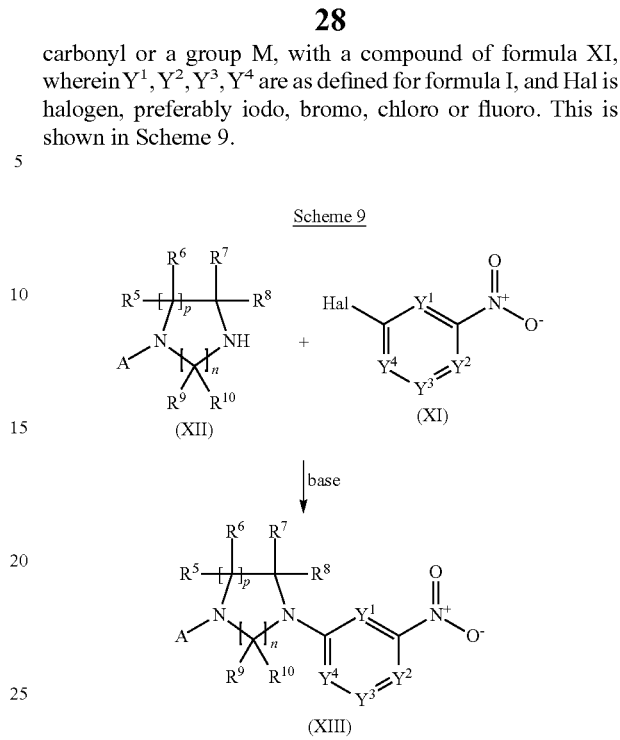

Alternatively, the compounds of formula VI, wherein $R^5$, $R^6$, $R^7$, $R^9$, $R^{10}$, $Y^1$, $Y^2$, $Y^3$, $Y^4$, n, p are as defined for formula I and A is hydrogen, a protecting group such as acetyl, benzyl or tert-butoxycarbonyl or a group M, can be obtained by transformation of a compound of formula XIV, wherein $R^5$, $R^6$, $R^7$, $R^9$, $R^{10}$, $Y^1$, $Y^2$, $Y^4$, n, p are as defined for formula I and A is hydrogen, a protecting group such as acetyl, benzyl or tert-butoxycarbonyl or a group M and Hal is halogen, preferably iodo, bromo or chloro, with a compound of formula XV, wherein $R^{11}$ is as defined for formula I. This is shown in Scheme 10.

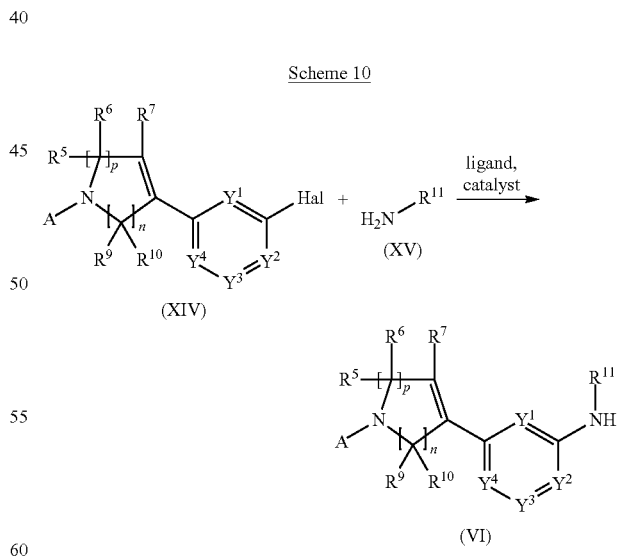

The compounds of formula XIV, wherein $R^5$, $R^6$, $R^7$, $R^9$, $R^{10}$, $Y^1$, $Y^2$, $Y^4$, n, p are as defined for formula I and A is hydrogen, a protecting group such as acetyl, benzyl or tert-butoxycarbonyl or a group M, can be obtained by transformation of a compound of formula VII, wherein $R^5$, $R^6$, $R^7$, $R^9$, $R^{10}$, n, p are as defined for formula I and A is hydrogen, a protecting group such as acetyl, benzyl or tert-butoxycarbonyl or a group M and $R^{31}$ is $B(OH)_2$ or $B(OR^{32})_2$, wherein $R^{32}$ is alkyl or cycloalkyl, with a compound of formula XVI, wherein $Y^1, Y^2, Y^3, Y^4$ are as defined for formula I and Hal is halogen, preferably iodo, bromo or chloro. This is shown in Scheme 11.

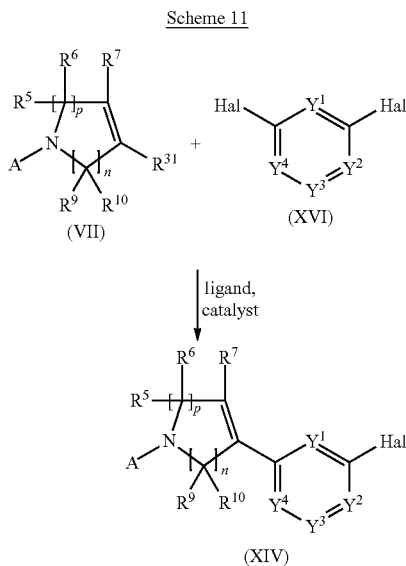

Surprisingly, it has now been found that the novel compounds of formula I have, for practical purposes, a very advantageous level of biological activity for protecting plants against diseases that are caused by fungi.

The compounds of formula I can be used in the agricultural sector and related fields of use e.g. as active ingredients for controlling plant pests or on non-living materials for control of spoilage microorganisms or organisms potentially harmful to man. The novel compounds are distinguished by excellent activity at low rates of application, by being well tolerated by plants and by being environmentally safe. They have very useful curative, preventive and systemic properties and may be used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, e.g., seed, such as fruits, tubers or grains, or plant cuttings (for example rice), for the protection against fungal infections as well as against phytopathogenic fungi occurring in the soil. The propagation material can be treated with a composition comprising a compound of formula I before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore the compounds according to present invention can be used for controlling fungi in related areas, for example in the protection of technical materials, including wood and wood related technical products, in food storage, in hygiene management.

In addition, the invention could be used to protect non-living materials from fungal attack, e.g. lumber, wall boards and paint.

The compounds of formula I are, for example, effective against the phytopathogenic fungi of the following classes: Fungi imperfecti (e.g. *Alternaria* spp.), Basidiomycetes (e.g. *Corticium* spp., *Ceratobasidium* spp., *Waitea* spp., *Thanatephorus* spp., *Rhizoctonia* spp., *Hemileia* spp., *Puccinia* spp., *Phakopsora* spp., *Ustilago* spp., *Tilletia* spp.), Ascomycetes (e.g. *Venturia* spp., *Blumeria* spp., *Erysiphe* spp., *Podosphaera* spp., *Uncinula* spp., *Monilinia* spp., *Sclerotinia* spp., *Colletotrichum* spp., *Glomerella* spp., *Fusarium* spp., *Gibberella* spp., *Monographella* spp., *Phaeosphaeria* spp., *Mycosphaerella* spp., *Cercospora* spp., *Pyrenophora* spp., *Rhynchosporium* spp., *Magnaporthe* spp., *Gaeumannomyces* spp., *Oculimacula* spp., *Ramularia* spp., *Botryotinia* spp.) and Oomycetes (e.g. *Phytophthora* spp., *Pythium* spp., *Plasmopara* spp., *Peronospora* spp., *Pseudoperonospora* spp. *Bremia* spp). Outstanding activity is observed against downy mildew (e.g. *Plasmopara viticola*) and late blight (e.g. *Phytophthora infestans*). Furthermore, the novel compounds of formula I are effective against phytopathogenic gram negative and gram positive bacteria (e.g. *Xanthomonas*spp, *Pseudomonas*spp, *Erwinia amylovora*, *Ralstonia* spp.) and viruses (e.g. tobacco mosaic virus).

Within the scope of present invention, target crops and/or useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as turf and ornamentals.

The useful plants and/or target crops in accordance with the invention include conventional as well as genetically enhanced or engineered varieties such as, for example, insect resistant (e.g. Bt. and VIP varieties) as well as disease resistant, herbicide tolerant (e.g. glyphosate- and glufosinate-resistant maize varieties commercially available under the trade names RoundupReady® and LibertyLink®) and nematode tolerant varieties. By way of example, suitable genetically enhanced or engineered crop varieties include the Stoneville 5599BR cotton and Stoneville 4892BR cotton varieties.

The term "useful plants" and/or "target crops" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" and/or "target crops" is to be understood as including also useful plants which have been so transformed by the use of recombinant DNA techniques that they are capable of synthesising one or more selectively acting toxins, such as are known, for example, from toxin-producing bacteria, especially those of the genus Bacillus.

The term "useful plants" and/or "target crops" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a plant as used herein is intended to embrace the place on which the plants are growing, where the plant propagation materials of the plants are sown or where the plant propagation materials of the plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I are normally used in the form of compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I may be used in the form of fungicidal compositions for controlling or protecting against phytopathogenic microorganisms, comprising as active ingredient at least one compound of formula I or of at least one preferred individual compound as above-defined, in free form or in agrochemically usable salt form, and at least one of the above-mentioned adjuvants.

The invention provides a fungicidal composition comprising at least one compound formula I an agriculturally acceptable carrier and optionally an adjuvant. An agricultural acceptable carrier is for example a carrier that is suitable for agricultural use. Agricultural carriers are well known in the art. Preferably said fungicidal compositions may comprise an additional fungicidal active ingredient in addition to the compound of formula I.

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities. Examples of suitable additional active ingredients include the following: Azoxystrobin (131860-33-8), Dimoxystrobin (149961-52-4), Enestrobin (238410-11-2), Fluoxastrobin (193740-76-0), Kresoxim-methyl (143390-89-0), Metominostrobin (133408-50-1), Orysastrobin (248593-16-0), Picoxystrobin (117428-22-5), Pyraclostrobin (175013-18-0), trifloxystrobin (141517-21-7), Azaconazole (60207-31-0), Bromuconazole (116255-48-2), Cyproconazole (94361-06-5), Difenoconazole (119446-68-3), Diniconazole (83657-24-3), Diniconazole-M (83657-18-5), Epoxiconazole (13385-98-8), Fenbuconazole (114369-43-6), Fluquinconazole (136426-54-5), Flusilazole (85509-19-9), Flutriafol (76674-21-0), Hexaconazole (79983-71-4), Imazalil (58594-72-2), Imibenconazole (86598-92-7), Ipconazole (125225-28-7), Metconazole (125116-23-6), Myclobutanil (88671-89-0), Oxpoconazole (174212-12-5), Pefurazoate (58011-68-0), Penconazole (66246-88-6), Prochloraz (67747-09-5), Propiconazole (60207-90-1), Prothioconazole (178928-70-6), Simeconazole (149508-90-7), Tebuconazole (107534-96-3), Tetraconazole (112281-77-3), Triadimefon (43121-43-3), Triadimenol (55219-65-3), Triflumizole (99387-89-0), Triticonazole (131983-72-7), Diclobutrazol (76738-62-0), Etaconazole (60207-93-4), Fluconazole (86386-73-4), Fluconazole-cis (112839-32-4), Thiabendazole (148-79-8), Quinconazole (103970-75-8), Fenpiclonil (74738-17-3), Fludioxonil (131341-86-1), Cyprodinil (121552-61-2), Mepanipyrim (110235-47-7), Pyrimethanil (53112-28-0), Aldimorph (91315-15-0), Dodemorph (1593-77-7), Fenpropimorph (67564-91-4), Tridemorph (81412-43-3), Fenpropidin (67306-00-7), Spiroxamine (118134-30-8), Isopyrazam (881685-58-1), Sedaxane (874967-67-6), Bixafen (581809-46-3), Penthiopyrad (183675-82-3), Fluxapyroxad (907204-31-3), Boscalid (188425-85-6), Penflufen (494793-67-8), Fluopyram (658066-35-4), Mandipropamid (374726-62-2), Benthiavalicarb (413615-35-7), Dimethomorph (110488-70-5), Chlorothalonil (1897-45-6), Fluazinam (79622-59-6), Dithianon (3347-22-6), Metrafenone (220899-03-6), Tricyclazole (41814-78-2), Mefenoxam (70630-17-0), Metalaxyl (57837-19-1), Acibenzolar (126448-41-7) (Acibenzolar-5-methyl (126448-41-7)), Mancozeb (8018-01-7), Ametoctradine (865318-97-4) Cyflufenamid (180409-60-3), and Kresoxim-methyl (143390-89-0), Ipconazole (125225-28-7), Amisulbrom (348635-87-0), Cyflufenamid (180409-60-3), Ethaboxam (16650-77-3), Fluopicolide (239110-15-7), Fluthianil (304900-25-2), Isotianil (224049-04-1), Proquinazid (189278-12-4), Valiphenal (283159-90-0), 1-methyl-cyclopropene (3100-04-7), Trifloxystrobin (141517-21-7), Sulfur (7704-34-9), Copper ammoniumcarbonate (CAS 33113-08-5); Copper oleate (CAS 1120-44-1); Folpet (133-07-3), Quinoxyfen (124495-18-7), Captan (133-06-2), Fenhexamid (126833-17-8), Glufosinate and its salts (51276-47-2, 35597-44-5 (S-isomer)), Glyphosate (1071-83-6) and its salts (69254-40-6 (Diammonium), 34494-04-7 (Dimethylammonium), 38641-94-0 (Isopropylammonium), 40465-66-5 (Monoammonium), 70901-20-1 (Potassium), 70393-85-0 (Sesquisodium), 81591-81-3 (Trimesium)), 1,3-Dimethyl-1H-pyrazole-4-carboxylic acid (2-dichloromethylene-3-ethyl-1-methyl-indan-4-yl)-amide, 1,3-Dimethyl-1H-pyrazole-4-carboxylic acid (4'-methylsulfanyl-biphenyl-2-yl)-amide, 1,3-Dimethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichloro-phenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine.

Another aspect of invention is related to the use of a compound of formula I or of a preferred individual compound as above-defined, of a composition comprising at least one compound of formula I or at least one preferred individual compound as above-defined, or of a fungicidal mixture comprising at least one compound of formula I or at least one preferred individual compound as above-defined, in admixture with other fungicides, as described above, for controlling or preventing infestation of plants, e.g. useful plants such as crop plants, propagation material thereof, e.g. seeds, harvested crops, e.g. harvested food crops, or non-living materials by phytopathogenic microorganisms, preferably fungal organisms.

A further aspect of invention is related to a method of controlling or preventing an infestation of plants, e.g. useful plants such as crop plants, propagation material thereof, e.g. seeds, harvested crops, e.g. harvested food crops, or of non-living materials by phytopathogenic or spoilage microorganisms or organisms potentially harmful to man, especially fungal organisms, which comprises the application of a compound of formula I or of a preferred individual compound as above-defined as active ingredient to the plants, to parts of the plants or to the locus thereof, to the propagation material thereof, or to any part of the non-living materials.

Controlling or preventing means reducing infestation by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, which comprises the application of a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, e.g. a composition containing the compound of formula I, and, if desired, a solid or liquid adjuvant or monomers for encapsulating the compound of formula I, may be prepared in a known manner, typically by intimately mixing and/or grinding the compound with extenders, for example solvents, solid carriers and, optionally, surface active compounds (surfactants).

The agrochemical formulations and/or compositions will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting examples illustrate the above-described invention in more detail.

EXAMPLE 1

This Example Illustrates the Preparation of 3-chloro-2-hydroxy-N-(3-{1-[2-(5-methyl-3-trifluoromethyl-pyrazol-1-yl)-acetyl]-piperidin-4-yl}-phenyl)-benzamide (Compound No. I.u.003)

a) Preparation of 1-[4-(3-amino-phenyl)-piperidin-1-yl]-2-(5-methyl-3-trifluoromethyl-pyrazol-1-yl)-ethanone To a solution of (5-methyl-3-trifluoromethyl-pyrazol-1-yl)-acetic acid (0.49 g, 2.35 mmol) in DMF (10 mL) is added triethylamine (0.65 mL, 4.7 mmol), followed by 1-hydroxy-7-benzotriazole (0.32 g, 2.35 mmol) and 1-Ethyl-3-(3-dimethylaminopropyl)carbodiimide hydrochloride (0.45 g, 2.35 mmol). After stirring 15 min at RT, 3-Piperidin-4-yl-phenylamine hydrochloride (0.50 g, 2.35 mmol) is added to the reaction mixture. After stirring overnight at RT, solvent is evaporated and the resulting yellow oil is dissolved in ethylacetate (20 mL), washed with saturated aqueous sodium bicarbonate solution (20 mL), and brine (20 mL). The organic layer is dried over sodium sulfate, filtered, and evaporated under reduced pressure to give 1-[4-(3-amino-phenyl)-piperidin-1-yl]-2-(5-methyl-3-trifluoromethyl-pyrazol-1-yl)-ethanone as a crude mixture of good enough purity for the next step (0.86 g, quantitative). $^1$H-NMR (400 MHz, MeOD): δ=1.52-1.63 (m, 1H), 1.64-1.73 (m, 1H), 1.80-1.93 (m, 2H), 2.33 (s, 3H), 2.68-2.81 (m, 2H), 2.99 (s, 2H), 3.21-3.27 (m, 1H), 4.02-4.09 (m, 1H), 4.55-4.62 (m, 1H), 5.12-5.28 (q, 2H), 6.41 (s, 1H), 6.55-6.60 (m, 1H), 6.61-6.62 (m, 1H), 7.00-7.07 (t, 1H), 7.99 (s, 1H). MS: m/z=367 (M+1).

b) Preparation of 3-chloro-2-hydroxy-N-(3-{1-[2-(5-methyl-3-trifluoromethyl-pyrazol-1-yl)-acetyl]-piperidin-4-yl}-phenyl)-benzamide (Compound No. I.u.003)

To a solution of 3-chloro-2-hydroxy-benzoic acid (0.11 g, 0.65 mmol) in acetonitrile (10 mL) is added carbodiimidazole (0.11 g, 0.71 mmol). After stirring the reaction mixture at 60° C. for 2 h, 1-[4-(3-amino-phenyl)-piperidin-1-yl]-2-(5-methyl-3-trifluoromethyl-pyrazol-1-yl)-ethanone (0.20 g, 055 mmol) is added, followed by 1,8-diazabicycloundec-7-ene (0.1 mL, 0.82 mmol). After stirring overnight at 60° C., the reaction mixture is cooled down to RT and then solvent is evaporated and the resulting yellow oil is dissolved in ethylacetate (20 mL), washed with saturated aqueous sodium bicarbonate solution (20 mL), 1N HCl (20 mL) and brine (20 mL). The organic layer is dried over sodium sulfate, filtered, and evaporated under reduced pressure. Cyclohexane is added dropwise to a solution of crude mixture in 1 mL ethylacetate to give after filtration 3-chloro-2-hydroxy-N-(3-{1-[2-(5-methyl-3-trifluoromethyl-pyrazol-1-yl)-acetyl]-piperidin-4-yl}-phenyl)-benzamide (Compound No. I.u.003) (0.148 g, 43%). $^1$H-NMR (400 MHz, MeOD): δ=1.61-1.76 (m, 1H), 1.77-1.90 (m, 1H), 1.92-2.03 (m, 2H), 2.33 (s, 3H), 2.81-2.99 (m, 2H), 3.31-3.41 (m, 1H), 4.09-4.16 (m, 1H), 4.61-4.70 (m, 1H), 5.62-5.81 (q, 2H), 6.45 (s, 1H), 6.95-7.01 (t, 1H), 7.11-7.18 (m, 1H), 7.33-7.39 (t, 1H), 7.51-7.60 (m, 2H), 7.63 (s, 1H), 7.91-7.92 (m, 1H). MS: m/z=521 (M+1).

EXAMPLE 2

This Example Illustrates the Preparation of 3-chloro-2-hydroxy-N-(3-{4-[2-(5-methyl-3-trifluoromethyl-pyrazol-1-yl)-acetyl]-piperazin-1-yl}-phenyl)-benzamide (Compound No. I.ao.003)

a) Preparation of 2-(5-methyl-3-trifluoromethyl-pyrazol-1-yl)-1-[4-(3-nitro-phenyl)-piperazin-1-yl]-ethanone To a solution of (5-methyl-3-trifluoromethyl-pyrazol-1-yl)-acetic acid (1.1 g, 5.28 mmol) in DMF (10 mL) is added triethylamine (1.47 mL, 10.57 mmol), followed by 1-hydroxy-7-benzotriazole (0.755 g, 5.55 mmol) and 1-ethyl-3-(3-dimethylaminopropyl)carbodiimide hydrochloride (1.06 g, 5.55 mmol). After stirring 15 min at RT, 1-(3-nitro-phenyl)-piperazine (1.09 g, 5.28 mmol) is added to the reaction mixture. After stirring overnight at RT, solvent is evaporated and the resulting yellow oil is dissolved in ethylacetate (20 mL), washed with saturated aqueous sodium bicarbonate solution (50 mL), and brine (50 mL). The organic layer is dried over sodium sulfate, filtered, and evaporated under reduced pressure. The crude mixture is purified by column chromatography on silica gel (cyclohexane/ethylacetate 0-80%) to give 2-(5-methyl-3-trifluoromethyl-pyrazol-1-yl)-1-[4-(3-nitro-phenyl)-piperazin-1-yl]-ethanone (1.24 g, 59%). $^1$H-NMR (400 MHz, MeOD): δ=2.31 (s, 3H), 3.31-3.40 (m, 2H), 3.41-3.49 (m, 2H), 3.77-3.85 (m, 4H), 5.25 (s, 2H), 6.43 (s, 1H), 7.38-7.42 (m, 1H), 7.44-7.51 (m, 1H), 7.69-7.72 (m, 1H), 7.80-7.81 (s, 1H). MS: m/z=398 (M+1).

b) Preparation of 1-[4-(3-amino-phenyl)-piperazin-1-yl]-2-(5-methyl-3-trifluoromethyl-pyrazol-1-yl)-ethanone To a suspension of (2-(5-methyl-3-trifluoromethyl-pyrazol-1-yl)-1-[4-(3-nitro-phenyl)-piperazin-1-yl]-ethanone (1.03 g, 2.59 mmol) in ethanol (50 mL) is added 10% Pd/C (100 mg). The reaction mixture is stirred under hydrogen (1 atm) for 2 h, and then filtered over Celite, washed with ethanol, and evaporated under pressure to give 1-[4-(3-aminophenyl)-piperazin-1-yl]-2-(5-methyl-3-trifluoromethyl-pyrazol-1-yl)-ethanone (0.95 g, 99%). $^1$H-NMR (400 MHz, DMSO-d$_6$): δ=2.21 (s, 3H), 3.01-3.09 (m, 2H), 3.11-3.18 (m, 2H), 3.53-3.69 (m, 4H), 4.90 (br, 2H), 5.30 (s, 2H), 6.06-6.11 (m, 1H), 6.13-6.20 (m, 2H), 6.50 (s, 1H), 6.85-6.91 (m, 1H). MS: m/z=368 (M+1).

c) Preparation of 3-chloro-2-hydroxy-N-(3-{4-[2-(5-methyl-3-trifluoromethyl-pyrazol-1-yl)-acetyl]-piperazin-1-yl}-phenyl)-benzamide (Compound No. I.ao.003)

To a solution of 3-chloro-2-hydroxy-benzoic acid (0.11 g, 0.65 mmol) in acetonitrile (10 mL) is added carbodiimidazole (0.11 g, 0.71 mmol). After stirring the reaction mixture at 60° C. for 2 h, 1-[4-(3-amino-phenyl)-piperazin-1-yl]-2-(5-methyl-3-trifluoromethyl-pyrazol-1-yl)-ethanone (0.20 g, 055 mmol) is added, followed by 1,8-diazabicycloundec-7-ene (0.1 mL, 0.82 mmol). After stirring overnight at 60° C., the reaction mixture is cooled down to RT and then solvent is evaporated and the resulting yellow oil is dissolved in ethylacetate (20 mL), washed with saturated aqueous sodium bicarbonate solution (20 mL), 1N HCl (20 mL) and brine (20 mL). The organic layer is dried over sodium sulfate, filtered, and evaporated under reduced pressure. Cyclohexane is added dropwise to a solution of crude mixture in 1 mL ethylacetate to give after filtration 3-chloro-2-hydroxy-N-(3-{4-[2-(5-methyl-3-trifluoromethyl-pyrazol-1-yl)-acetyl]-piperazin-1-yl}-phenyl)-benzamide (Compound No. I.ao.003) (0.090 g, 26%). $^1$H-NMR (400 MHz, MeOD): δ=2.31 (s, 3H), 3.21-3.28 (m, 2H), 3.31-3.39 (m, 2H), 3.77-3.83 (m, 4H), 5.25 (s, 2H), 6.47 (s, 1H), 6.87-6.89 (m, 1H), 6.92-6.99 (m, 1H), 7.17-7.22 (m, 1H), 7.28-7.33 (m, 1H), 7.41-7.42 (m, 1H), 7.57-7.61 (m, 1H), 7.90-7.92 (m, 1H). MS: m/z=522 (M+1).

Table 1 below illustrates examples of individual compounds of formula I according to the invention.

TABLE 1

| individual compounds of formula I according to the invention | | | | |
|---|---|---|---|---|
| Compound No. | $R^1$ | G | Q | $R^{12}$ |
| 001 | F$_3$C— | O | —C(=O)— | 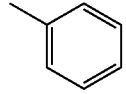 |
| 002 | F$_3$C— | O | —C(=O)— | 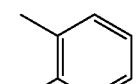 |
| 003 | F$_3$C— | O | —C(=O)— | 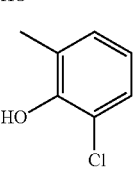 |

TABLE 1-continued individual compounds of formula I according to the invention

| Compound No. | R$^1$ | G | Q | R$^{12}$ |
|---|---|---|---|---|
| 004 | F$_3$C— | O | —C(=O)— | 2,6-difluoro-3-methylphenyl |
| 005 | F$_3$C— | O | —C(=O)— | 2,6-difluoro-3-ethylphenyl |
| 006 | F$_3$C— | O | —C(=O)— | 2,6-difluoro-3-(1-methylethyl)phenyl |
| 007 | F$_3$C— | O | —C(=O)— | 2-chloro-6-methyl-3-(methylsulfonylamino)phenyl |
| 008 | F$_3$C— | O | —C(=O)— | 2-chloro-6-methyl-3-(4-methylphenylsulfonylamino)phenyl |
| 009 | F$_3$C— | O | —C(=O)— | 2-chloro-6-methyl-3-(trifluoromethylsulfonylamino)phenyl |
| 010 | F$_3$C— | O | —C(=O)— | 2-chloro-6-methyl-3-acetamidophenyl |
| 011 | F$_3$C— | O | —C(=O)— | 3-cyano-2-hydroxy-6-methylphenyl |
| 012 | F$_3$C— | O | —C(=O)— | 2-hydroxy-3-methyl-6-nitrophenyl |
| 013 | F$_3$C— | O | —C(=O)— | 2-hydroxy-3-methyl-6-(trifluoromethoxy)phenyl |
| 014 | F$_3$C— | O | —C(=O)— | 2-hydroxy-3-methyl-6-(trifluoromethyl)phenyl |
| 015 | F$_3$C— | O | —C(=O)— | 6-fluoro-2-hydroxy-3-methylphenyl |
| 016 | F$_3$C— | O | —C(=O)— | 6-bromo-2-hydroxy-3-methylphenyl |
| 017 | F$_3$C— | O | —C(=O)— | 2-chloro-6-(hydroxymethyl)-3-methylphenyl |
| 018 | F$_3$C— | O | —C(=O)— | 6-amino-2-chloro-3-methylphenyl |
| 019 | F$_3$C— | O | —C(=O)— | 2-methylthiophen-5-yl |
| 020 | F$_3$C— | O | —C(=O)— | 3-methylthiophen-2-yl |
| 021 | F$_3$C— | O | —C(=O)— | 2-methylfuran-5-yl |
| 022 | F$_3$C— | O | —C(=O)— | 3-methylfuran-2-yl |

TABLE 1-continued
individual compounds of formula I according to the invention
| Compound No. | R¹ | G | Q | R¹² |
|---|---|---|---|---|
| 021 | F₃C— | O | —C(=O)— | 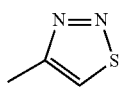 |
| 022 | F₃C— | O | —C(=O)— | 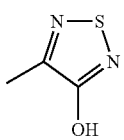 |
| 023 | F₃C— | O | —C(=O)— | 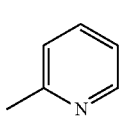 |
| 024 | F₃C— | O | —C(=O)— | 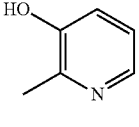 |
| 025 | F₃C— | O | —C(=O)— | 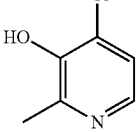 |
| 026 | F₃C— | O | —C(=O)— | 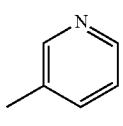 |
| 027 | F₃C— | O | —C(=O)— | 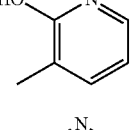 |
| 028 | F₃C— | O | —C(=O)— | 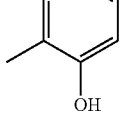 |
| 029 | F₃C— | O | —C(=O)— | 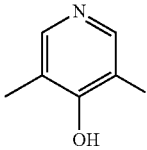 |
| 030 | F₃C— | O | —C(=O)— | 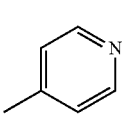 |
| 031 | F₃C— | O | —C(=O)— | 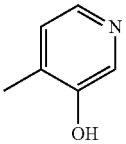 |
| 032 | F₃C— | O | —C(=O)— | 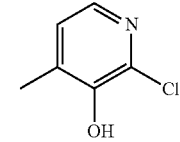 |
| 033 | F₃C— | O | —C(=O)— | 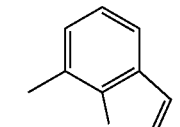 |
| 034 | F₃C— | O | —C(=O)— | 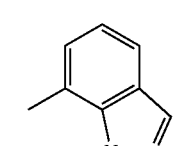 |
| 035 | F₃C— | O | —C(=O)— | 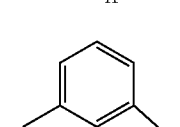 |
| 036 | F₃C— | O | —C(=O)— | 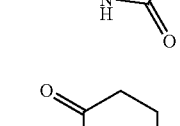 |
| 037 | F₃C— | O | —C(=O)— | 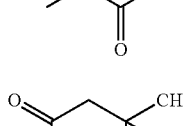 |
| 038 | F₃C— | O | —C(=O)— | 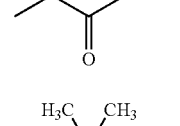 |
| 039 | F₃C— | S | —C(=O)— | 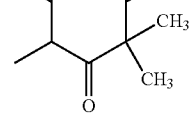 |
| 040 | F₃C— | S | —C(=O)— | 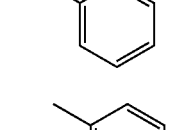 |

TABLE 1-continued
individual compounds of formula I according to the invention
| Compound No. | R¹ | G | Q | R¹² |
|---|---|---|---|---|
| 041 | F₃C— | S | —C(=O)— | 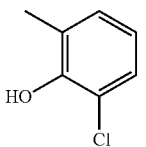 |
| 042 | F₃C— | S | —C(=O)— | 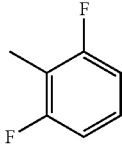 |
| 043 | F₃C— | S | —C(=O)— | 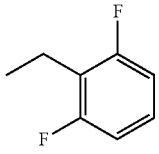 |
| 044 | F₃C— | S | —C(=O)— | 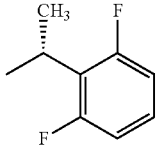 |
| 045 | F₃C— | S | —C(=O)— | 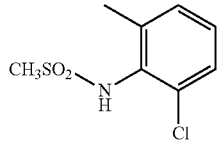 |
| 046 | F₃C— | S | —C(=O)— | 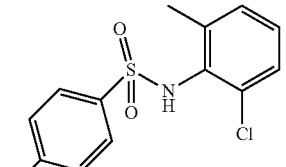 |
| 047 | F₃C— | S | —C(=O)— | 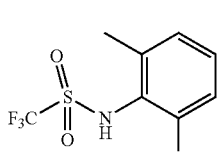 |
| 048 | F₃C— | S | —C(=O)— | 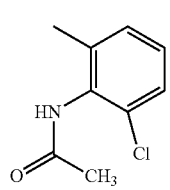 |
| 049 | F₃C— | S | —C(=O)— | 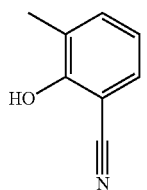 |
| 050 | F₃C— | S | —C(=O)— | 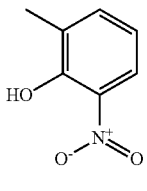 |
| 051 | F₃C— | S | —C(=O)— |  |
| 052 | F₃C— | S | —C(=O)— | 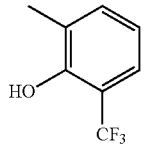 |
| 053 | F₃C— | S | —C(=O)— | 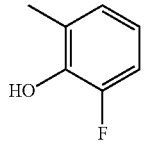 |
| 054 | F₃C— | S | —C(=O)— | 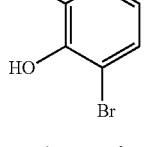 |
| 055 | F₃C— | S | —C(=O)— | 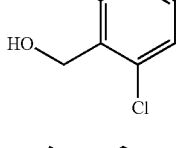 |
| 056 | F₃C— | S | —C(=O)— | 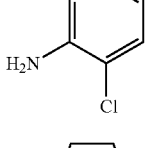 |
| 057 | F₃C— | S | —C(=O)— | 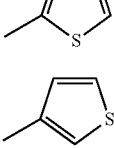 |
| 058 | F₃C— | S | —C(=O)— |  |

TABLE 1-continued
individual compounds of formula I according to the invention
| Compound No. | R¹ | G | Q | R¹² |
|---|---|---|---|---|
| 059 | F₃C— | S | —C(=O)— | 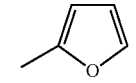 |
| 060 | F₃C— | S | —C(=O)— | 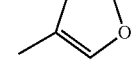 |
| 061 | F₃C— | S | —C(=O)— | 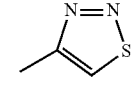 |
| 062 | F₃C— | S | —C(=O)— | 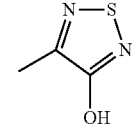 |
| 063 | F₃C— | S | —C(=O)— | 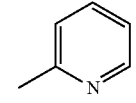 |
| 064 | F₃C— | S | —C(=O)— | 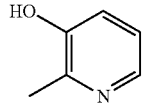 |
| 065 | F₃C— | S | —C(=O)— | 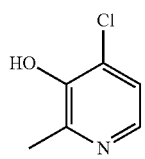 |
| 066 | F₃C— | S | —C(=O)— | 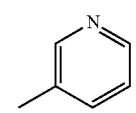 |
| 067 | F₃C— | S | —C(=O)— | 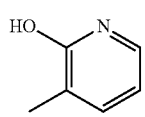 |
| 068 | F₃C— | S | —C(=O)— | 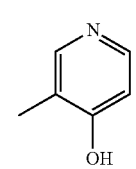 |
| 069 | F₃C— | S | —C(=O)— | 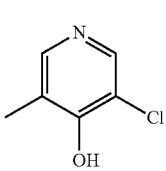 |
| 070 | F₃C— | S | —C(=O)— | 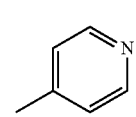 |
| 071 | F₃C— | S | —C(=O)— | 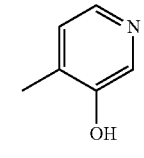 |
| 072 | F₃C— | S | —C(=O)— | 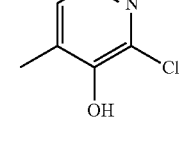 |
| 073 | F₃C— | S | —C(=O)— | 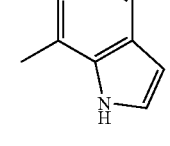 |
| 074 | F₃C— | S | —C(=O)— | 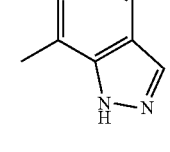 |
| 075 | F₃C— | S | —C(=O)— | 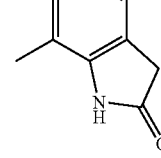 |
| 076 | F₃C— | S | —C(=O)— | 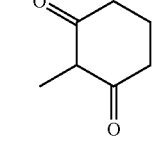 |
| 077 | F₃C— | S | —C(=O)— | 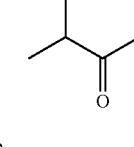 |
| 078 | F₃C— | S | —C(=O)— | 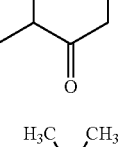 |
| 079 | F₃C— | O | —C(=S)— | 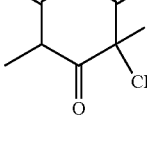 |

TABLE 1-continued
individual compounds of formula I according to the invention
| Compound No. | R¹ | G | Q | R¹² |
|---|---|---|---|---|
| 080 | F₃C— | O | —C(=S)— | 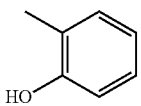 |
| 081 | F₃C— | O | —C(=S)— | 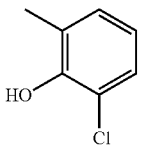 |
| 082 | F₃C— | O | —C(=S)— | 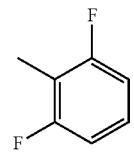 |
| 083 | F₃C— | O | —C(=S)— | 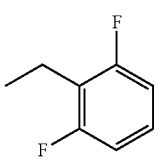 |
| 084 | F₃C— | O | —C(=S)— | 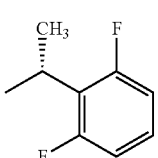 |
| 085 | F₃C— | O | —C(=S)— | 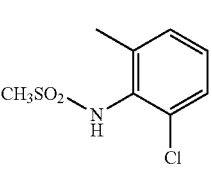 |
| 086 | F₃C— | O | —C(=S)— | 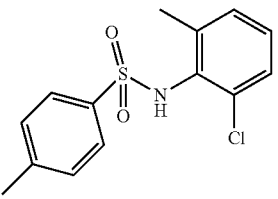 |
| 087 | F₃C— | O | —C(=S)— | 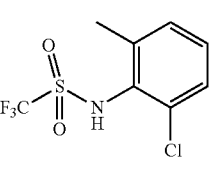 |
| 088 | F₃C— | O | —C(=S)— | 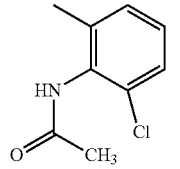 |
| 089 | F₃C— | O | —C(=S)— | 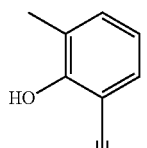 |
| 090 | F₃C— | O | —C(=S)— | 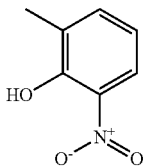 |
| 091 | F₃C— | O | —C(=S)— | 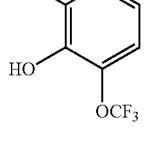 |
| 092 | F₃C— | O | —C(=S)— | 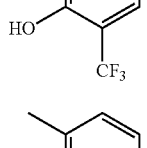 |
| 093 | F₃C— | O | —C(=S)— | 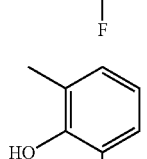 |
| 094 | F₃C— | O | —C(=S)— | 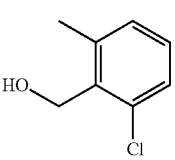 |
| 095 | F₃C— | O | —C(=S)— | 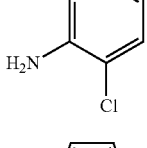 |
| 096 | F₃C— | O | —C(=S)— | 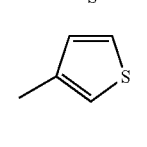 |
| 097 | F₃C— | O | —C(=S)— | 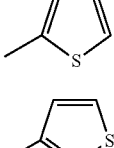 |
| 098 | F₃C— | O | —C(=S)— | 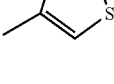 |

TABLE 1-continued
individual compounds of formula I according to the invention
| Compound No. | R¹ | G | Q | R¹² |
|---|---|---|---|---|
| 099 | F₃C— | O | —C(=S)— | 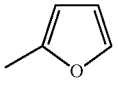 |
| 100 | F₃C— | O | —C(=S)— | 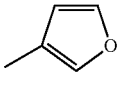 |
| 101 | F₃C— | O | —C(=S)— | 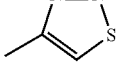 |
| 102 | F₃C— | O | —C(=S)— | 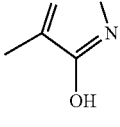 |
| 103 | F₃C— | O | —C(=S)— | 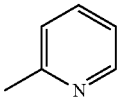 |
| 104 | F₃C— | O | —C(=S)— | 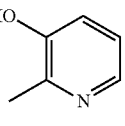 |
| 105 | F₃C— | O | —C(=S)— | 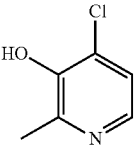 |
| 106 | F₃C— | O | —C(=S)— | 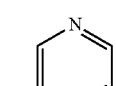 |
| 107 | F₃C— | O | —C(=S)— | 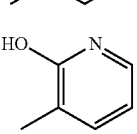 |
| 108 | F₃C— | O | —C(=S)— | 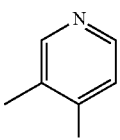 |
| 109 | F₃C— | O | —C(=S)— | 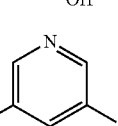 |
| 110 | F₃C— | O | —C(=S)— | 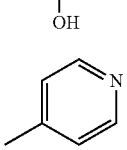 |
| 111 | F₃C— | O | —C(=S)— | 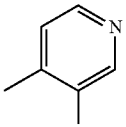 |
| 112 | F₃C— | O | —C(=S)— | 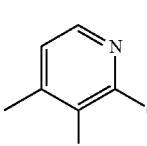 |
| 113 | F₃C— | O | —C(=S)— | 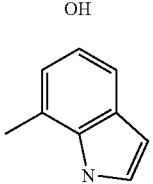 |
| 114 | F₃C— | O | —C(=S)— | 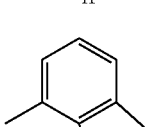 |
| 115 | F₃C— | O | —C(=S)— | 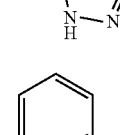 |
| 116 | F₃C— | O | —C(=S)— | 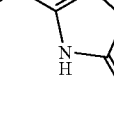 |
| 117 | F₃C— | O | —C(=S)— | 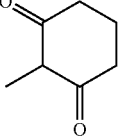 |
| 118 | F₃C— | O | —C(=S)— | 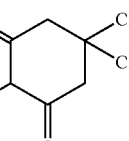 |
| 119 | F₃C— | S | —C(=S)— | 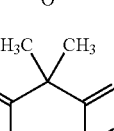 |

TABLE 1-continued
individual compounds of formula I according to the invention
| Compound No. | R¹ | G | Q | R¹² |
|---|---|---|---|---|
| 120 | F₃C— | S | —C(=S)— | 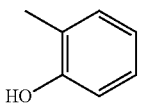 |
| 121 | F₃C— | S | —C(=S)— | 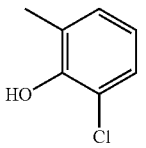 |
| 122 | F₃C— | S | —C(=S)— | 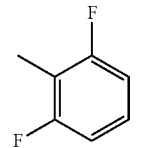 |
| 123 | F₃C— | S | —C(=S)— | 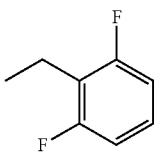 |
| 124 | F₃C— | S | —C(=S)— | 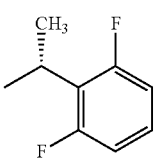 |
| 125 | F₃C— | S | —C(=S)— | 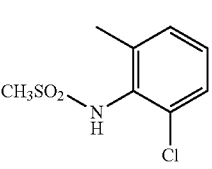 |
| 126 | F₃C— | S | —C(=S)— | 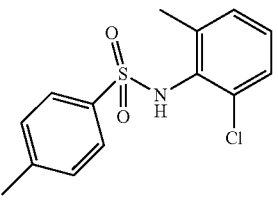 |
| 127 | F₃C— | S | —C(=S)— | 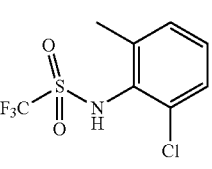 |
| 128 | F₃C— | S | —C(=S)— |  |
| 129 | F₃C— | S | —C(=S)— | 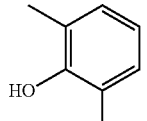 |
| 130 | F₃C— | S | —C(=S)— | 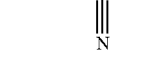 |
| 131 | F₃C— | S | —C(=S)— | 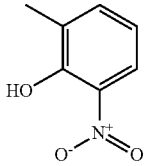 |
| 132 | F₃C— | S | —C(=S)— | 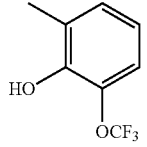 |
| 133 | F₃C— | S | —C(=S)— | 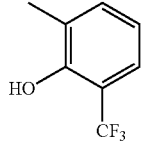 |
| 134 | F₃C— | S | —C(=S)— | 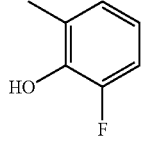 |
| 135 | F₃C— | S | —C(=S)— |  |
| 136 | F₃C— | S | —C(=S)— | 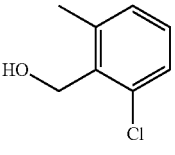 |
| 137 | F₃C— | S | —C(=S)— | 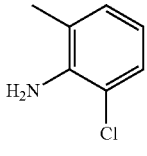 |
| 138 | F₃C— | S | —C(=S)— | 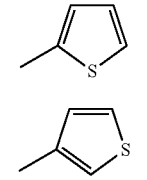 |

TABLE 1-continued
individual compounds of formula I according to the invention
| Compound No. | R¹ | G | Q | R¹² |
|---|---|---|---|---|
| 139 | F₃C— | S | —C(=S)— | 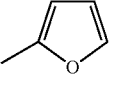 |
| 140 | F₃C— | S | —C(=S)— | 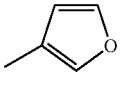 |
| 141 | F₃C— | S | —C(=S)— | 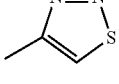 |
| 142 | F₃C— | S | —C(=S)— | 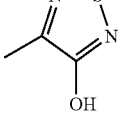 |
| 143 | F₃C— | S | —C(=S)— | 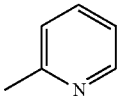 |
| 144 | F₃C— | S | —C(=S)— | 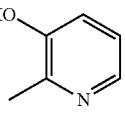 |
| 145 | F₃C— | S | —C(=S)— | 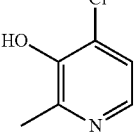 |
| 146 | F₃C— | S | —C(=S)— | 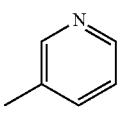 |
| 147 | F₃C— | S | —C(=S)— | 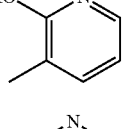 |
| 148 | F₃C— | S | —C(=S)— | 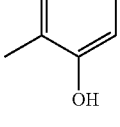 |
| 149 | F₃C— | S | —C(=S)— | 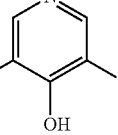 |
| 150 | F₃C— | S | —C(=S)— | 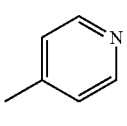 |
| 151 | F₃C— | S | —C(=S)— | 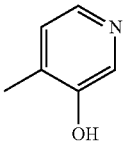 |
| 152 | F₃C— | S | —C(=S)— | 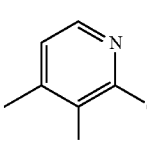 |
| 153 | F₃C— | S | —C(=S)— | 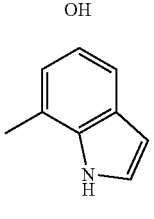 |
| 154 | F₃C— | S | —C(=S)— | 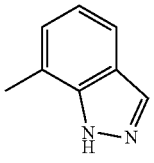 |
| 155 | F₃C— | S | —C(=S)— | 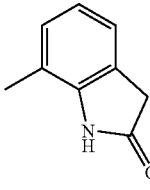 |
| 156 | F₃C— | S | —C(=S)— | 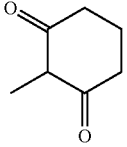 |
| 157 | F₃C— | S | —C(=S)— | 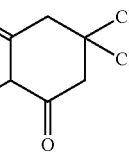 |
| 158 | F₃C— | S | —C(=S)— | 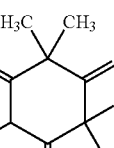 |
| 159 | F₃C— | O | —C(=O)O— | 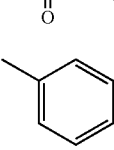 |

TABLE 1-continued
individual compounds of formula I according to the invention
| Compound No. | R¹ | G | Q | R¹² |
|---|---|---|---|---|
| 160 | F₃C— | O | —C(=O)O— | 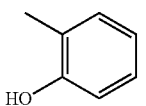 |
| 161 | F₃C— | O | —C(=O)O— | 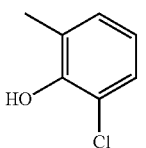 |
| 162 | F₃C— | O | —C(=O)O— | 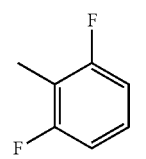 |
| 163 | F₃C— | O | —C(=O)O— | 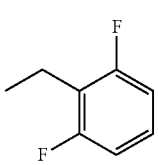 |
| 164 | F₃C— | O | —C(=O)O— | 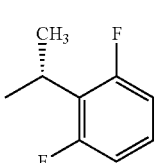 |
| 165 | F₃C— | O | —C(=O)O— | 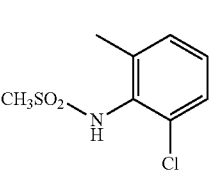 |
| 166 | F₃C— | O | —C(=O)O— | 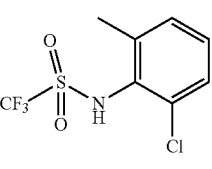 |
| 167 | F₃C— | O | —C(=O)O— | 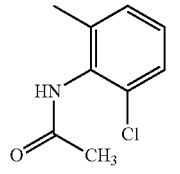 |
| 168 | F₃C— | O | —C(=O)O— | 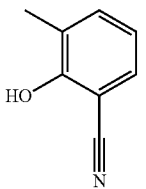 |
| 169 | F₃C— | O | —C(=O)O— | 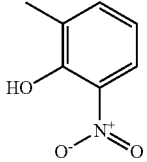 |
| 170 | F₃C— | O | —C(=O)O— | 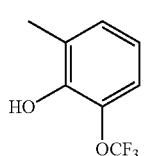 |
| 171 | F₃C— | O | —C(=O)O— | 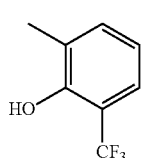 |
| 172 | F₃C— | O | —C(=O)O— | 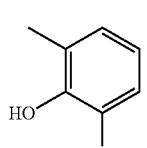 |
| 173 | F₃C— | O | —C(=O)O— | 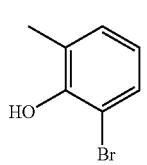 |
| 174 | F₃C— | O | —C(=O)O— | 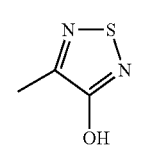 |
| 175 | F₃C— | O | —C(=O)O— | 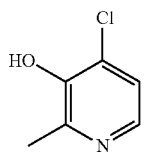 |
| 176 | F₃C— | O | —C(=O)O— | 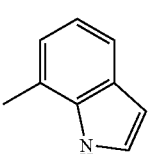 |
| 177 | F₃C— | O | —C(=O)O— | 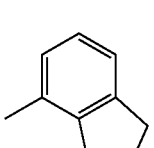 |

TABLE 1-continued
individual compounds of formula I according to the invention
| Compound No. | R¹ | G | Q | R¹² |
|---|---|---|---|---|
| 178 | F₃C— | O | —C(=O)O— | 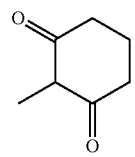 |
| 179 | F₃C— | O | —C(=O)O— | 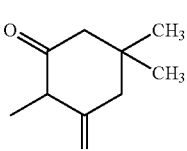 |
| 180 | F₃C— | O | —C(=O)O— | 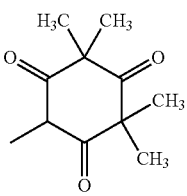 |
| 181 | F₃C— | O | —C(=O)N— | 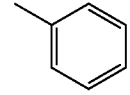 |
| 182 | F₃C— | O | —C(=O)N— | 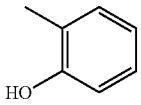 |
| 183 | F₃C— | O | —C(=O)N— | 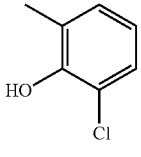 |
| 184 | F₃C— | O | —C(=O)N— | 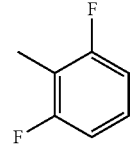 |
| 185 | F₃C— | O | —C(=O)N— | 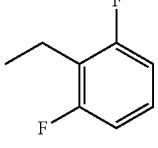 |
| 186 | F₃C— | O | —C(=O)N— | 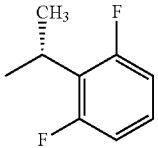 |
| 187 | F₃C— | O | —C(=O)N— | 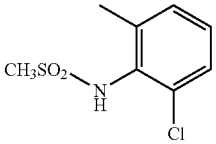 |
| 188 | F₃C— | O | —C(=O)N— | 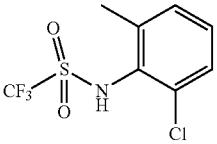 |
| 189 | F₃C— | O | —C(=O)N— | 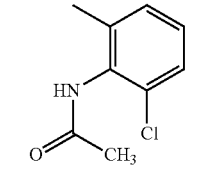 |
| 190 | F₃C— | O | —C(=O)N— | 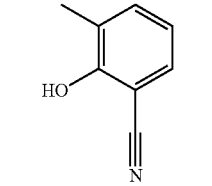 |
| 191 | F₃C— | O | —C(=O)N— | 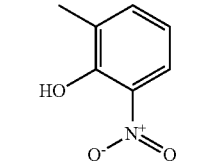 |
| 192 | F₃C— | O | —C(=O)N— | 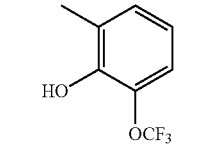 |
| 193 | F₃C— | O | —C(=O)N— | 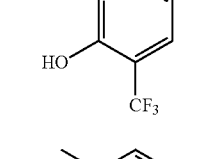 |
| 194 | F₃C— | O | —C(=O)N— | 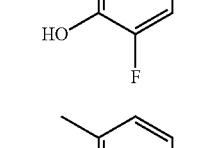 |
| 195 | F₃C— | O | —C(=O)N— | 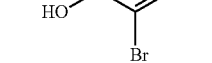 |

TABLE 1-continued individual compounds of formula I according to the invention

| Compound No. | R¹ | G | Q | R¹² |
|---|---|---|---|---|
| 196 | F₃C— | O | —C(=O)N— | 4-methyl-3-hydroxy-1,2,5-thiadiazole |
| 197 | F₃C— | O | —C(=O)N— | 4-chloro-3-hydroxy-2-methylpyridine |
| 198 | F₃C— | O | —C(=O)N— | 7-methylindole |
| 199 | F₃C— | O | —C(=O)N— | 7-methyl-2-oxoindoline |
| 200 | F₃C— | O | —C(=O)N— | 2-methyl-1,3-cyclohexanedione |
| 201 | F₃C— | O | —C(=O)N— | 2,5,5-trimethyl-1,3-cyclohexanedione (dimethyl variant) |
| 202 | F₃C— | O | —C(=O)N— | tetramethyl cyclohexanedione derivative |
| 203 | H₃C— | O | —C(=O)— | 3-methylphenyl |
| 204 | H₃C— | O | —C(=O)— | 2-hydroxy-6-methylphenyl |
| 205 | H₃C— | O | —C(=O)— | 2-chloro-6-hydroxy-3-methylphenyl (approx) |
| 206 | H₃C— | O | —C(=O)— | 2,6-difluoro-3-methylphenyl |
| 207 | H₃C— | O | —C(=O)— | 2-ethyl-3,6-difluoro-phenyl (approx) |
| 208 | H₃C— | O | —C(=O)— | 2-(1-methylethyl)-3,6-difluoro-phenyl |
| 209 | H₃C— | O | —C(=O)— | 2-chloro-6-methyl-N-(methylsulfonyl)anilino |
| 210 | H₃C— | O | —C(=O)— | 2-chloro-6-methyl-N-(p-tolylsulfonyl)anilino |
| 211 | H₃C— | O | —C(=O)— | 2-chloro-6-methyl-N-(trifluoromethylsulfonyl)anilino |
| 2012 | H₃C— | O | —C(=O)— | 2-chloro-6-methyl-N-acetylanilino |
| 213 | H₃C— | O | —C(=O)— | 2-hydroxy-3-cyano-6-methylphenyl |

TABLE 1-continued
individual compounds of formula I according to the invention
| Compound No. | R¹ | G | Q | R¹² |
|---|---|---|---|---|
| 214 | H₃C | O | —C(=O)— | 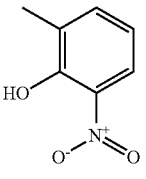 |
| 215 | H₃C | O | —C(=O)— | 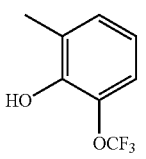 |
| 216 | H₃C— | O | —C(=O)— | 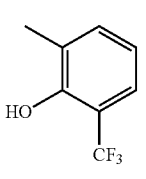 |
| 217 | H₃C | O | —C(=O)— |  |
| 218 | H₃C | O | —C(=O)— |  |
| 219 | H₃C | O | —C(=O)— | 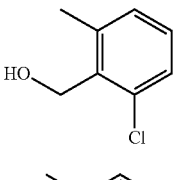 |
| 220 | H₃C | O | —C(=O)— | 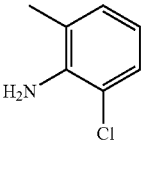 |
| 221 | H₃C | O | —C(=O)— | 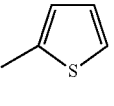 |
| 222 | H₃C | O | —C(=O)— | 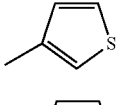 |
| 223 | H₃C | O | —C(=O)— | 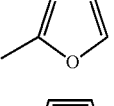 |
| 224 | H₃C | O | —C(=O)— | 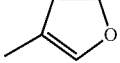 |
| 225 | H₃C | O | —C(=O)— | 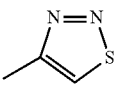 |
| 226 | H₃C | O | —C(=O)— | 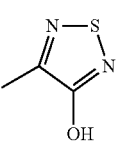 |
| 227 | H₃C | O | —C(=O)— | 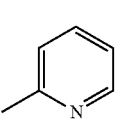 |
| 228 | H₃C | O | —C(=O)— | 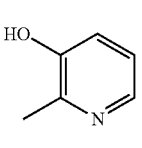 |
| 229 | H₃C— | O | —C(=O)— | 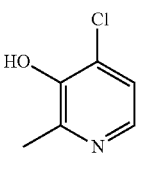 |
| 230 | H₃C | O | —C(=O)— | 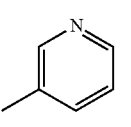 |
| 231 | H₃C | O | —C(=O)— | 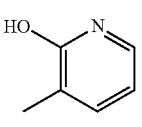 |
| 232 | H₃C | O | —C(=O)— | 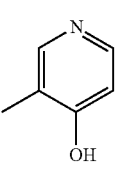 |
| 233 | H₃C | O | —C(=O)— | 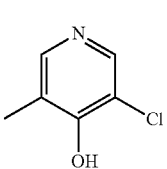 |
| 234 | H₃C | O | —C(=O)— | 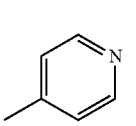 |
| 235 | H₃C | O | —C(=O)— | 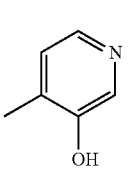 |

TABLE 1-continued
individual compounds of formula I according to the invention
| Compound No. | R¹ | G | Q | R¹² |
|---|---|---|---|---|
| 236 | H₃C | O | —C(=O)— | 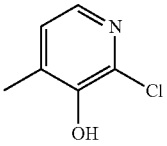 |
| 237 | H₃C | O | —C(=O)— | 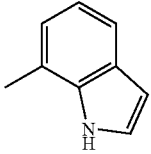 |
| 238 | H₃C | O | —C(=O)— | 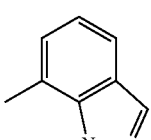 |
| 239 | H₃C | O | —C(=O)— | 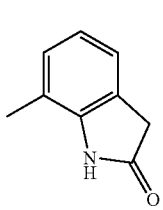 |
| 240 | H₃C | O | —C(=O)— | 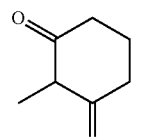 |
| 241 | H₃C | O | —C(=O)— | 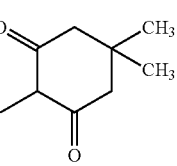 |
| 242 | H₃C | O | —C(=O)— | 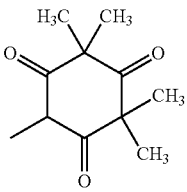 |
| 243 | H₃C | S | —C(=O)— | 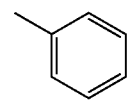 |
| 244 | H₃C | S | —C(=O)— | 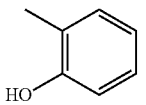 |
| 245 | H₃C | S | —C(=O)— | 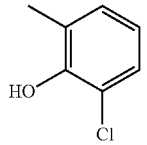 |
| 246 | H₃C | S | —C(=O)— | 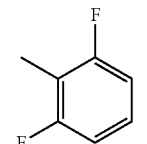 |
| 247 | H₃C | S | —C(=O)— | 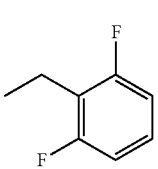 |
| 248 | H₃C | S | —C(=O)— | 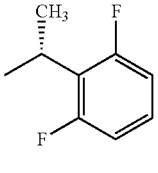 |
| 249 | H₃C | S | —C(=O)— | 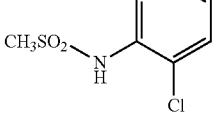 |
| 250 | H₃C | S | —C(=O)— | 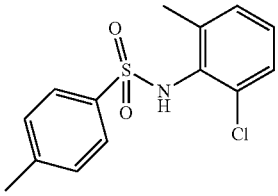 |
| 251 | H₃C | S | —C(=O)— | 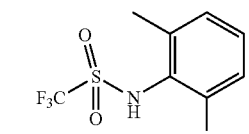 |
| 252 | H₃C | S | —C(=O)— | 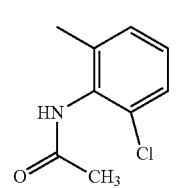 |

TABLE 1-continued individual compounds of formula I according to the invention

| Compound No. | R¹ | G | Q | R¹² |
|---|---|---|---|---|
| 253 | H₃C | S | —C(=O)— | 3-methyl-2-hydroxy-benzonitrile |
| 254 | H₃C | S | —C(=O)— | 3-methyl-2-hydroxy-nitrobenzene |
| 255 | H₃C | S | —C(=O)— | 3-methyl-2-hydroxy-OCF₃-benzene |
| 256 | H₃C | S | —C(=O)— | 3-methyl-2-hydroxy-CF₃-benzene |
| 257 | H₃C | S | —C(=O)— | 3-methyl-2-hydroxy-F-benzene |
| 258 | H₃C | S | —C(=O)— | 3-methyl-2-hydroxy-Br-benzene |
| 259 | H₃C | S | —C(=O)— | 2-methyl-6-chloro-benzyl alcohol |
| 260 | H₃C | S | —C(=O)— | 2-methyl-6-chloro-aniline |
| 261 | H₃C | S | —C(=O)— | 2-methyl-thiophene |
| 262 | H₃C | S | —C(=O)— | 3-methyl-thiophene |
| 263 | H₃C | S | —C(=O)— | 2-methyl-furan |
| 264 | H₃C | S | —C(=O)— | 3-methyl-furan |
| 265 | H₃C | S | —C(=O)— | 4-methyl-1,2,3-thiadiazole |
| 266 | H₃C | S | —C(=O)— | 4-methyl-3-hydroxy-1,2,5-thiadiazole |
| 267 | H₃C | S | —C(=O)— | 2-methyl-pyridine |
| 268 | H₃C | S | —C(=O)— | 2-methyl-3-hydroxy-pyridine |
| 269 | H₃C | S | —C(=O)— | 2-methyl-3-hydroxy-4-chloro-pyridine |
| 270 | H₃C | S | —C(=O)— | 3-methyl-pyridine |
| 271 | H₃C | S | —C(=O)— | 3-methyl-2-hydroxy-pyridine |
| 272 | H₃C | S | —C(=O)— | 3-methyl-4-hydroxy-pyridine |
| 273 | H₃C | S | —C(=O)— | 5-methyl-3-chloro-4-hydroxy-pyridine |
| 274 | H₃C | S | —C(=O)— | 4-methyl-pyridine |

TABLE 1-continued
individual compounds of formula I according to the invention
| Compound No. | R¹ | G | Q | R¹² |
|---|---|---|---|---|
| 275 | H₃C | S | —C(=O)— | 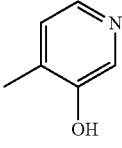 |
| 276 | H₃C | S | —C(=O)— | 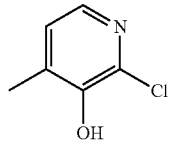 |
| 277 | H₃C | S | —C(=O)— | 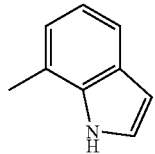 |
| 278 | H₃C | S | —C(=O)— | 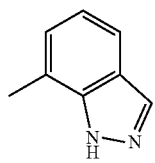 |
| 279 | H₃C | S | —C(=O)— | 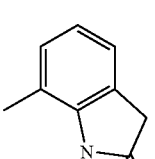 |
| 280 | H₃C | S | —C(=O)— | 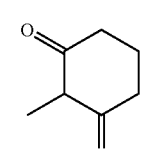 |
| 281 | H₃C | S | —C(=O)— | 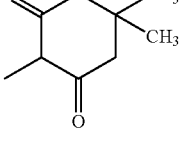 |
| 282 | H₃C | S | —C(=O)— | 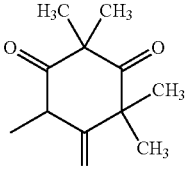 |
| 283 | H₃C | O | —C(=S)— | 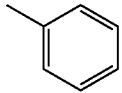 |
| 284 | H₃C | O | —C(=S)— | 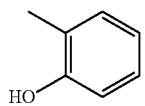 |
| 285 | H₃C | O | —C(=S)— | 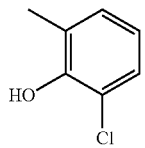 |
| 286 | H₃C | O | —C(=S)— | 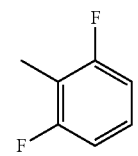 |
| 287 | H₃C | O | —C(=S)— | 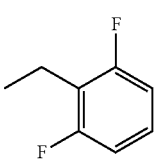 |
| 288 | H₃C | O | —C(=S)— | 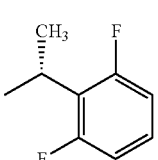 |
| 289 | H₃C | O | —C(=S)— | 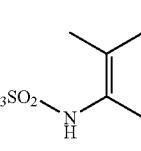 |
| 290 | H₃C | O | —C(=S)— | 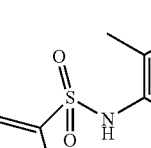 |
| 291 | H₃C | O | —C(=S)— | 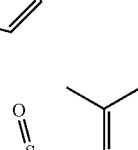 |
| 292 | H₃C | O | —C(=S)— | 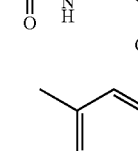 |

TABLE 1-continued
individual compounds of formula I according to the invention
| Compound No. | R¹ | G | Q | R¹² |
|---|---|---|---|---|
| 293 | H₃C | O | —C(=S)— | 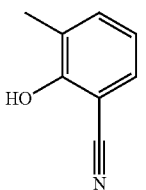 |
| 294 | H₃C | O | —C(=S)— | 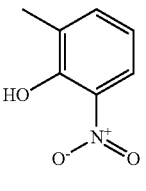 |
| 295 | H₃C | O | —C(=S)— | 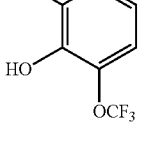 |
| 296 | H₃C | O | —C(=S)— | 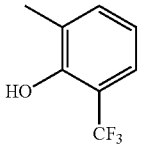 |
| 297 | H₃C | O | —C(=S)— | 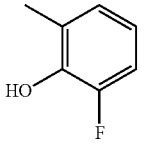 |
| 298 | H₃C | O | —C(=S)— | 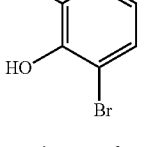 |
| 299 | H₃C | O | —C(=S)— | 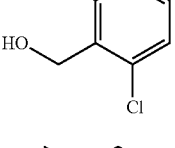 |
| 300 | H₃C | O | —C(=S)— | 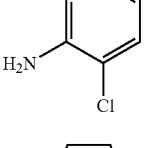 |
| 301 | H₃C | O | —C(=S)— | 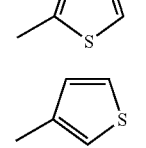 |
| 302 | H₃C | O | —C(=S)— |  |
| 303 | H₃C | O | —C(=S)— | 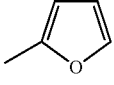 |
| 304 | H₃C | O | —C(=S)— | 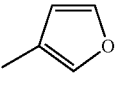 |
| 305 | H₃C | O | —C(=S)— | 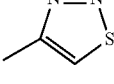 |
| 306 | H₃C | O | —C(=S)— | 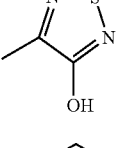 |
| 307 | H₃C | O | —C(=S)— | 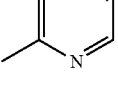 |
| 308 | H₃C | O | —C(=S)— | 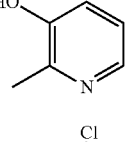 |
| 309 | H₃C | O | —C(=S)— | 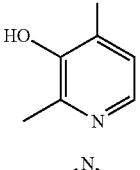 |
| 310 | H₃C | O | —C(=S)— | 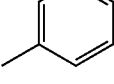 |
| 311 | H₃C | O | —C(=S)— | 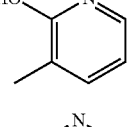 |
| 312 | H₃C | O | —C(=S)— | 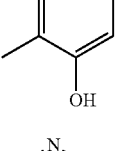 |
| 313 | H₃C | O | —C(=S)— | 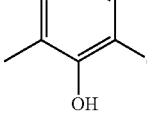 |
| 314 | H₃C | O | —C(=S)— | 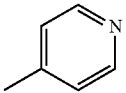 |

TABLE 1-continued individual compounds of formula I according to the invention

| Compound No. | R¹ | G | Q | R¹² |
|---|---|---|---|---|
| 315 | H₃C | O | —C(=S)— | 3-hydroxy-4-methylpyridine |
| 316 | H₃C | O | —C(=S)— | 2-chloro-3-hydroxy-4-methylpyridine |
| 317 | H₃C | O | —C(=S)— | 7-methylindole |
| 318 | H₃C | O | —C(=S)— | 7-methylindazole |
| 319 | H₃C | O | —C(=S)— | 7-methyl-2-oxoindoline |
| 320 | H₃C | O | —C(=S)— | 2-methyl-1,3-cyclohexanedione |
| 321 | H₃C | O | —C(=S)— | 2,5,5-trimethyl-1,3-cyclohexanedione |
| 322 | H₃C | O | —C(=S)— | 2,2,5,6,6-pentamethylcyclohexane-1,3-dione (with extra methyls) |
| 323 | H₃C | S | —C(=S)— | 3-methylphenyl |
| 324 | H₃C | S | —C(=S)— | 2-methylphenol |
| 325 | H₃C | S | —C(=S)— | 3-chloro-6-methyl-2-hydroxyphenyl |
| 326 | H₃C | S | —C(=S)— | 2,6-difluoro-3-methylphenyl |
| 327 | H₃C | S | —C(=S)— | 2-ethyl-3,6-difluoro-methylphenyl |
| 328 | H₃C | S | —C(=S)— | 2-(1-methylethyl)-3,6-difluorophenyl (chiral) |
| 329 | H₃C | S | —C(=S)— | 2-chloro-6-methyl-N-(methylsulfonyl)aniline |
| 330 | H₃C | S | —C(=S)— | 2-chloro-6-methyl-N-(4-methylphenylsulfonyl)aniline |
| 331 | H₃C | S | —C(=S)— | 2-chloro-6-methyl-N-(trifluoromethylsulfonyl)aniline |
| 332 | H₃C | S | —C(=S)— | N-(2-chloro-6-methylphenyl)acetamide |

TABLE 1-continued individual compounds of formula I according to the invention

| Compound No. | R¹ | G | Q | R¹² |
|---|---|---|---|---|
| 333 | H₃C | S | —C(=S)— | 3-methyl-2-hydroxy-benzonitrile |
| 334 | H₃C | S | —C(=S)— | 2-methyl-6-hydroxy-nitrobenzene |
| 335 | H₃C | S | —C(=S)— | 2-methyl-6-hydroxy-3-trifluoromethoxy-benzene |
| 336 | H₃C | S | —C(=S)— | 2-methyl-6-hydroxy-3-trifluoromethyl-benzene |
| 337 | H₃C | S | —C(=S)— | 2-methyl-6-hydroxy-fluoro-benzene |
| 338 | H₃C | S | —C(=S)— | 2-methyl-6-hydroxy-bromo-benzene |
| 339 | H₃C | S | —C(=S)— | 2-(hydroxymethyl)-6-chloro-methylbenzene |
| 340 | H₃C | S | —C(=S)— | 2-amino-6-chloro-methylbenzene |
| 341 | H₃C | S | —C(=S)— | 2-methyl-thiophene |
| 342 | H₃C | S | —C(=S)— | 3-methyl-thiophene |
| 343 | H₃C | S | —C(=S)— | 2-methyl-furan |
| 344 | H₃C | S | —C(=S)— | 3-methyl-furan |
| 345 | H₃C | S | —C(=S)— | 4-methyl-thiadiazole |
| 346 | H₃C | S | —C(=S)— | 4-methyl-3-hydroxy-thiadiazole |
| 347 | H₃C | S | —C(=S)— | 2-methyl-pyridine |
| 348 | H₃C | S | —C(=S)— | 2-methyl-3-hydroxy-pyridine |
| 349 | H₃C | S | —C(=S)— | 2-methyl-3-hydroxy-4-chloro-pyridine |
| 350 | H₃C | S | —C(=S)— | 3-methyl-pyridine |
| 351 | H₃C | S | —C(=S)— | 3-methyl-2-hydroxy-pyridine |
| 352 | H₃C | S | —C(=S)— | 3-methyl-4-hydroxy-pyridine |
| 353 | H₃C | S | —C(=S)— | 5-methyl-3-chloro-4-hydroxy-pyridine |
| 354 | H₃C | S | —C(=S)— | 4-methyl-pyridine |

TABLE 1-continued individual compounds of formula I according to the invention

| Compound No. | R¹ | G | Q | R¹² |
|---|---|---|---|---|
| 355 | H₃C | S | —C(=S)— | 4-methyl-3-hydroxypyridin-yl |
| 356 | H₃C | S | —C(=S)— | 2-chloro-3-hydroxy-4-methylpyridin-yl |
| 357 | H₃C | S | —C(=S)— | 7-methyl-1H-indol-yl |
| 358 | H₃C | S | —C(=S)— | 7-methyl-1H-indazol-yl |
| 359 | H₃C | S | —C(=S)— | 7-methyl-2-oxoindolin-yl |
| 360 | H₃C | S | —C(=S)— | 2-methyl-1,3-cyclohexanedion-yl |
| 361 | H₃C | S | —C(=S)— | 2,4,4-trimethyl-1,3-cyclohexanedion-yl |
| 362 | H₃C | S | —C(=S)— | tetramethyl-1,3-cyclohexanedion-yl |
| 363 | F₂HC— | O | —C(=O)— | 2-methylphenyl |
| 364 | F₂HC— | O | —C(=O)— | 2-hydroxy-6-methylphenyl |
| 365 | F₂HC— | O | —C(=O)— | 3-chloro-2-hydroxy-6-methylphenyl |
| 366 | F₂HC— | O | —C(=O)— | 2,6-difluoro-3-methylphenyl |
| 367 | F₂HC— | O | —C(=O)— | 2-ethyl-3,6-difluorophenyl (approx) |
| 368 | F₂HC— | O | —C(=O)— | 2-(1-methylethyl)-3,6-difluorophenyl |
| 369 | F₂HC— | O | —C(=O)— | N-(2-chloro-6-methylphenyl)methanesulfonamide |
| 370 | F₂HC— | O | —C(=O)— | N-(2-chloro-6-methylphenyl)trifluoromethanesulfonamide |
| 371 | F₂HC— | O | —C(=O)— | N-(2-chloro-6-methylphenyl)acetamide |
| 372 | F₂HC— | O | —C(=O)— | 2-cyano-6-hydroxy-3-methylphenyl |

TABLE 1-continued
individual compounds of formula I according to the invention
| Compound No. | R¹ | G | Q | R¹² |
|---|---|---|---|---|
| 373 | F₂HC— | O | —C(=O)— | 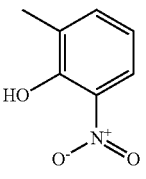 |
| 374 | F₂HC— | O | —C(=O)— | 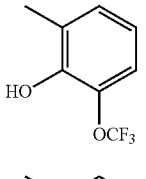 |
| 375 | F₂HC— | O | —C(=O)— | 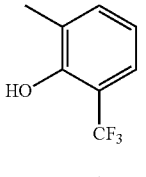 |
| 376 | F₂HC— | O | —C(=O)— |  |
| 377 | F₂HC— | O | —C(=O)— | 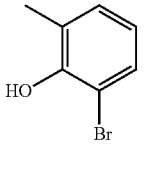 |
| 378 | F₂HC— | O | —C(=O)— | 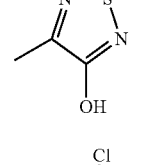 |
| 379 | F₂HC— | O | —C(=O)— | 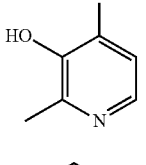 |
| 380 | F₂HC— | O | —C(=O)— | 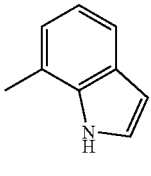 |
| 381 | F₂HC— | O | —C(=O)— | 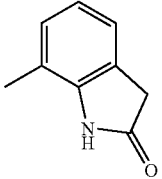 |
| 382 | F₂HC— | O | —C(=O)— | 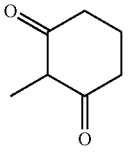 |
| 383 | F₂HC— | O | —C(=O)— | 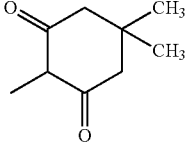 |
| 384 | F₂HC— | O | —C(=O)— | 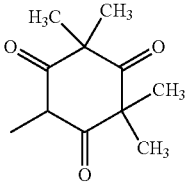 |
| 385 | F₂HC— | S | —C(=O)— | 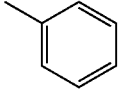 |
| 386 | F₂HC— | S | —C(=O)— | 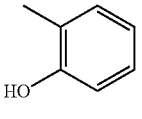 |
| 387 | F₂HC— | S | —C(=O)— | 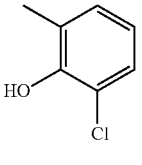 |
| 388 | F₂HC— | S | —C(=O)— | 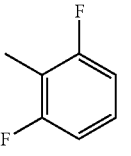 |
| 389 | F₂HC— | S | —C(=O)— | 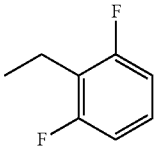 |
| 390 | F₂HC— | S | —C(=O)— | 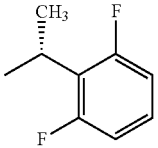 |

TABLE 1-continued individual compounds of formula I according to the invention

| Compound No. | R¹ | G | Q | R¹² |
|---|---|---|---|---|
| 391 | F₂HC— | S | —C(=O)— | 2-methyl-6-chloro-N-(methylsulfonyl)aniline |
| 392 | F₂HC— | S | —C(=O)— | 2-methyl-6-chloro-N-(trifluoromethylsulfonyl)aniline |
| 393 | F₂HC— | S | —C(=O)— | N-(2-methyl-6-chlorophenyl)acetamide |
| 394 | F₂HC— | S | —C(=O)— | 3-methyl-2-hydroxybenzonitrile |
| 395 | F₂HC— | S | —C(=O)— | 3-methyl-2-hydroxy-nitrobenzene |
| 396 | F₂HC— | S | —C(=O)— | 3-methyl-2-hydroxy-trifluoromethoxybenzene |
| 397 | F₂HC— | S | —C(=O)— | 3-methyl-2-hydroxy-trifluoromethylbenzene |
| 398 | F₂HC— | S | —C(=O)— | 3-methyl-2-hydroxy-fluorobenzene |
| 399 | F₂HC— | S | —C(=O)— | 3-methyl-2-hydroxy-bromobenzene |
| 400 | F₂HC— | S | —C(=O)— | 4-methyl-3-hydroxy-1,2,5-thiadiazole |
| 401 | F₂HC— | S | —C(=O)— | 4-chloro-3-hydroxy-2-methylpyridine |
| 402 | F₂HC— | S | —C(=O)— | 7-methylindole |
| 403 | F₂HC— | S | —C(=O)— | 7-methyl-2-indolinone |
| 404 | F₂HC— | S | —C(=O)— | 2-methyl-1,3-cyclohexanedione |
| 405 | F₂HC— | S | —C(=O)— | 2,4,4-trimethyl-1,3-cyclohexanedione |
| 406 | F₂HC— | S | —C(=O)— | tetramethyl-1,3-cyclohexanedione |
| 407 | F₂HC— | O | —C(=S)— | 2-methylphenyl |
| 408 | F₂HC— | O | —C(=S)— | 2-methylphenol |

TABLE 1-continued
individual compounds of formula I according to the invention
| Compound No. | R¹ | G | Q | R¹² |
|---|---|---|---|---|
| 409 | F₂HC— | O | —C(=S)— | 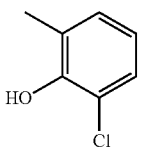 |
| 410 | F₂HC— | O | —C(=S)— | 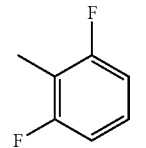 |
| 411 | F₂HC— | O | —C(=S)— | 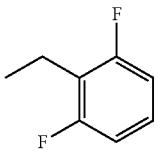 |
| 412 | F₂HC— | O | —C(=S)— | 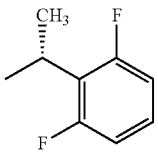 |
| 413 | F₂HC— | O | —C(=S)— | 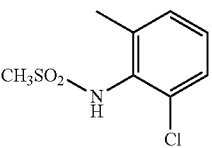 |
| 414 | F₂HC— | O | —C(=S)— | 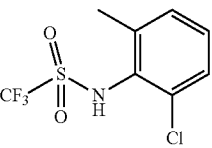 |
| 415 | F₂HC— | O | —C(=S)— | 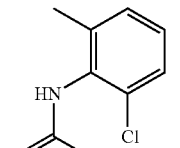 |
| 416 | F₂HC— | O | —C(=S)— | 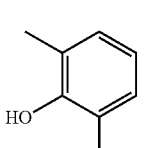 |
| 417 | F₂HC— | O | —C(=S)— | 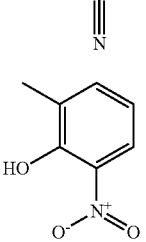 |
| 418 | F₂HC— | O | —C(=S)— | 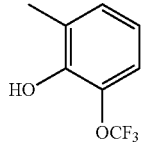 |
| 419 | F₂HC— | O | —C(=S)— | 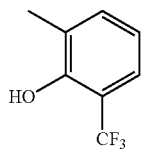 |
| 420 | F₂HC— | O | —C(=S)— | 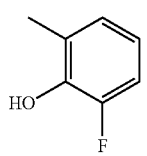 |
| 421 | F₂HC— | O | —C(=S)— | 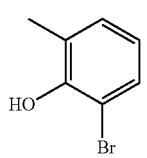 |
| 422 | F₂HC— | O | —C(=S)— | 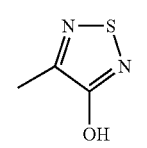 |
| 423 | F₂HC— | O | —C(=S)— | 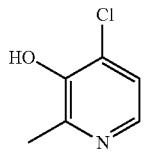 |
| 424 | F₂HC— | O | —C(=S)— | 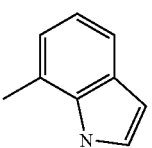 |
| 425 | F₂HC— | O | —C(=S)— | 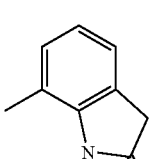 |
| 426 | F₂HC— | O | —C(=S)— | 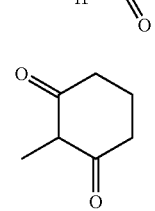 |

TABLE 1-continued individual compounds of formula I according to the invention

| Compound No. | R$^1$ | G | Q | R$^{12}$ |
|---|---|---|---|---|
| 427 | F$_2$HC— | O | —C(=S)— | 2,4-dimethyl-4-methylcyclohexane-1,3-dione derivative |
| 428 | F$_2$HC— | O | —C(=S)— | tetramethyl cyclohexane-1,3,5-trione derivative |
| 429 | F$_2$HC— | S | —C(=S)— | 2-methylphenyl |
| 430 | F$_2$HC— | S | —C(=S)— | 2-methyl-6-hydroxyphenyl |
| 431 | F$_2$HC— | S | —C(=S)— | 2-methyl-6-hydroxy-3-chlorophenyl |
| 432 | F$_2$HC— | S | —C(=S)— | 2-methyl-3,6-difluorophenyl |
| 433 | F$_2$HC— | S | —C(=S)— | 2-ethyl-3,6-difluorophenyl |
| 434 | F$_2$HC— | S | —C(=S)— | 2-(1-methylethyl)-3,6-difluorophenyl |
| 435 | F$_2$HC— | S | —C(=S)— | 2-methyl-6-(methylsulfonylamino)-3-chlorophenyl |
| 436 | F$_2$HC— | S | —C(=S)— | 2-methyl-6-(trifluoromethylsulfonylamino)-3-chlorophenyl |
| 437 | F$_2$HC— | S | —C(=S)— | 2-methyl-6-acetamido-3-chlorophenyl |
| 438 | F$_2$HC— | S | —C(=S)— | 2-methyl-3-hydroxy-6-cyanophenyl |
| 439 | F$_2$HC— | S | —C(=S)— | 2-methyl-3-hydroxy-6-nitrophenyl |
| 440 | F$_2$HC— | S | —C(=S)— | 2-methyl-3-hydroxy-6-trifluoromethoxyphenyl |
| 441 | F$_2$HC— | S | —C(=S)— | 2-methyl-3-hydroxy-6-trifluoromethylphenyl |
| 442 | F$_2$HC— | S | —C(=S)— | 2-methyl-3-hydroxy-6-fluorophenyl |
| 443 | F$_2$HC— | S | —C(=S)— | 2-methyl-3-hydroxy-6-bromophenyl |
| 444 | F$_2$HC— | S | —C(=S)— | 4-methyl-3-hydroxy-1,2,5-thiadiazol-yl |

TABLE 1-continued individual compounds of formula I according to the invention

| Compound No. | R¹ | G | Q | R¹² |
|---|---|---|---|---|
| 445 | F₂HC— | S | —C(=S)— | 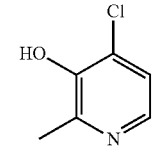 |
| 446 | F₂HC— | S | —C(=S)— | 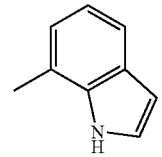 |
| 447 | F₂HC— | S | —C(=S)— | 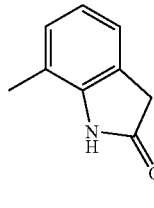 |
| 448 | F₂HC— | S | —C(=S)— | 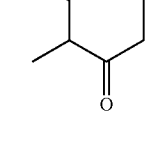 |
| 449 | F₂HC— | S | —C(=S)— | 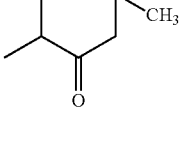 |
| 450 | F₂HC— | S | —C(=S)— | 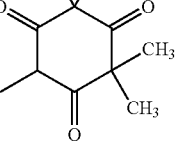 | where
a) 450 compounds of formula (I.a):

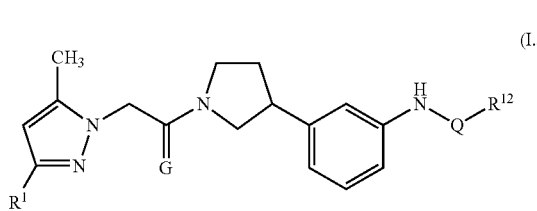

(I.a)

wherein G, Q, R¹ and R¹² are as defined in Table 1.

b) 450 compounds of formula (I.b):

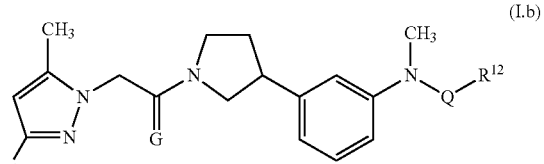

(I.b)

wherein G, Q, R¹ and R¹² are as defined in Table 1.

c) 450 compounds of formula (I.c):

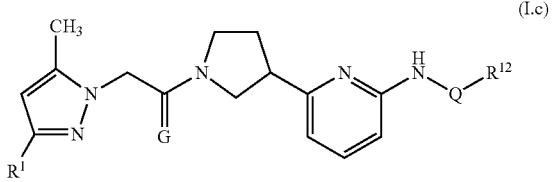

(I.c)

wherein G, Q, R¹ and R¹² are as defined in Table 1.

d) 450 compounds of formula (I.d):

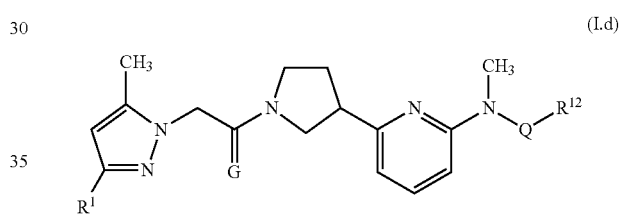

(I.d)

wherein G, Q, R¹ and R¹² are as defined in Table 1.

e) 450 compounds of formula (I.e):

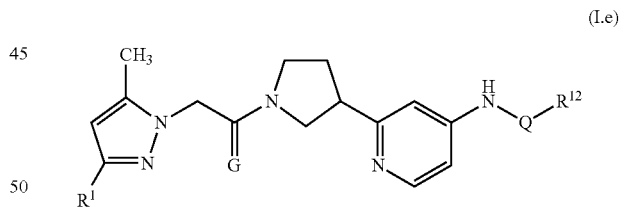

(I.e)

wherein G, Q, R¹ and R¹² are as defined in Table 1.

f) 450 compounds of formula (I.f):

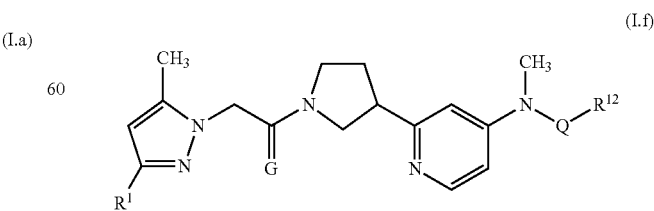

(I.f)

wherein G, Q, R¹ and R¹² are as defined in Table 1.

g) 450 compounds of formula (I.g):

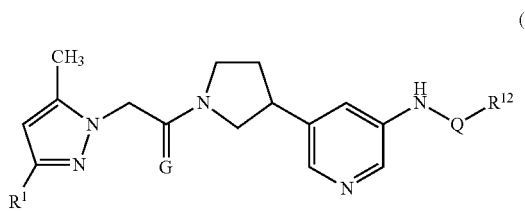
(I.g)

wherein G, Q, $R^1$ and $R^{12}$ are as defined in Table 1.

h) 450 compounds of formula (I.h):

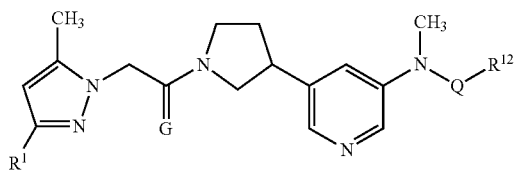
(I.h)

wherein G, Q, $R^1$ and $R^{12}$ are as defined in Table 1.

i) 450 compounds of formula (I.i):

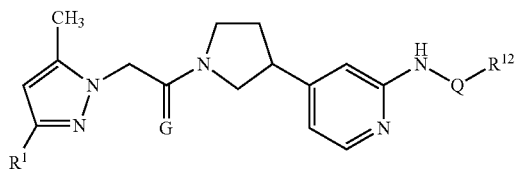
(I.i)

wherein G, Q, $R^1$ and $R^{12}$ are as defined in Table 1.

j) 450 compounds of formula (I.j):

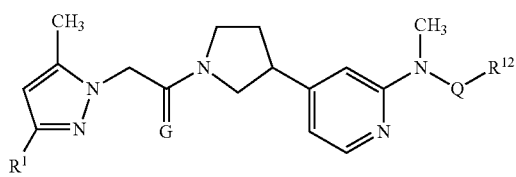
(I.j)

wherein G, Q, $R^1$ and $R^{12}$ are as defined in Table 1.

k) 450 compounds of formula (I.k):

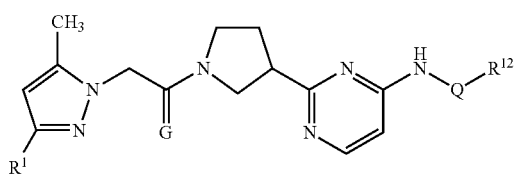
(I.k)

wherein G, Q, $R^1$ and $R^{12}$ are as defined in Table 1.

l) 450 compounds of formula (I.l):

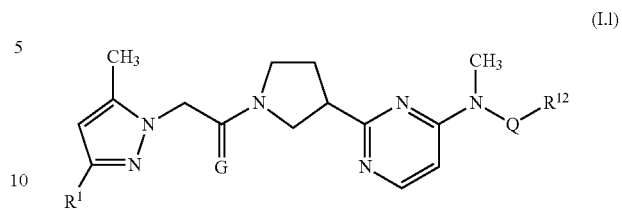
(I.l)

Wherein G, Q, $R^1$ and $R^{12}$ are as defined in Table 1.

m) 450 compounds of formula (I.m):

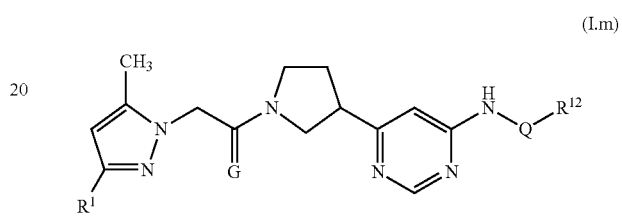
(I.m)

wherein G, Q, $R^1$ and $R^{12}$ are as defined in Table 1.

n) 450 compounds of formula (I.n):

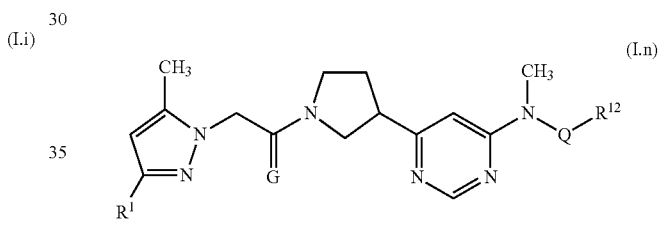
(I.n)

Wherein G, Q, $R^1$ and $R^{12}$ are as defined in Table 1.

o) 450 compounds of formula (I.o):

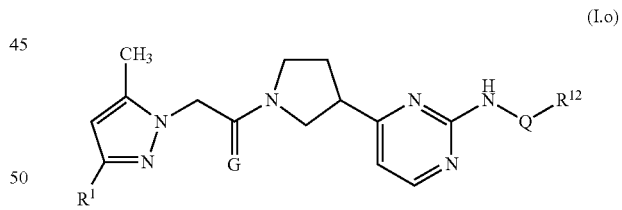
(I.o)

wherein G, Q, $R^1$ and $R^{12}$ are as defined in Table 1.

p) 450 compounds of formula (I.p):

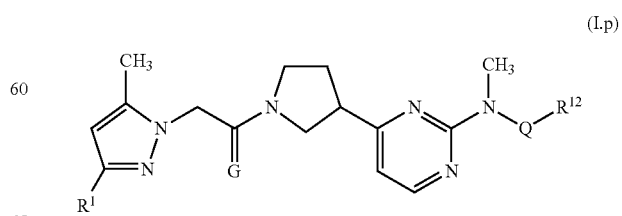
(I.p)

Wherein G, Q, $R^1$ and $R^{12}$ are as defined in Table 1.

q) 450 compounds of formula (I.q):

(I.q)

wherein G, Q, R$^1$ and R$^{12}$ are as defined in Table 1.

r) 450 compounds of formula (I.r):

(I.r)

Wherein G, Q, R$^1$ and R$^{12}$ are as defined in Table 1.

s) 450 compounds of formula (I.s):

(I.s)

wherein G, Q, R$^1$ and R$^{12}$ are as defined in Table 1.

t) 450 compounds of formula (I.t):

(I.t)

Wherein G, Q, R$^1$ and R$^{12}$ are as defined in Table 1.

u) 450 compounds of formula (I.u):

(I.u)

wherein G, Q, R$^1$ and R$^{12}$ are as defined in Table 1.

v) 450 compounds of formula (I.v):

(I.v)

wherein G, Q, R$^1$ and R$^{12}$ are as defined in Table 1.

w) 450 compounds of formula (I.w):

(I.w)

wherein G, Q, R$^1$ and R$^{12}$ are as defined in Table 1.

x) 450 compounds of formula (I.x):

(I.x)

wherein G, Q, R$^1$ and R$^{12}$ are as defined in Table 1.

y) 450 compounds of formula (I.y):

(I.y)

wherein G, Q, R$^1$ and R$^{12}$ are as defined in Table 1.

z) 450 compounds of formula (I.z):

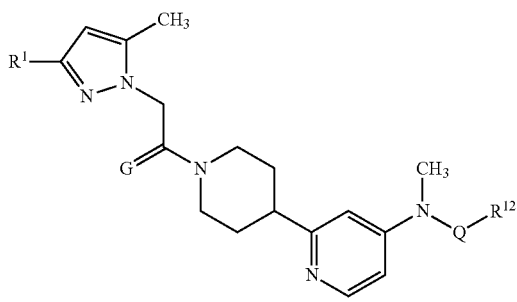

(I.z)

wherein G, Q, $R^1$ and $R^{12}$ are as defined in Table 1.

aa) 450 compounds of formula (I.aa):

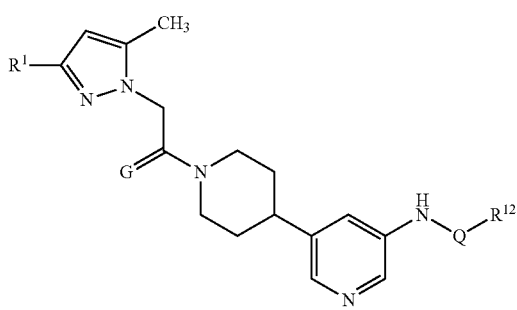

(I.aa)

wherein G, Q, $R^1$ and $R^{12}$ are as defined in Table 1.

ab) 450 compounds of formula (I.ab):

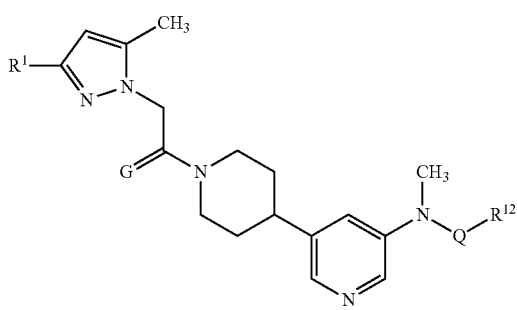

(I.ab)

wherein G, Q, $R^1$ and $R^{12}$ are as defined in Table 1.

ac) 450 compounds of formula (I.ac):

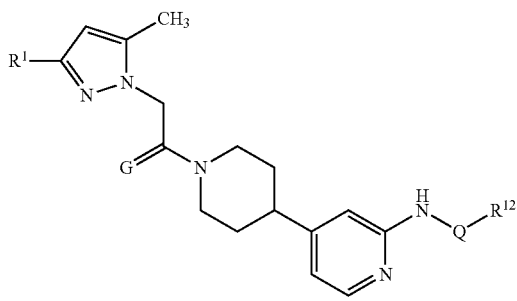

(I.ac)

wherein G, Q, $R^1$ and $R^{12}$ are as defined in Table 1.

ad) 450 compounds of formula (I.ad):

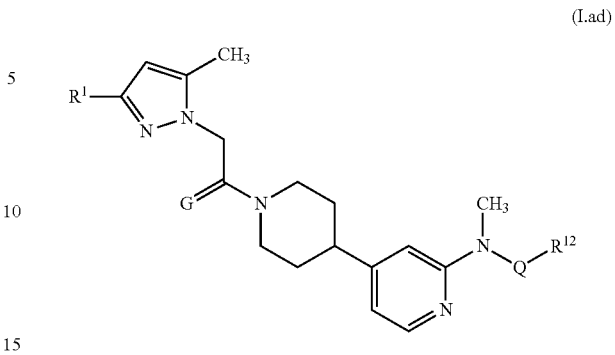

(I.ad)

wherein G, Q, $R^1$ and $R^{12}$ are as defined in Table 1.

ae) 450 compounds of formula (I.ae):

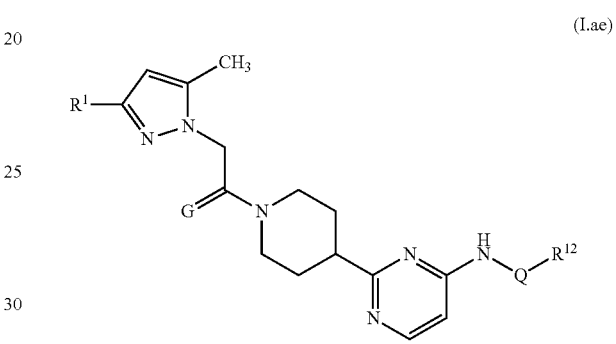

(I.ae)

wherein G, Q, $R^1$ and $R^{12}$ are as defined in Table 1.

af) 450 compounds of formula (I.af):

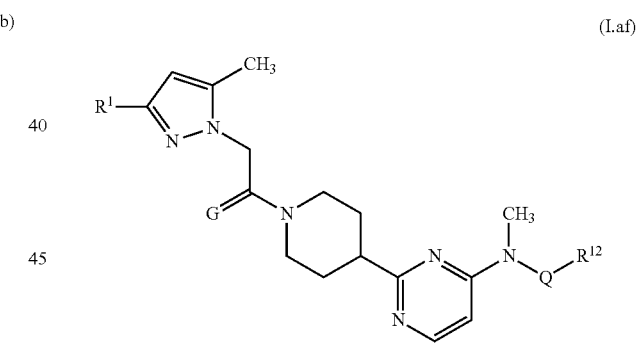

(I.af)

wherein G, Q, $R^1$ and $R^{12}$ are as defined in Table 1.

ag) 450 compounds of formula (I.ag):

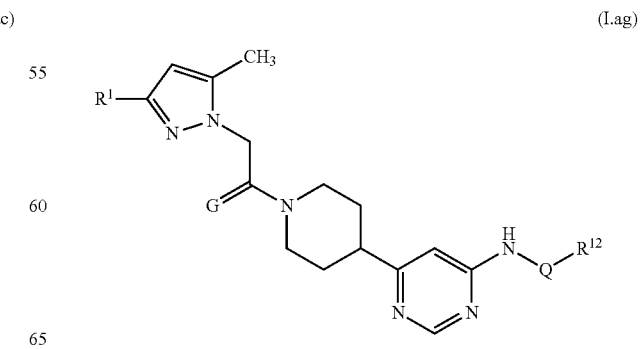

(I.ag)

wherein G, Q, $R^1$ and $R^{12}$ are as defined in Table 1.

ah) 450 compounds of formula (I.ah):

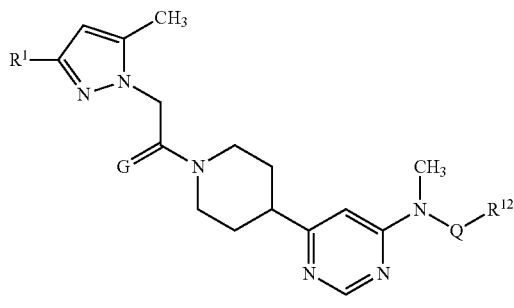
(I.ah)

wherein G, Q, R¹ and R¹² are as defined in Table 1.

ai) 450 compounds of formula (Iai):

(I.ai)

wherein G, Q, R¹ and R¹² are as defined in Table 1.

aj) 450 compounds of formula (I.aj):

(I.aj)

wherein G, Q, R¹ and R¹² are as defined in Table 1.

ak) 450 compounds of formula (I.ak):

(I.ak)

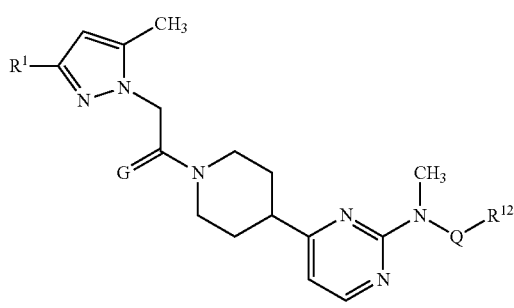

wherein G, Q, R¹ and R¹² are as defined in Table 1.

al) 450 compounds of formula (I.al):

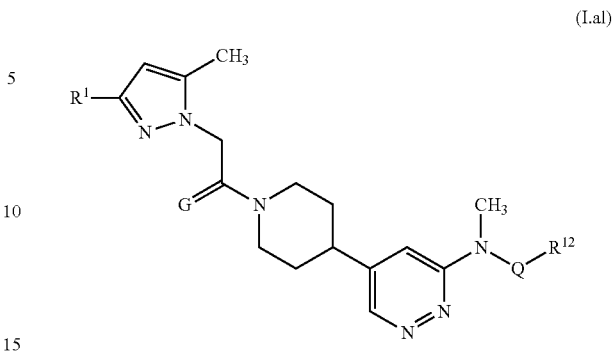
(I.al)

wherein G, Q, R¹ and R¹² are as defined in Table 1.

am) 450 compounds of formula (Iam):

(I.am)

wherein G, Q, R¹ and R¹² are as defined in Table 1.

an) 450 compounds of formula (I.an):

(I.an)

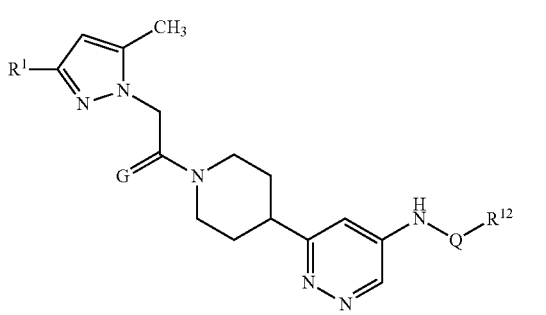

wherein G, Q, R¹ and R¹² are as defined in Table 1.

ao) 450 compounds of formula (I.ao):

(I.ao)

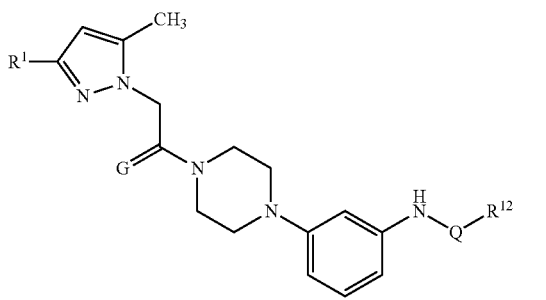

wherein G, Q, R¹ and R¹² are as defined in Table 1.

ap) 450 compounds of formula (I.ap):

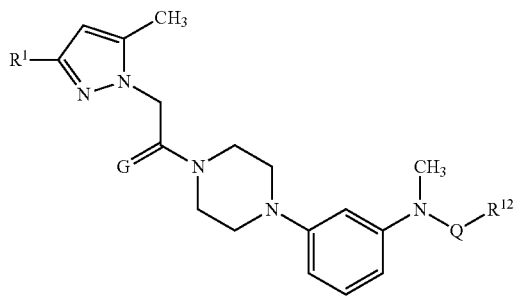
(I.ap)

wherein G, Q, R¹ and R¹² are as defined in Table 1.

aq) 450 compounds of formula (I.aq):

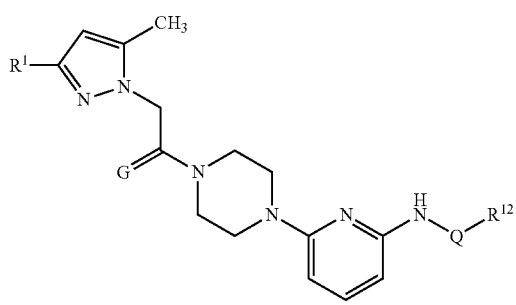
(I.aq)

wherein G, Q, R¹ and R¹² are as defined in Table 1.

ar) 450 compounds of formula (I.ar):

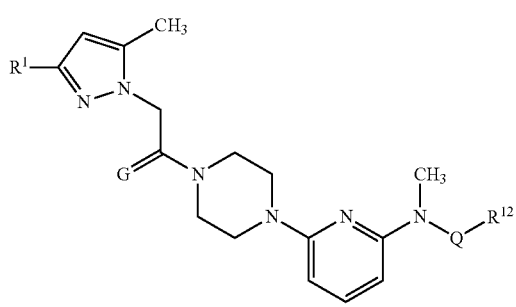
(I.ar)

wherein G, Q, R¹ and R¹² are as defined in Table 1.

as) 450 compounds of formula (I.as):

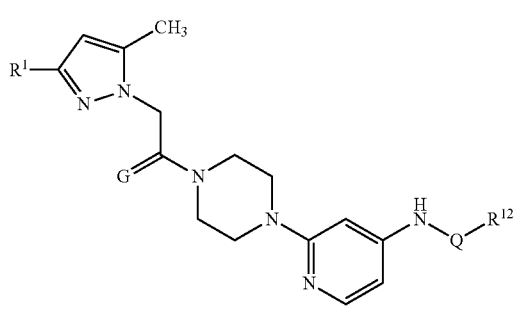
(I.as)

wherein G, Q, R¹ and R¹² are as defined in Table 1.

at) 450 compounds of formula (I.at):

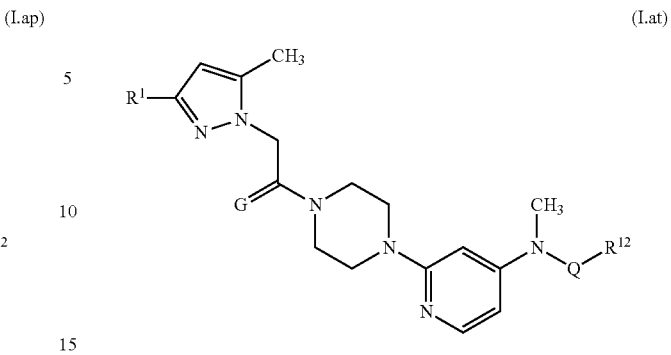
(I.at)

wherein G, Q, R¹ and R¹² are as defined in Table 1.

au) 450 compounds of formula (I.au):

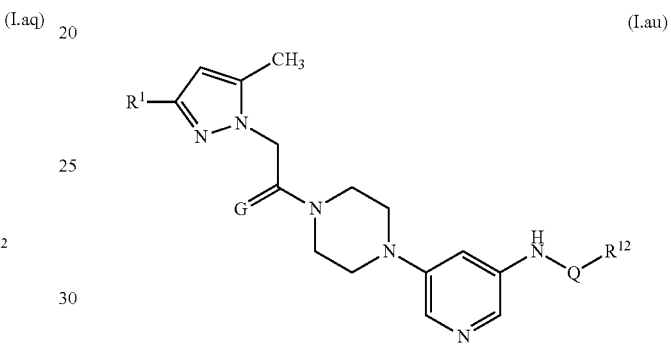
(I.au)

wherein G, Q, R¹ and R¹² are as defined in Table 1.

av) 450 compounds of formula (I.av):

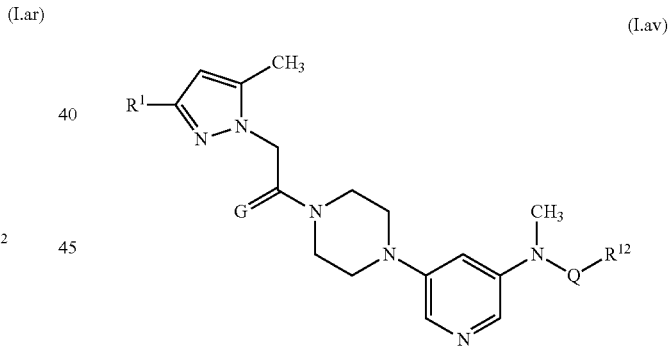
(I.av)

wherein G, Q, R¹ and R¹² are as defined in Table 1.

aw) 450 compounds of formula (I.aw):

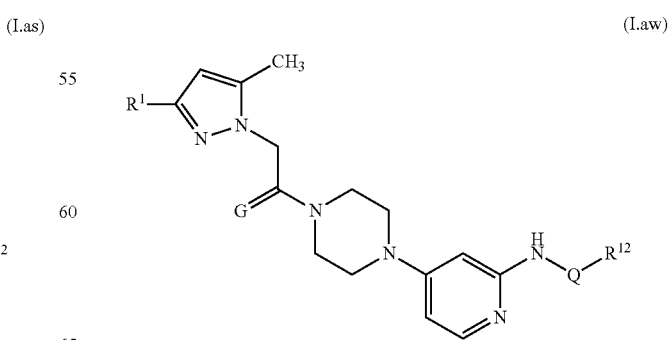
(I.aw)

wherein G, Q, R¹ and R¹² are as defined in Table 1.

ax) 450 compounds of formula (I.ax):

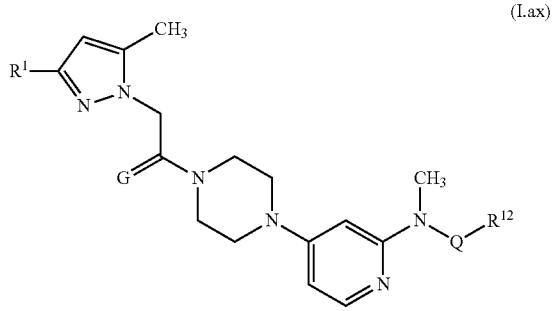

(I.ax)

wherein G, Q, R¹ and R¹² are as defined in Table 1.

ay) 450 compounds of formula (I.ay):

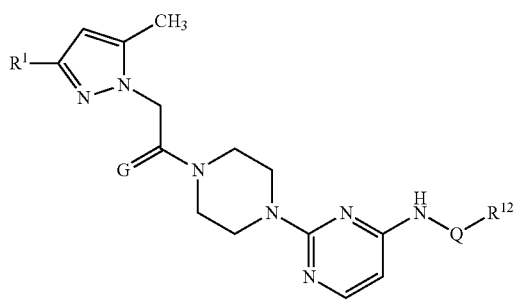

(I.ay)

wherein G, Q, R¹ and R¹² are as defined in Table 1.

az) 450 compounds of formula (I.az):

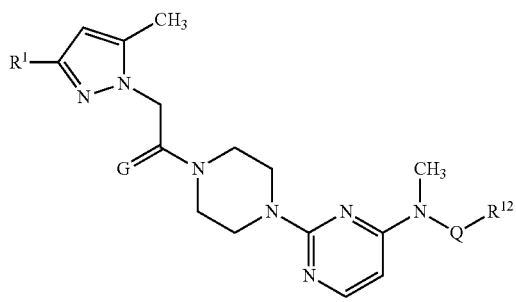

(I.az)

wherein G, Q, R¹ and R¹² are as defined in Table 1.

ba) 450 compounds of formula (I.ba):

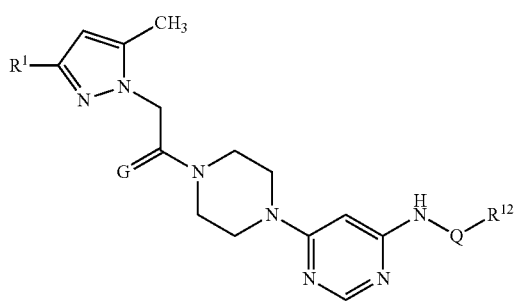

(I.ba)

wherein G, Q, R¹ and R¹² are as defined in Table 1.

bb) 450 compounds of formula (I.bb):

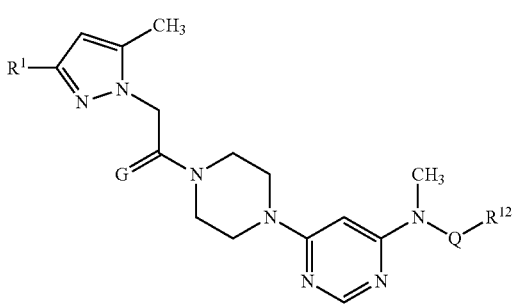

(I.bb)

wherein G, Q, R¹ and R¹² are as defined in Table 1.

bc) 450 compounds of formula (I.bc):

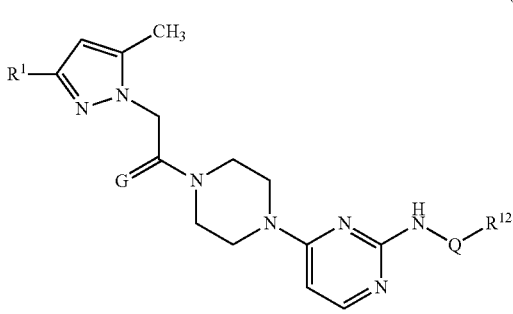

(I.bc)

wherein G, Q, R¹ and R¹² are as defined in Table 1.

bd) 450 compounds of formula (I.bd):

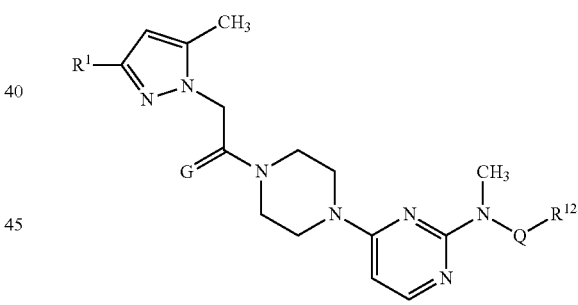

(I.bd)

wherein G, Q, R¹ and R¹² are as defined in Table 1.

be) 450 compounds of formula (I.be):

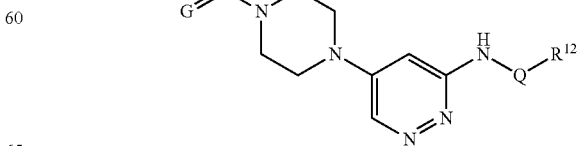

(I.be)

wherein G, Q, R¹ and R¹² are as defined in Table 1.

bf) 450 compounds of formula (I.bf):

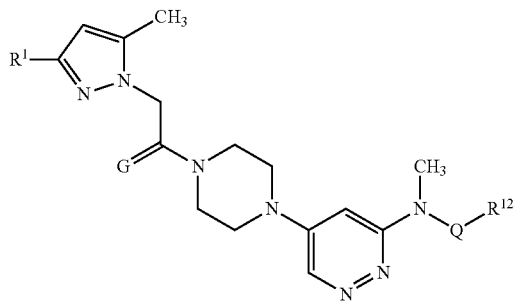

wherein G, Q, R$^1$ and R$^{12}$ are as defined in Table 1.

bg) 450 compounds of formula (I.bg):

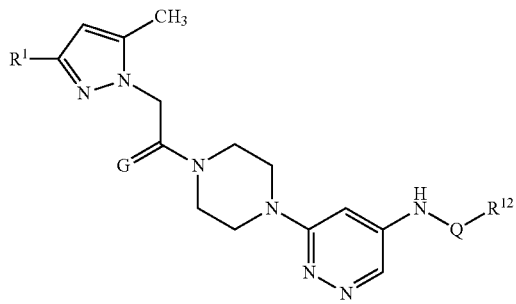

wherein G, Q, R$^1$ and R$^{12}$ are as defined in Table 1.

bh) 450 compounds of formula (I.bh):

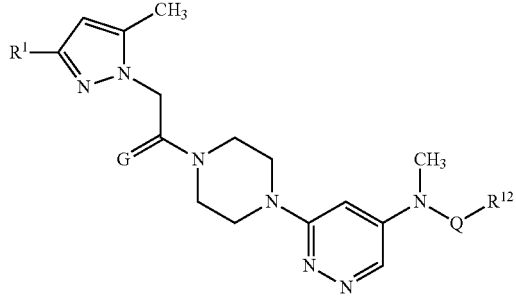

wherein G, Q, R$^1$ and R$^{12}$ are as defined in Table 1.

bi) 450 compounds of formula (I.bi):

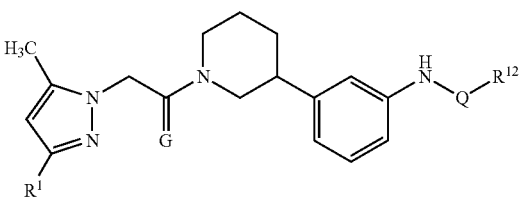

wherein G, Q, R$^1$ and R$^{12}$ are as defined in Table 1.

bj) 450 compounds of formula (I.bj):

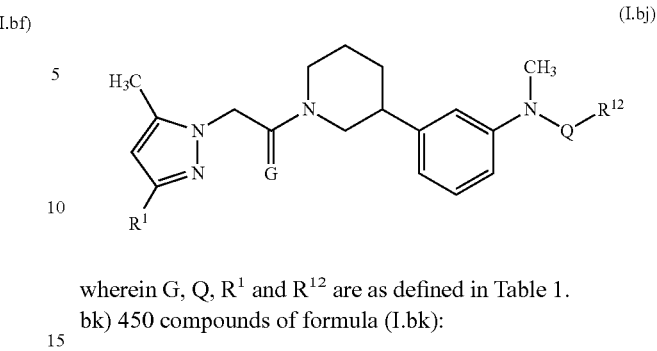

wherein G, Q, R$^1$ and R$^{12}$ are as defined in Table 1.

bk) 450 compounds of formula (I.bk):

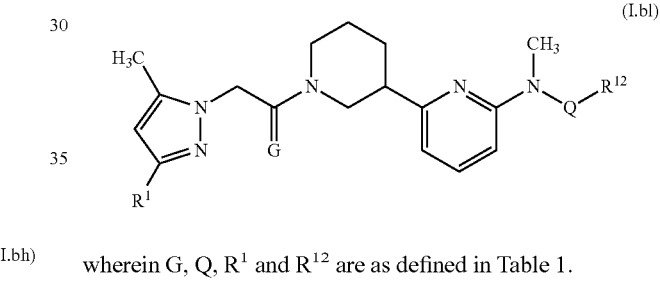

wherein G, Q, R$^1$ and R$^{12}$ are as defined in Table 1.

bl) 450 compounds of formula (I.bl):

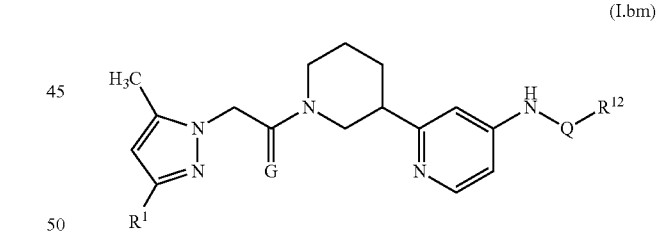

wherein G, Q, R$^1$ and R$^{12}$ are as defined in Table 1.

bm) 450 compounds of formula (I.bm):

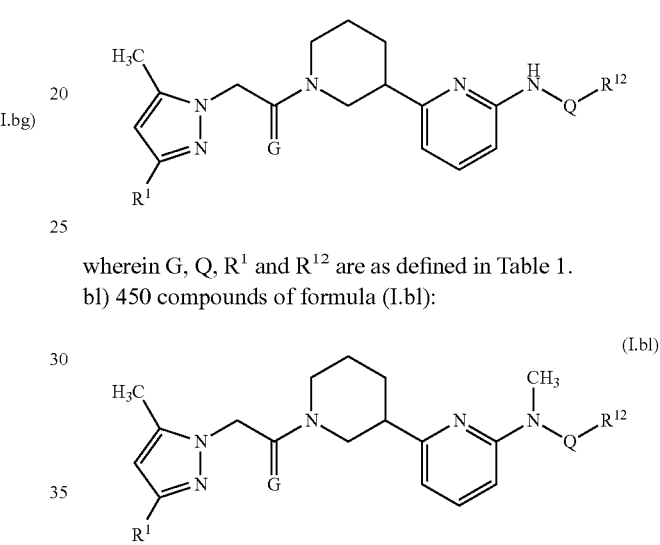

wherein G, Q, R$^1$ and R$^{12}$ are as defined in Table 1.

bn) 450 compounds of formula (I.bn):

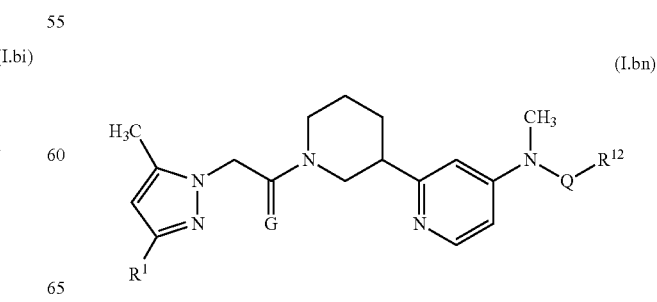

wherein G, Q, R$^1$ and R$^{12}$ are as defined in Table 1.

bo) 450 compounds of formula (I.bo):

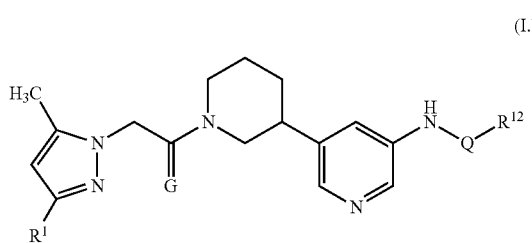

wherein G, Q, R¹ and R¹² are as defined in Table 1.

bp) 450 compounds of formula (I.bp):

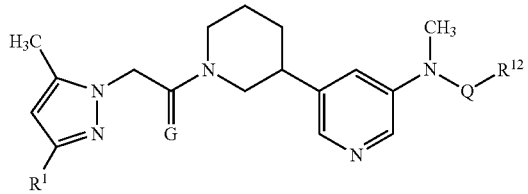

wherein G, Q, R¹ and R¹² are as defined in Table 1.

bq) 450 compounds of formula (I.bq):

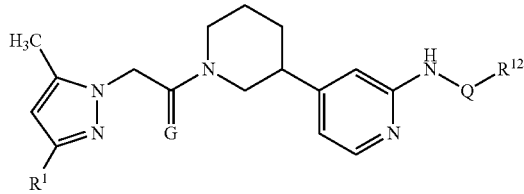

wherein G, Q, R¹ and R¹² are as defined in Table 1.

br) 450 compounds of formula (I.br):

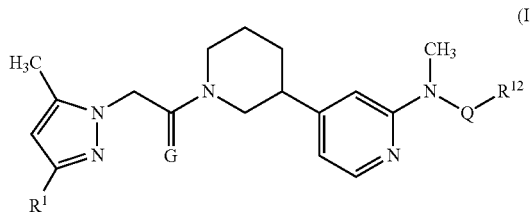

wherein G, Q, R¹ and R¹² are as defined in Table 1.

bs) 450 compounds of formula (I.bs):

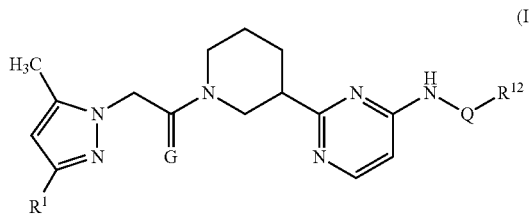

wherein G, Q, R¹ and R¹² are as defined in Table 1.

bt) 450 compounds of formula (I.bt):

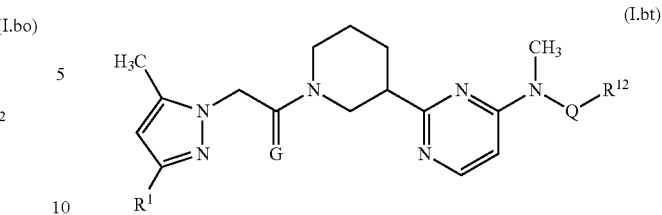

wherein G, Q, R¹ and R¹² are as defined in Table 1.

bu) 450 compounds of formula (I.bu):

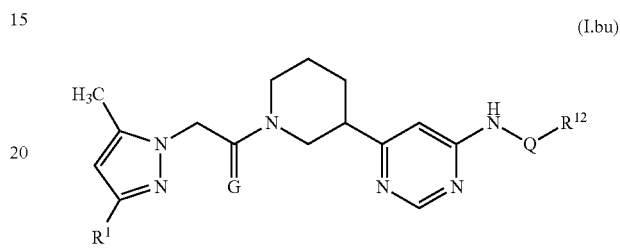

wherein G, Q, R¹ and R¹² are as defined in Table 1.

by) 450 compounds of formula (I.by):

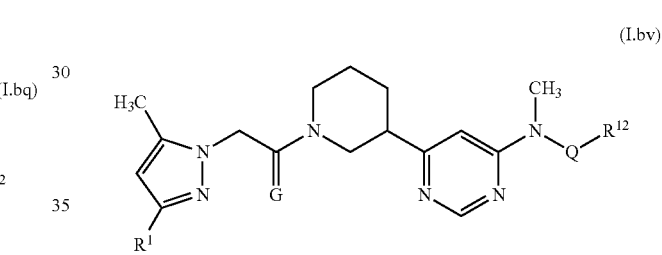

wherein G, Q, R¹ and R¹² are as defined in Table 1.

bw) 450 compounds of formula (I.bw):

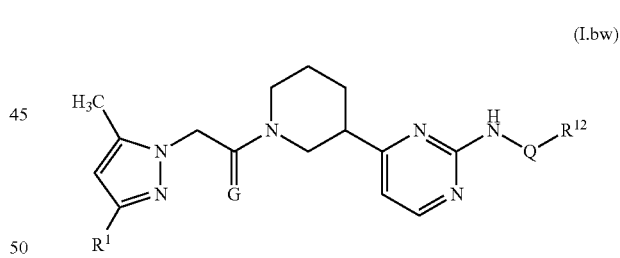

wherein G, Q, R¹ and R¹² are as defined in Table 1.

bx) 450 compounds of formula (I.bx):

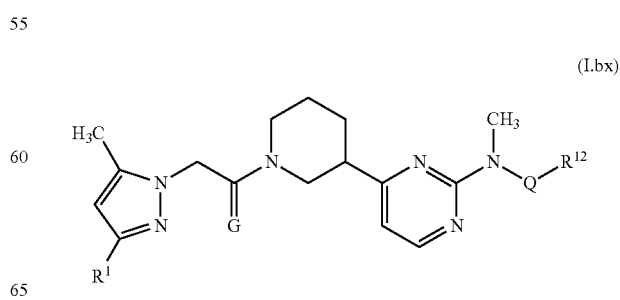

wherein G, Q, R¹ and R¹² are as defined in Table 1.

by) 450 compounds of formula (I.by):

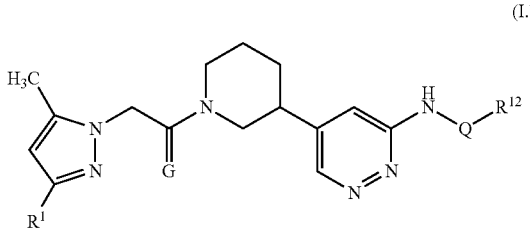

(I.by)

wherein G, Q, R$^1$ and R$^{12}$ are as defined in Table 1.

bz) 450 compounds of formula (I.bz):

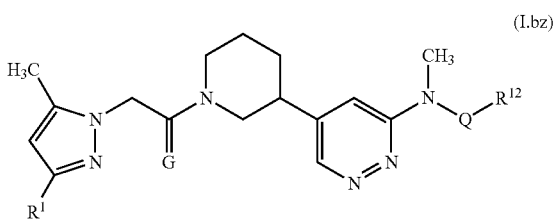

(I.bz)

wherein G, Q, R$^1$ and R$^{12}$ are as defined in Table 1.

ca) 450 compounds of formula (I.ca):

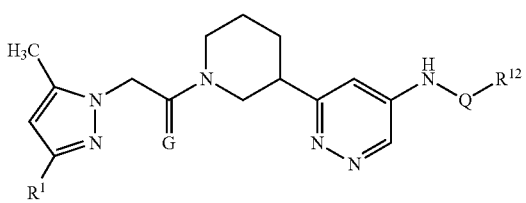

(I.ca)

wherein G, Q, R$^1$ and R$^{12}$ are as defined in Table 1.

cb) 450 compounds of formula (I.cb):

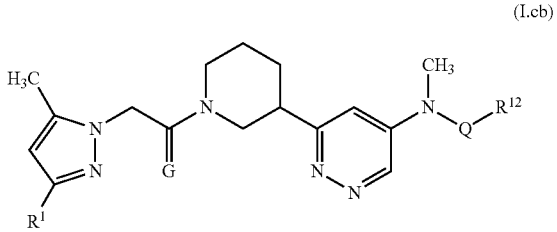

(I.cb)

wherein G, Q, R$^1$ and R$^{12}$ are as defined in Table 1.

Throughout this description, LC/MS means Liquid Chromatography Mass Spectroscopy and the description of the apparatus and the method is: (HP 1100 HPLC from Agilent, Phenomenex Gemini C18, 3 μm particle size, 110 Angström, 30×3 mm column, 1.7 mL/min., 60° C., H$_2$O+0.05% HCOOH (95%)/CH$_3$CN/MeOH 4:1+0.04% HCOOH (5%)—2 min.—CH$_3$CN/MeOH 4:1+0.04% HCOOH (5%)—0.8 min., ZQ Mass Spectrometer from Waters, ionization method: electrospray (ESI), Polarity: positive ions, Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400)).

Table 2 shows selected LC/MS data or m.p. (° C.) for compounds of Table 1.

TABLE 2

LC/MS data for compounds of Table 1

| Compound No. | LC/MS or m.p. |
| --- | --- |
| I.u.003 | Rt = 2.03 min; MS: m/z = 521 (M + 1) |
| I.u.036[a] | Rt = 2.24 min; MS: m/z = 505 (M + 1) |
| I.u.037[a] | Rt = 2.39 min; MS: m/z = 533 (M + 1) |
| I.w.003 | Rt = 1.96 min; MS: m/z = 522 (M + 1); (m.p. 105-106° C.) |
| I.w.005 | Rt = 1.83 min; MS: m/z = 522 (M + 1); (m.p. 138-139° C.) |
| I.y.003 | Rt = 1.49 min; MS: m/z = 522 (M + 1) |
| I.ae.003 | m.p. 120-122° C. |
| I.aq.003 | Rt = 1.95 min; MS: m/z = 523 (M + 1); (m.p. 149-150° C.) |
| I.aq.004 | Rt = 1.77 min; MS: m/z = 509 (M + 1); (m.p. 127° C.) |
| I.aq.005 | Rt = 1.81 min; MS: m/z = 523(M + 1); (m.p. 125° C.) |
| I.ao.003 | Rt = 1.98 min; MS: m/z = 522 (M + 1) |
| I.ay.003 | Rt = 1.92 min; MS: m/z = 524 (M + 1); (m.p. 44-145° C.) |

[a]the following apparatus and LC/MS method was used: (1200 HPLC from Agilent, Waters XterraMS-C18, 3.5 mm particle size, 155 Angström, 30 × 4.6 mm column, 1.8 mL/min., 30° C., H$_2$O + 0.1% HCOOH (90%)/CH$_3$CN + 0.1% HCOOH (10%) - 2 min. -CH3CN + 0.1% HCOOH(100)-3 min- CH3CN + 0.1% HCOOH(100)-3.2 min - H$_2$O + 0.1% HCOOH (90%)/CH$_3$CN + 0.1% HCOOH (10%)-4 min- H$_2$O + 0.1% HCOOH (90%)/CH$_3$CN + 0.1% HCOOH (10%), 6410-Triple Quad Mass Spectrometer from Agilent, ionization method: electrospray (ESI), Polarity: Both ions, Capillary (kV) 4.00, Frag (V) 100.00, Chamber current-1.3 microA, Source parameters: Gas Temp (° C.) 350, Gas Flow (l/min) 11; Nebulizer (psi): 35.

The compounds according to the present invention can be prepared according to the above-mentioned reaction schemes, in which, unless otherwise stated, the definition of each variable is as defined above for a compound of formula (I).

BIOLOGICAL EXAMPLES

*Phytophthora infestans*/Tomato/Leaf Disc Preventative (Tomato Late Blight)

Tomato leaf disks are placed on water agar in multiwell plates (24-well format) and sprayed with the formulated test compound diluted in water. The leaf disks are inoculated with a spore suspension of the fungus 1 day after application. The inoculated leaf disks are incubated at 16° C. and 75% rh under a light regime of 24 h darkness followed by 12 h light/12 h darkness in a climate cabinet and the activity of a compound is assessed as percent disease control compared to untreated when an appropriate level of disease damage appears in untreated check leaf disks (5-7 days after application).

Compound I.u.003, I.w.003, I.w.005, I.aq.003, I.aq.005, I.ae.003, I.ay.003 at 200 ppm give at least 80% disease control in this test when compared to untreated control leaf disks under the same conditions, which show extensive disease development.

*Phytophthora infestans*/Potato/Preventative (Potato Late Blight)

2-week old potato plants cv. Bintje are sprayed in a spray chamber with the formulated test compound diluted in water. The test plants are inoculated by spraying them with a sporangia suspension 2 days after application. The inoculated test plants are incubated at 18° C. with 14 h light/day and 100% rh in a growth chamber and the percentage leaf area covered by disease is assessed when an appropriate level of disease appears on untreated check plants (5-7 days after application).

Compounds I.u.003, I.w.003 and I.ao.003 at 200 ppm give at least 80% disease control in this test when compared to untreated control leaf disks under the same conditions, which show extensive disease development.

*Phytophthora infestans*/Potato/Long Lasting (Potato Late Blight)

2-week old potato plants cv. Bintje are sprayed in a spray chamber with the formulated test compound diluted in water. The test plants are inoculated by spraying them with a sporangia suspension 6 days after application. The inoculated test plants are incubated at 18° C. with 14 h light/day and 100% rh in a growth chamber and the percentage leaf area covered by disease is assessed when an appropriate level of disease appears on untreated check plants (9-11 days after application).

Compounds I.u.003, and I.ao.003 at 200 ppm give at least 80% disease control in this test when compared to untreated control leaf disks under the same conditions, which show extensive disease development.

*Plasmopara viticola*/Grape/Leaf Disc Preventative (Grape Downy Mildew)

Grape vine leaf disks are placed on water agar in multiwell plates (24-well format) and sprayed with the formulated test compound diluted in water. The leaf disks are inoculated with a spore suspension of the fungus 1 day after application. The inoculated leaf disks are incubated at 19° C. and 80% rh under a light regime of 12 h light/12 h darkness in a climate cabinet and the activity of a compound is assessed as percent disease control compared to untreated when an appropriate level of disease damage appears in untreated check leaf disks (6-8 days after application).

Compounds I.u.003, I.w.003, I.w.005, I.aq.003, I.aq.005, I.ae.003 at 200 ppm give at least 80% disease control in this test when compared to untreated control leaf disks under the same conditions, which show extensive disease development.

*Plasmopara viticola*/Grape/Preventative (Grape Downy Mildew)

5-week old grape seedlings cv. Gutedel are sprayed in a spray chamber with the formulated test compound diluted in water. The test plants are inoculated by spraying a sporangia suspension on their lower leaf surface one day after application. The inoculated test plants are incubated at 22° C. and 100% rh in a greenhouse and the percentage leaf area covered by disease is assessed when an appropriate level of disease appears on untreated check plants (6-8 days after application).

Compounds I.u.003, I.w.003 and I.ao.003 at 200 ppm give at least 80% disease control in this test when compared to untreated control leaf disks under the same conditions, which show extensive disease development.

*Plasmopara viticola*/Grape/Long Lasting (Grape Downy Mildew)

5-week old grape seedlings cv. Gutedel are sprayed in a spray chamber with the formulated test compound diluted in water. The test plants are inoculated by spraying a sporangia suspension on their lower leaf surface 6 days after application. The inoculated test plants are incubated at 22° C. and 100% rh in a greenhouse and the percentage leaf area covered by disease is assessed when an appropriate level of disease appears on untreated check plants (11-13 days after application).

Compounds I.u.003, I.w.003 and I.ao.003 at 200 ppm give at least 80% disease control in this test when compared to untreated control leaf disks under the same conditions, which show extensive disease development.

*Pythium ultimum*/Liquid Culture (Seedling Damping Off)

Mycelia fragments and oospores of a newly grown liquid culture of the fungus are directly mixed into nutrient broth (PDB potato dextrose broth). After placing a (DMSO) solution of test compound into a microtiter plate (96-well format), the nutrient broth containing the fungal mycelia/spore mixture is added. The test plates are incubated at 24° C. and the inhibition of growth is determined photometrically 2-3 days after application.

Compounds I.u.003, I.w.003, I.aq.003, I.ae.003, I.ay.003 at 200 ppm give at least 80% disease control in this test when compared to untreated control leaf disks under the same conditions, which show extensive disease development.

What is claimed is:
1. A compound of formula I

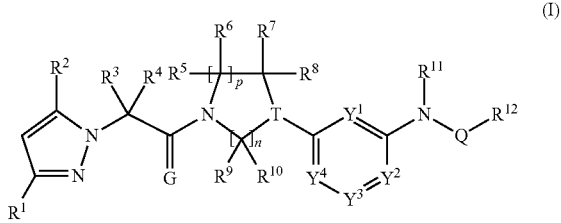

wherein
G is O or S;
T is $CR^{13}$ or N;
$Y^1$, $Y^2$, $Y^3$ and $Y^4$ are independently $CR^{14}$ or N;
Q is —C(=O)-z, —C(=S)-z, —C(=O)—O-z, —C(=O)—N($R^{15}$)-z or —C(=S)—N($R^{16}$)-z, in each case z indicates the bond that is connected to $R^{12}$;
n is 1 or 2;
p is 1 or 2, providing that when n is 2, p is 1;
$R^1$, $R^2$, $R^3$, $R^4$, $R^5$, $R^6$, $R^7$, $R^8$, $R^9$, $R^{10}$, $R^{13}$ and $R^{14}$ each independently are hydrogen, halogen, cyano, $C_1$-$C_4$alkyl or $C_1$-$C_4$haloalkyl;
$R^{11}$, $R^{15}$ and $R^{16}$ each independently are hydrogen, $C_1$-$C_4$alkyl, $C_3$-$C_5$cycloalkyl or $C_1$-$C_4$alkoxy;
$R^{12}$ is aryl, heteroaryl, arylalkyl, heteroarylalkyl, a group (A) or a group (B):

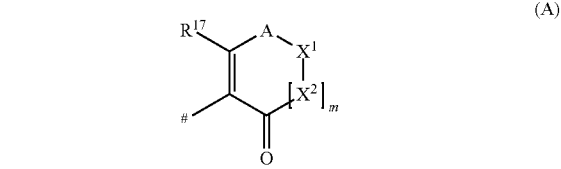

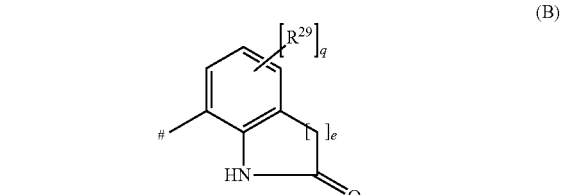

wherein the aryl, heteroaryl, arylalkyl and heteroarylalkyl are optionally substituted by one or more $R^{29}$;
A is C($R^{18}R^{19}$), C(=O), C(=S), $NR^{24}$, O or S;
$X^1$ is C($R^{20}R^{21}$), C(=O), C(=S), $NR^{24}$, O or S;
$X^2$ is C($R^{22}R^{23}$), C(=O), C(=S), $NR^{24}$, O or S;
$R^{17}$ is hydroxyl, $O^-M^+$, OC(=O)$R^{28}$, amino or $NHR^{25}$;
$M^+$ is a metal cation or ammonium cation;
$R^{18}$, $R^{19}$, $R^{20}$, $R^{21}$, $R^{22}$ and $R^{23}$ each independently are hydrogen, halogen, hydroxyl, amino, cyano, $C_1$-$C_8$alkyl, $C_2$-$C_8$alkenyl, $C_2$-$C_8$alkynyl, $C_3$-$C_8$cycloalkyl, $C_1$-$C_8$alkoxy, $C_1$-$C_8$alkylthio, $C_1$-$C_8$alkylsulfonyl, $C_1$-$C_8$alkylsulfinyl, aryl, heteroaryl or $NHR^{25}$, wherein alkyl, alkenyl, alkynyl, cycloalkyl, alkoxy, aryl and heteroaryl are optionally substituted by one or more $R^{26}$; and wherein $R^{18}$ and $R^{19}$, $R^{20}$ and $R^{21}$, and/or $R^{22}$ and $R^{23}$ may together form a saturated three- to six-membered alicyclic or heterocyclic ring wherein the aliyclic and heterocyclic rings are optionally substituted by one or more $R^{27}$; and/or $R^{18}$ and $R^{20}$, and/or $R^{21}$ and $R^{22}$ may together form a saturated or partially unsaturated four- to seven-membered alicyclic or heterocyclic ring wherein the aliyclic and heterocyclic rings are optionally substituted by one or more $R^{27}$; and/or $R^{18}$ and $R^{22}$ may together form a saturated or partially unsaturated four-to seven-membered alicyclic or heterocyclic ring wherein the aliyclic and heterocyclic rings are optionally substituted by one or more $R^{27}$;

$R^{24}$ and $R^{25}$ each independently are hydrogen, $C_1$-$C_8$alkyl, $C_1$-$C_8$haloalkyl $C_2$-$C_8$alkenyl, $C_1$-$C_8$haloalkenyl $C_2$-$C_8$alkynyl, $C_2$-$C_8$haloalkynyl, $C_3$-$C_8$cycloalkyl, $C_3$-$C_8$halocycloalkyl, $C_1$-$C_8$alkoxy, $C_1$-$C_8$haloalkoxy, $C_1$-$C_8$alkylcarbonyl, $C_1$-$C_8$haloalkylcarbonyl, $C_1$-$C_8$alkylsulfonyl, $C_1$-$C_8$haloalkylsulfonyl, amino, $NH(C_1$-$C_8$alkyl), $N(C_1$-$C_8$alkyl$)_2$, aryl or heterocyclyl, wherein aryl and heterocyclyl are optionally substituted by one or more $R^{27}$;

each $R^{26}$ independently is halogen, cyano, amino, nitro, hydroxyl, mercapto, $C_1$-$C_8$alkyl, $C_2$-$C_8$alkenyl, $C_2$-$C_8$alkynyl, $C_3$-$C_8$cycloalkyl, $C_3$-$C_8$cycloalkyl-$C_1$-$C_4$alkyl, $C_3$-$C_8$cycloalkyl-$C_1$-$C_4$alkyloxy, $C_3$-$C_8$cycloalkyl-$C_1$-$C_4$alkylthio, $C_1$-$C_8$alkoxy, $C_3$-$C_8$cycloalkyloxy, $C_1$-$C_8$alkenyloxy, $C_2$-$C_8$alkynyloxy, $C_1$-$C_8$alkylthio, $C_1$-$C_8$alkylsulfonyl, $C_1$-$C_8$alkylsulfinyl, $C_3$-$C_8$cycloalkylthio, $C_3$-$C_8$cycloalkylsulfonyl, $C_3$-$C_8$cycloalkylsulfinyl, aryl, aryloxy, arylthio, arylsulfonyl, arylsulfinyl, aryl-$C_1$-$C_4$alkyl, aryl-$C_1$-$C_4$alkyloxy, aryl-$C_1$-$C_4$alkylthio, heterocyclyl, heterocycyl-$C_1$-$C_4$alkyl, heterocycyl-$C_1$-$C_4$alkyloxy, heterocyclyl-$C_1$-$C_4$alkylthio, $NH(C_1$-$C_8$alkyl), $N(C_1$-$C_8$alkyl$)_2$, $C_1$-$C_4$alkylcarbonyl, $C_3$-$C_8$cycloalkylcarbonyl, $C_2$-$C_8$alkenylcarbonyl, $C_2$-$C_8$alkynylcarbonyl, wherein alkyl, alkenyl, alkynyl, cycloalkyl, alkoxy, alkenyloxy, alkynyloxy and cycloalkoxy are optionally substituted by halogen, and wherein aryl and heterocyclyl are optionally substituted by one or more $R^{27}$;

each $R^{27}$ is independently is halogen, cyano, $C_1$-$C_4$alkyl, $C_1$-$C_4$haloalkyl, $C_1$-$C_4$alkoxy or $C_1$-$C_4$haloalkoxy;

$R^{28}$ is $C_1$-$C_6$alkyl or $C_1$-$C_6$alkoxy;

each $R^{29}$ independently is halogen, hydroxyl, cyano, mercapto, nitro, $C_1$-$C_4$alkyl, $C_1$-$C_4$haloalkyl, $C_1$-$C_4$alkoxy, $C_1$-$C_4$haloalkoxy, $C_1$-$C_4$alkylthio, $N(R^{30})_2$, phenyl or heteroaryl, wherein phenyl and heteroaryl are optionally substituted by one or more substituents independently selected from halogen, cyano, $C_1$-$C_4$ alkyl, $C_1$-$C_4$ haloalkyl, $C_1$-$C_4$ alkoxy and $C_1$-$C_4$ haloalkoxy;

each $R^{30}$ independently is hydrogen, cyano, $C_1$-$C_4$alkyl, $C_1$-$C_4$alkylcarbonyl, $C_1$-$C_4$haloalkylcarbonyl, $C_1$-$C_4$alkylsulfonyl or $C_1$-$C_4$haloalkylsulfonyl;

e is 1 or 2;

q is 1, 2, or 3; and m is 0 or 1, providing that when m is 1, $X^1$ and $X^2$ cannot both be oxygen;

or a salt or a N-oxide thereof.

2. A compound according to claim 1, wherein group (A) is selected from A1 to A19

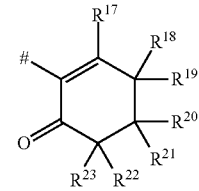
A1

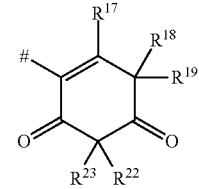
A2

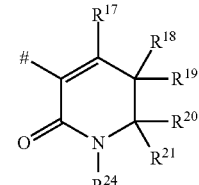
A3

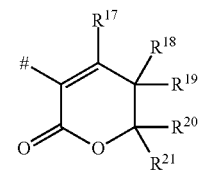
A4

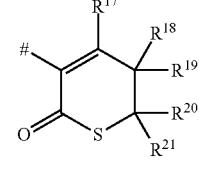
A5

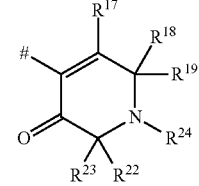
A6

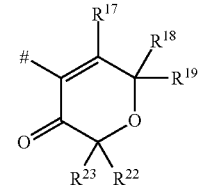
A7

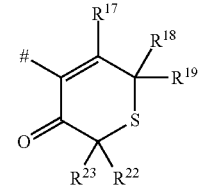
A8

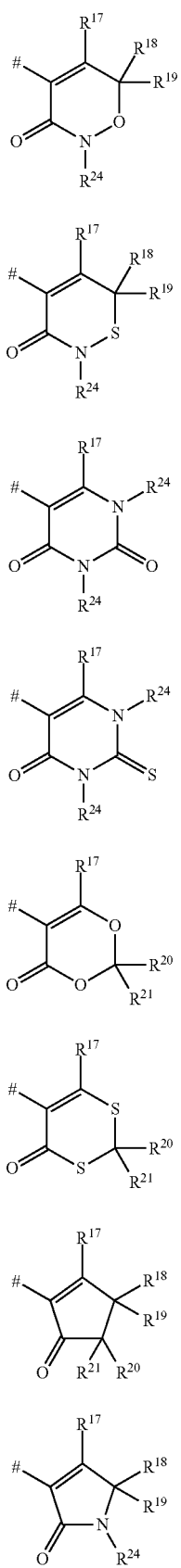

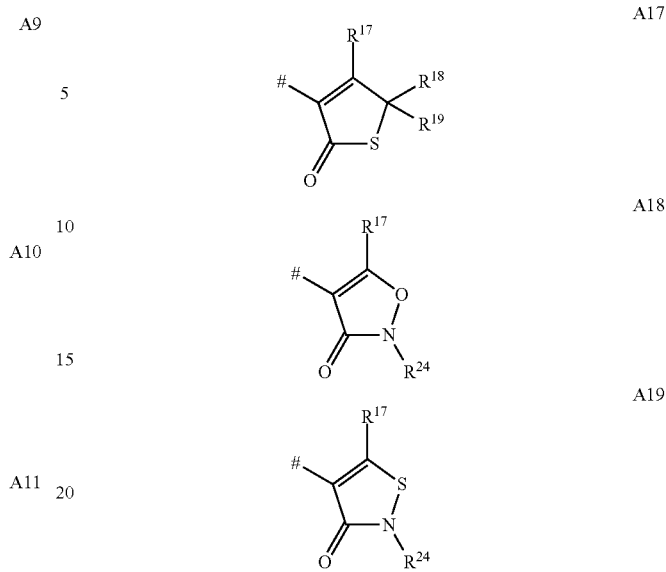

3. A compound according to claim 1, wherein $R^{12}$ is phenyl, heteroaryl, phenyl-$C_1$-$C_4$alkyl, heteroaryl-$C_1$-$C_4$alkyl, a group (A) or a group (B), wherein the phenyl, phenyl-$C_1$-$C_4$alkyl, heteroaryl and heteroaryl-$C_1$-$C_4$alkyl are optionally substituted by one or more $R^{29}$; and wherein heteroaryl is selected from furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, imiazothiazoyl, quinolinyl, quinoxalinyl, isoquinolinyl, phthalazinyl, quinoxalinyl, quinazolinyl, cinnolinyl and naphthyridinyl.

4. A compound according to claim 2, wherein $R^{12}$ is phenyl, benzyl, or group (A), wherein the phenyl and benzyl are optionally substituted by one or more $R^{29}$; and wherein group (A) is A1 or A2.

5. A compound according to claim 1, wherein $R^{17}$ is hydroxyl or $O^-M^+$.

6. A compound according to claim 1, wherein at least three of $Y^1, Y^2, Y^3$ and $Y^4$ are CH and the other of $Y^1, Y^2, Y^3$ and $Y^4$ is CH or N.

7. A compound according to claim 1, wherein $Y^2$ is N.

8. A compound according to claim 1, wherein $R^1$ and $R^2$ are independently methyl or halomethyl.

9. A compound according to claim 1, wherein $R^3, R^4, R^5, R^6, R^7, R^8, R^9, R^{10}, R^{13}$ and $R^{14}$ are independently hydrogen, halogen, methyl or halomethyl.

10. A compound according to claim 1, wherein G is O and Q is —C(=O)-z, wherein z indicates the bond that is connected to $R^{12}$.

11. A compound according to claim 1, wherein p is 1 and n is 2.

12. A compound according to claim 1, wherein $R^{12}$ is aryl, heteroaryl or group (A) and the aryl or heteroaryl is substituted by hydroxyl and optionally substituted by one or two further substituents.

13. A compound according to claim 12, wherein the hydroxyl is at the ortho position.

14. A fungicidal composition comprising at least one compound as defined in claim 1 and an agriculturally acceptable carrier, optionally comprising an adjuvant, and optionally comprising one or more additional pesticidally active compounds.

15. A method of controlling or preventing an infestation of plants, propagation material thereof, harvested crops or non-living materials by phytopathogenic or spoilage microorganisms or organisms potentially harmful to man, which comprises the application of a compound as defined in claim 1, to the plant, to parts of the plants or to the locus thereof, to propagation material thereof or to any part of the non-living materials.

* * * * *